US012612638B2

(12) United States Patent
Melis et al.

(10) Patent No.: US 12,612,638 B2
(45) Date of Patent: Apr. 28, 2026

(54) FUSION CONSTRUCTS TO EXPRESS BIOPHARMACEUTICAL POLYPEPTIDES IN CYANOBACTERIA

(71) Applicant: The Regents of the University of California, Oakland, CA (US)

(72) Inventors: Anastasios Melis, El Cerrito, CA (US); Nico Betterle, Pleasanton, CA (US); Diego Hidalgo Martinez, El Cerrito, CA (US); Andrew C. Saphire, Solana Beach, CA (US)

(73) Assignee: The Regents of the University of California, Oakland, CA (US)

( * ) Notice: Subject to any disclaimer, the term of this patent is extended or adjusted under 35 U.S.C. 154(b) by 964 days.

(21) Appl. No.: 17/642,330

(22) PCT Filed: Sep. 11, 2020

(86) PCT No.: PCT/US2020/050528

§ 371 (c)(1),
(2) Date: Mar. 11, 2022

(87) PCT Pub. No.: WO2021/050968

PCT Pub. Date: Mar. 18, 2021

(65) Prior Publication Data

US 2022/0372499 A1 Nov. 24, 2022

Related U.S. Application Data

(60) Provisional application No. 62/898,891, filed on Sep. 11, 2019.

(51) Int. Cl.

| | |
|---|---|
| ***C07K 14/195*** | (2006.01) |
| ***C12N 1/205*** | (2026.01) |
| ***C12N 15/62*** | (2006.01) |
| ***C12N 15/74*** | (2006.01) |
| ***C12P 21/06*** | (2006.01) |

(52) U.S. Cl.

CPC ............ *C12N 15/74* (2013.01); *C07K 14/195* (2013.01); *C12N 1/205* (2021.05); *C07K 2319/50* (2013.01)

(58) Field of Classification Search

CPC .. C12P 21/06; C12P 5/00; C12P 7/065; C12N 1/21; C12N 1/13; C12N 15/62; C12N 15/63; C12N 15/66; C07K 2319/50

See application file for complete search history.

(56) References Cited

U.S. PATENT DOCUMENTS

| | | | |
|---|---|---|---|
| 7,947,478 | B2 | 5/2011 | Melis |
| 8,133,708 | B2 | 3/2012 | Melis |
| 8,993,290 | B2 | 3/2015 | Melis |
| 9,951,354 | B2 | 4/2018 | Melis |
| 10,385,310 | B2 | 8/2019 | Melis |
| 10,563,228 | B2 | 2/2020 | Melis |
| 10,876,124 | B2 | 12/2020 | Melis |
| 10,889,835 | B2 | 1/2021 | Melis |
| 11,884,927 | B2 | 1/2024 | Melis |
| 12,391,950 | B2 | 8/2025 | Melis |
| 2004/0175359 | A1 | 9/2004 | Desjarlais et al. |
| 2009/0011995 | A1 | 1/2009 | Lee et al. |
| 2018/0171342 | A1 | 6/2018 | Melis et al. |
| 2024/0376174 | A1 | 11/2024 | Melis et al. |

FOREIGN PATENT DOCUMENTS

| | | | |
|---|---|---|---|
| JP | 85076 | * | 3/2002 |
| WO | 2011/143557 | A2 | 11/2011 |
| WO | 2013/010048 | A2 | 1/2013 |
| WO | 2016/210154 | A1 | 12/2016 |
| WO | 2017/205788 | A2 | 11/2017 |

OTHER PUBLICATIONS

PCT/US2020/050528, International Search Report and Written Opinion, dated Feb. 10, 2021, 18 pages.

European Patent Application No. 20864117.5, "European Supplementary Search Report," mailed Sep. 25, 2023, 8 pages.

Betterle, et al., "Cyanobacterial Production of Biopharmaceutical and Biotherapeutic Proteins," Frontiers in Plant Science, vol. 11, Mar. 3, 2020, 16 pages.

Australian Patent Application No. 2020344678, "Examination Report," mailed Oct. 15, 2025, 4 pages.

* cited by examiner

*Primary Examiner* — Maryam Monshipouri

(74) *Attorney, Agent, or Firm* — Kilpatrick Townsend & Stockton LLP

(57) ABSTRACT

This invention provides compositions and methods for providing high product yield of transgenes encoding biopharmaceutical polypeptides in cyanobacteria and microalgae.

14 Claims, 19 Drawing Sheets

Specification includes a Sequence Listing.

a
kD
250
150
100
75
50
37
25
20
15
MW
WT 1
WT 2
IFN 1
IFN 2
CpcB-IFN 1
CpcB-IFN 2
CpcB*IFN 1
CpcB*IFN 2
- RbcL
- CpcB*IFN
- CmR
- CpcB
- CpcA
0.25 μg Chl
b
WT 1
WT 2
IFN 1
IFN 2
CpcB-IFN 1
CpcB-IFN 2
CpcB*IFN 1
CpcB*IFN 2
0.25 μg Chl
α-IFN antibodies

FUSION CONSTRUCTS TO EXPRESS BIOPHARMACEUTICAL POLYPEPTIDES IN CYANOBACTERIA

CROSS-REFERENCE TO RELATED APPLICATIONS

This application is a U.S. National Phase of International Application No. PCT/US2020/050528, filed Sep. 11, 2020, which claims priority benefit of U.S. Provisional Application No. 62/898,891, filed Sep. 11, 2019, each of which applications is herein incorporated by reference in its entirety for all purposes.

SEQUENCE LISTING PROVIDED AS ASCII FORMAT FILE

This application contains a Sequence Listing submitted electronically in ASCII format and is herein incorporated by reference in its entirety. Said ASCII copy, created on Mar. 10, 2022, is named 086540_1303556_SEQ LST.txt and is 74,632 bytes in size.

BACKGROUND OF THE INVENTION

Efforts to express human therapeutic proteins in photosynthetic microorganisms abound in the literature. In their preponderance, these entail heterologous transformation of a microalgal chloroplast as a synthetic biology platform for the production of biopharmaceutical and therapeutic proteins (Dyo and Purton 2018, and references therein). The vast majority of such efforts have employed transformation of the chloroplast in the model green microalga *Chlamydomonas reinhardtii* via double homologous recombination of exogenous constructs encoding heterologous proteins (Surzycki et al. 2009; Tran et al. 2009; Coragliotti et al. 2011; Gregory et al. 2013; Jones and Mayfield 2013; Rasala and Mayfield 2015; Baier et al. 2018). A common feature of these efforts is the low yield of the transgenic biopharmaceutical proteins, not exceeding 1% of the total *Chlamydomonas reinhardtii* protein (Dyo and Purton 2018). In general, there is a need to develop methods that will systematically and reliably over-express eukaryotic, including human therapeutic, proteins in photosynthetic microorganisms, at levels that exceed 1% of the total cell protein.

Cyanobacteria such as *Synechocystis* and other microalgae can be used as photosynthetic platforms for the heterologous generation of products of interest. For example, bacterial proteins can be heterologously over-expressed in cyanobacteria, reportedly up to 20% of total soluble protein, by using the strong cpc operon promoter and possibly other endogenous or exogenous promoters (Zhou et al. 2014, Kirst et al. 2014; Formighieri and Melis 2017). By way of illustration, Zhou et al. (2014), described the function of a modified (partial) endogenous cyanobacterial promoter (Pcpc560), derived from the native cyanobacterial cpc operon promoter. They examined the efficacy of this promoter to express (i) the trans-enoyl-CoA reductase (Ter) protein from *Treponema denticola*, a Gram-negative, obligate anaerobic bacterium, and (ii) the D-lactate dehydrogenase (DidhE) protein from *Escherichia coli*. Both of these bacterial-origin genes and proteins were readily overexpressed in cyanobacteria under the control of the Pcpc. Kirst et al. (2014) showed that *Synechocystis* readily overexpressed, at the protein level and under the native Pcpc, the nptI gene from *Escherichia coli*, encoding the neomycin phosphotransferase, a kanamycin resistance conferring protein. Similarly. Xiong et al. (2015) showed overexpression of the *Pseudomonas syringae* efe gene, encoding an ethylene forming enzyme, in *Synechocystis* sp. PCC 6803 and enhanced EFE protein accumulation upon transformation of *Synechocystis* with multiple copies of the *P. syringae* efe gene (Xiong et al. 2015). Likewise, Chaves and co-workers provided evidence that cyanobacteria will over-express, at the protein level, the cmR gene from *Escherichia coli*, encoding a chloramphenicol resistance protein (Chaves et al. 2016), and the isopentenyl diphosphate isomerase (fni) gene from *Streptococcus pneumoniae*, either under the native Pcpc (Chaves et al. 2016) or heterologous Ptrc promoter (Chaves et al. 2018).

In separate work, Desplancq et al. (2005) showed that transgenic *Anabaena* sp. PCC 7120, a filamentous cyanobacterium, was able to express the *Escherichia coli*, e.g. bacterial origin, maltose-binding protein (MBP), yielding up to 250 mg MBP per L of culture. In further work, Desplancq et al. (2008) showed that *Anabaena* was also able to express 100 mg per L of gyrase B (GyrB), a 23 kD *Escherichia coli* protein. This is consistent with the notion that cyanobacteria easily express other “bacterial” origin proteins.

However, recent experience has also shown that heterologous expression of eukaryotic plant and yeast genes occurs at low protein levels, regardless of the promoter used and mRNA levels achieved in the cyanobacterial cytosol (Formighieri and Melis 2016). For example, plant terpene synthases could not be expressed well in cyanobacteria under the control of different strong endogenous and heterologous promoters (Formighieri and Melis 2014; Englund et al. 2018). Heterologous expression in cyanobacteria of the isoprene synthase (Lindberg et al. 2010; Bentley and Melis 2012), β-phellandrene synthase (Bentley et al. 2013), geranyl diphosphate (GPP) synthase from a higher plant origin (Bentley et al 2014; Formighieri et al 2017; Betterle and Melis 2018), and the alcohol dehydrogenase (ADH1) gene from yeast (Chen et al. 2013), all showed low levels of recombinant protein expression, even under the control of strong endogenous (e.g. psbA2, rbcL, cpc) or strong heterologous promoters (e.g. Ptrc), and even after following a careful codon-use optimization of the target transgene (Lindberg et al. 2010; Bentley and Melis 2012; Ungerer et al. 2012; Bentley et al. 2013; Chen and Melis 2013; Formighieri and Melis 2014a; Englund et al. 2018). Similarly, only low levels of expression were reported for a chimeric complex of plant enzymes, including the ethylene synthase efe gene from *Solanum lycopersicum* (tomato) (Jindou et al. 2014; Xue et al. 2014), limonene synthase from *Mentha spicata* (spearmint) (Davies et al. 2014) and *Picea sitchensis* (Sitka spruce) (Halfmann et al. 2014a), the sesquiterpene famesene and bisabolene synthases from *Picea abies* (Norway spruce) (Halfmann et al. 2014b) and *Abies grandis* (grand fir) (Davies et al 2014). In these and other studies, transgenic protein levels were not evident on an SDS-PAGE Coomassie stain of protein extracts and, frequently, shown by sensitive Western blot analysis only.

Animal-origin eukaryotic transgenes are difficult to express in cyanobacteria. Desplancq et al. (2008) showed that the eukaryotic (human) oncogene E6 protein, when expressed in cyanobacteria, is toxic to the cells. To manage the toxicity, they separated in time cell growth from recombinant protein expression. They resorted to using the inducible nitrate assimilation nir promoter of the filamentous cyanobacterium *Anabaena*, as the promoter for the expression of their transgenes. The latter is repressed in the presence of ammonium (NH4+) salts but induced in the absence of ammonium and presence of nitrate (NO3−). They grew *Anabaena* to high cell density in the presence of ammonium (NH4+), thereby blocking the expression of the transgenes. By the time cells reached a high density in the culture, the pre-calculated amount of ammonium was either consumed, or experimentally replaced with nitrate salts. Cells then activated the nitrate reductase nir promoter, as they were forced to rely on nitrate nutrients for further growth. This induction process resulted in the accumulation of small amounts of the transgenic eukaryotic (human) oncogene E6 protein, although this product again proved to be lethal to the cells under these conditions. Since efforts to express the oncogene E6 by itself failed due to toxicity of the product, Desplancq et al. (2008) undertook to express it as a fusion-protein with the highly-expressed maltose-binding protein as the leader sequence in a MBP*E6 fusion. This effort resulted in a yield of 1 mg protein per L after 5 days of nir induction, i.e., 0.4% of the amount measured with MBP as the solo recombinant protein. They suggested that the MBP*E6 fusion protein has an inhibitory effect on its own expression and further that this oncoprotein is toxic to *Anabaena* cells, evidenced from the about 50% inhibition in cell growth observed in the MBP*E6 expressing transformants.

Interferons (IFNs) are a group of signaling proteins made and released by host cells in response to the presence of viruses. Interferon a-2a (IFNA2) is a member of the Type I interferon cytokine family, known for its antiviral and antiproliferative functions. Recombinant *Escherichia coli* expression of IFNA2 resulted in inclusion body formation, or required numerous purification steps that decreased the protein yield. Bis et al. (2014) described an expression and purification scheme for IFNA2 using a pET-SUMO bacterial expression system and a single purification step. Using the SUMO protein as the fusion tag increased the soluble protein expression and minimized the amount of inclusion bodies in *E. coli*. Following protein expression, the SUMO tag was cleaved with the Ulp1 protease leaving no additional amino acids on the fusion terminus following cleavage (Bis et al. 2014). The purified protein had antiviral and antiproliferative activities comparable to the WHO International Standard, NIBSC 95/650, and the IFNA2 standard available from PBL Assay Science.

Tissue-type plasminogen activator (tPA) is a protein involved in the breakdown of blood clots. Human tPA has a molecular weight of ~70 kD in the single-chain form. tPA has five peptide domains: The N-terminal finger, epidermal growth factor, serine protease, Kringle 1, and Kringle 2 domain (Youchun et al. 2003). The active part of tPA, the thrombolytic Kringle 2 domain, serine protease domain, two functional regions of protease (176-527 amino acid residues), plus the 1 to 3 amino acids of the N-terminal is known as the "truncated human tissue plasminogen activator" (K2S, reteplase), which has a longer plasma half-life and higher fibrinolytic activity than tPA (Nordt and Bode 2003; Hidalgo et al. 2017). tPA can be manufactured using recombinant DNA technologies based on transgenic microorganism cultures such as *Escherichia coli* and *Saccharomyces cerevisiae* in fermentative bioreactors (Demain and Vaishnav 2009). The biotechnological production of recombinant tissue plasminogen activator protein (K2S, reteplase) from transplastomic tobacco cell cultures was also reported (Hidalgo et al. 2017).

Recombinant insulin protein is used as a treatment of diabetic patients. The recombinant protein is produced predominantly in *Escherichia* col and *Saccharomyces cerevisiae.*

There is a need to develop additional recombinant DNA technologies for the generation of low-cost biopharmaceutical proteins, without relying on animal systems, and without causing depletion of natural resources, pollution, or other environmental degradation. In this respect, a direct photosynthetic production of such compounds is promising. Recently, fusion constructs were designed as protein overexpression vectors that could be used in cyanobacteria for the over-expression of recalcitrant genes, e.g., plant terpene synthases (WO2016210154). In this approach, highly-expressed endogenous cyanobacteria genes, such as the cpcB gene, encoding the β-subunit of phycocyanin, or highly-expressed heterologous genes, such as the nptI gene, encoding the kanamycin resistance protein, were employed as leader sequences in such fusion constructs, resulting in the accumulation of eukaryotic proteins up to ~20% of the total cyanobacterial protein.

BRIEF SUMMARY OF SOME ASPECTS OF THE INVENTION

The present invention is based, in part on the discovery of fusion protein constructs that can be used in cyanobacteria as transgenic protein over-expression vectors to provide high levels of transgenic animal protein accumulation and thus provide high rates of production of biopharmaceutical products such as insulin, interferons, or tissue plasminogen activator (tPA), or tPA derivatives, e.g., an active truncated form of tPA.

In one aspect, provided herewith is an expression construct comprising a nucleic acid sequence comprising a transgene that encodes a biopharmaceutical protein, wherein the transgene is fused to the 3' end of a nucleic acid sequence that encodes a cyanobacteria protein that is expressed in cyanobacteria at a level of at least 1% of the total cellular protein or encodes an exogenous protein that is over-expressed in cyanobacteria at a level of at least 1% of the total cellular protein. In some embodiments, the transgene is fused to the 3' end of a nucleic acid sequence that encodes a cyanobacteria protein that is expressed in cyanobacteria at a level of at least 1% of the total cellular protein. In some embodiments, the cyanobacteria protein is a β-subunit of phycocyanin (cpcB), an α-subunit of phycocyanin (cpcA), a phycoerythrin subunit (cpeA or cpeB), an allophycocyanin subunit (apcA or apcB), a large subunit of Rubisco (rbcL), a small subunit of Rubisco (rbcS), a D1/32 kD reaction center protein (psbA) of photosystem-II, a D2/34 kD reaction center protein (psbD) of photosystem-II, a CP47 (psbB) or CP43 (psbC) reaction center protein of photosystem-II, a psaA or psaB reaction center protein of photosystem-I, a psaC or psaD reaction center protein of photosystem-I, an rpl ribosomal RNA protein, or an rps ribosomal RNA protein. In some embodiments, the transgene encode insulin, e.g., human insulin. In some embodiments the transgene encode an interferon, e.g., a human interferon alpha, such as IFNA2. In some embodiments, the transgene encodes a human tissue plasminogen activator, for example, a truncated human tissue plasminogen activator (K2S, reteplase), which includes the Kringle 2 domain and the serine protease domain. In some embodiments, the transgene encodes a SARS-CoV2 receptor binding domain. In other embodiments, the transgene encodes a a Tetanus Toxin Fragment C polypeptide. In some embodiments, the transgene is fused to the 3' end of a nucleic acid sequence that encodes an exogenous protein that is over-expressed in cyanobacteria at a level of at least 1% of the total cellular protein. For example, the exogenous protein may be an antibiotic resistance protein such as kanamycin, chloramphenicol, streptomycin, erythromycin, zeocin, or spectinomycin. In some embodiments, the transgene encode insulin, e.g., human insulin. In some embodiments the transgene encode an interferon, e.g., a human interferon alpha, such as IFNA2. In some embodiments, the transgene encodes a human tissue plasminogen activator, for example, a truncated human tissue plasminogen activator (K2S, reteplase), which includes the Kringle 2 domain and the serine protease domain. In some embodiments, the transgene encodes a SARS-CoV2 receptor binding domain. In other embodiments, the transgene encodes a a Tetanus Toxin Fragment C polypeptide.

In another aspect, the disclosure provide a host cell comprising an expression construct as described herein, e.g., in the preceeding paragraph. In some embodiments, the host cell is a cyanobacteria host cell, such as a single celled cyanobacteria, e.g., a *Synechococcus* sp., a *Thermosynechococcus elongatus*, a *Synechocystis* sp., or a Cyanothece sp. In some embodiments, the cyanobacteria are micro-colonial cyanobacteria, e.g., a *Gloeocapsa magma, Gloeocapsa phylum, Gloeocapsa alpicola, Gloeocapsa atrata, Chroococcus* spp., or *Aphanothece* sp. In some embodiments, the cyanobacteria is a filamentous cyanobacteria, such as an *Oscillatoria* spp., a *Nostoc* sp., an *Anabaena* sp., or an *Arthrospira* sp.

In further aspects, provided a cyanobacterial cell culture comprising cyanobacteria genetically modified as described herein to produce a biopharmaceutical protein, e.g., as described in the preceding paragraph. In some embodiments, the disclosure provide a photobioreactor containing such a cyanobacterial cell culture.

In an addition as expect, the disclosure provides a method of expressing a transgene at high levels, the method comprising culturing a cyanobacterial cell culture as described herein, e.g. in the preceding paragraph under conditions in which the transgene is expressed.

In a further aspect provided herein is a method of modifying a cyanobacterial cell to express a transgene at high levels, the method comprising introducing an expression construct as described herein, e.g., in the preceding paragraphs, into the cell.

In other aspective provided herein is an isolated fusion protein comprising a biopharmaceutical protein to be expressed in cyanobacteria fused to the 3' end of a heterologous protein that is expressed in cyanobacteria at a level of at least 1% of the total cellular protein. In some embodiments, the heterologous protein is a native cyanobacteria protein.

In a further aspect, provided herein is a cyanobacterial host cell comprising an expression unit comprising: (i) a nucleic acid sequence comprising a transgene that encodes a biopharmaceutical protein, wherein the transgene is fused to the 3' end of a nucleic acid sequence that encodes a cyanobacteria β-subunit of phycocyanin (cpcB) polypeptide to produce a fusion polypeptide comprises cpcB and the biopharmaceutical protein; (ii) a nucleic acid sequence encoding a cyanobacteria α-subunit of phycocyanin (cpcA) polypeptide; and (iii) a nucleic acid sequence encoding a cyanobacterial cpcC1, cpcC2 and cpcD polypeptide. In some embodiments, the recombinant expression unit is operably linked to an endogenous cyanobacteria cpc promoter. In some embodiments, the transgene encodes a native human interferon polypeptide. In some embodiments, the transgene encodes an interferon polypeptide having at least 95% identity to SEQ ID NO:1. In some embodiments, the fusion protein comprises a protease cleavage site, e.g., a Factor Xa cleavage site, between cpcB and the interferon polypeptide. In some embodiments, the transgene encodes a native human tissue plasminogen activator (tPA) polypeptide or truncated native human tPA polypeptide. In some embodiments, the transgene encodes a tPA polypeptide having at least 95% identity to the region of SEQ ID NO:2 that lacks the signal peptide or having at least 95% identity to SEQ ID NO:3. In some embodiments, the fusion protein comprises a protease cleavage site, e.g., a Factor Xa cleavage site, between cpcB and the tPA polypeptide. In some embodiments, the transgene encodes a native Tetanus Toxin Fragment C (TTFC) polypeptide or a TTFC polypeptide having at least 95% identity to SEQ ID NO:15. In some embodiments, the fusion protein comprises a protease cleavage site, e.g., a Tobacco Etch virus (TEV) cleavage site, between cpcB and the TTFC polypeptide. In some embodiments, the transgene encodes a native Cholera Toxin Fragment B polypeptide or a Cholera Toxin Fragment B polypeptide having at least 95% identity to SEQ ID NO:18. In some embodiments, the fusion protein comprises a protease cleavage site, e.g., a TEV cleavae site, between cpcB and the Cholera Toxin Fragment B polypeptide. In some embodiments, the transgene encodes a native human insulin polypeptide. In some embodiments, the transgene encodes an insulin polypeptide having at least 95% identity to SEQ ID NO:4. In some embodiments, the fusion protein comprises a protease cleavage site, e.g., a Factor Xa cleavage site, between the cpcB and insulin polypeptide. In some embodiments, the transgene encodes a SARS-CoV2 polypeptide having at least 95% identity to SEQ ID NO:16 or 17. In some embodiments, the fusion protein comprises a protease cleavage site between cpcB and the SARS-CoV2 polypeptide. In some embodiments, an expression unit as provided herein comprises an antibiotic resistance gene, e.g., a chloramphenicol or streptomycin antibiotic resistance gene, between the transgene and cpcA.

Lane 1 shows the cell extracts (upper panel) and the resin pellet (lower panel) of the wild type, CpcB*IFN, and CpcB*His*Xa*IFN fusion construct cells prior to incubation with the resin. Note the natural pink coloration of the latter.

Lane 2 shows the cell extracts (upper panel) and the resin pellet (lower panel) of the wild type, CpcB*IFN, and CpcB*His*Xa*IFN fusion construct cells following a 5-min incubation with the resin in the presence of 10 mM imidazole. Note the blue coloration of the resin and the green coloration of the supernatant.

Lanes 3-5 show the remaining cell extracts (upper panel) and the resin pellet (lower panel) of the wild type, CpcB*IFN, and CpcB*His*Xa*IFN fusion construct cells following a consecutive wash of the resin three times with a buffer containing 10 mM of imidazole. Note the resulting clear supernatant and the pink coloration of the resin after the third wash (lane 5) for the wild type and CpcB*IFN, suggesting absence of His-tagged proteins. Also note the blue coloration of the resin in the CpcB*His*Xa*IFN sample, which was retained in this pellet (lanes 3-5) in spite of the repeated wash, suggesting the presence of resin-bound blue-colored His-tagged proteins.

Lanes 6-8 show the subsequent extracts (upper panel) and the resin pellet (lower panel) of the wild type, CpcB*IFN, and CpcB*His*Xa*IFN fusion construct cells following a wash three times with a buffer containing 250 mM of imidazole, designed to dissociate His-tagged proteins from the resin. Note the bluish supernatant in lanes 6 and 7 and the corresponding loss of the blue color from the resin pellet, suggesting the specific removal of His-tagged proteins from the resin.

Figure 7:
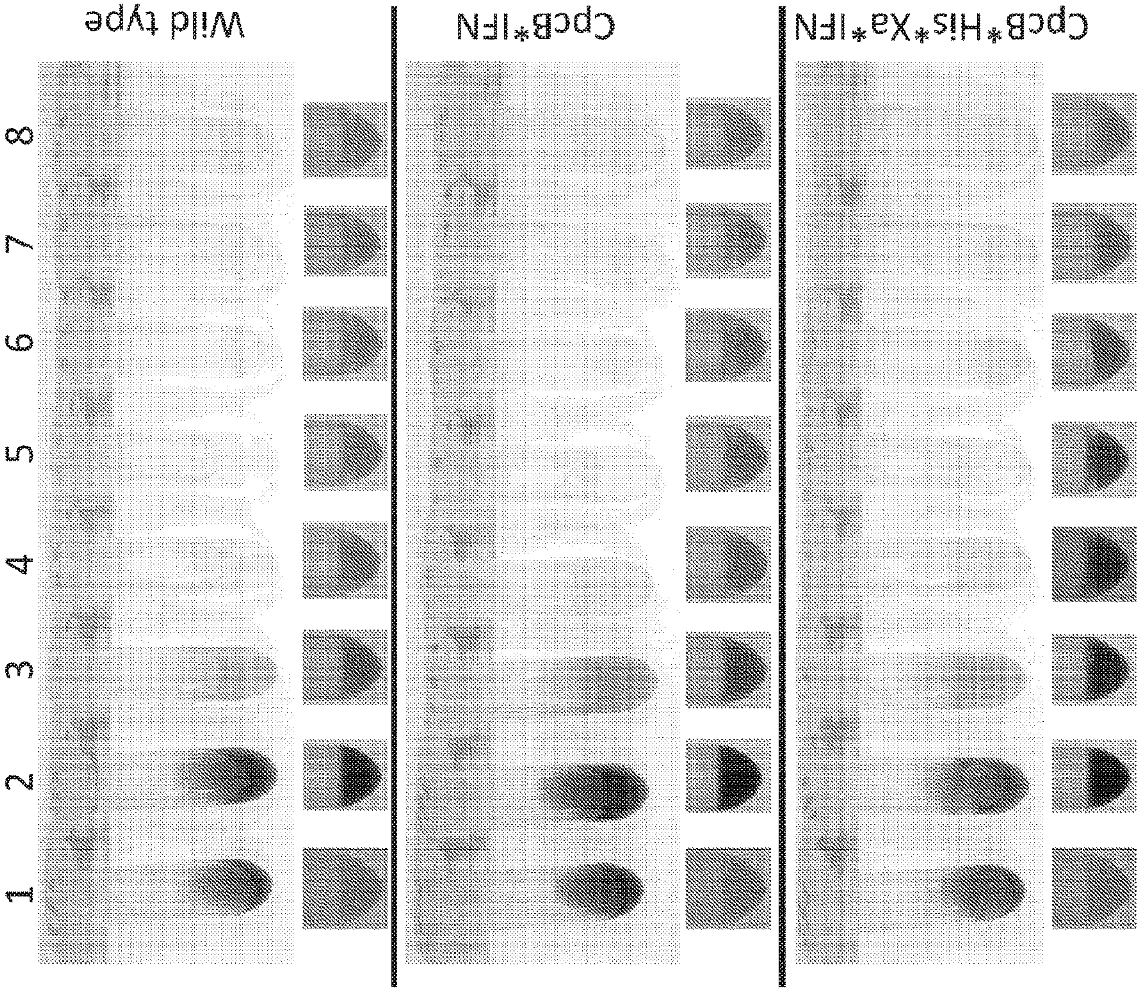
FIG. 7. Batch-scale purification of the recombinant CpcB*His*Xa*IFN protein through cobalt affinity chromatography. Protein purification was conducted employing a small amount of resin as solid phase. The latter was mixed and incubated with the cell extracts. The resin was pelleted and washed repeatedly with buffers containing imidazole at different concentrations.
Figure 8:
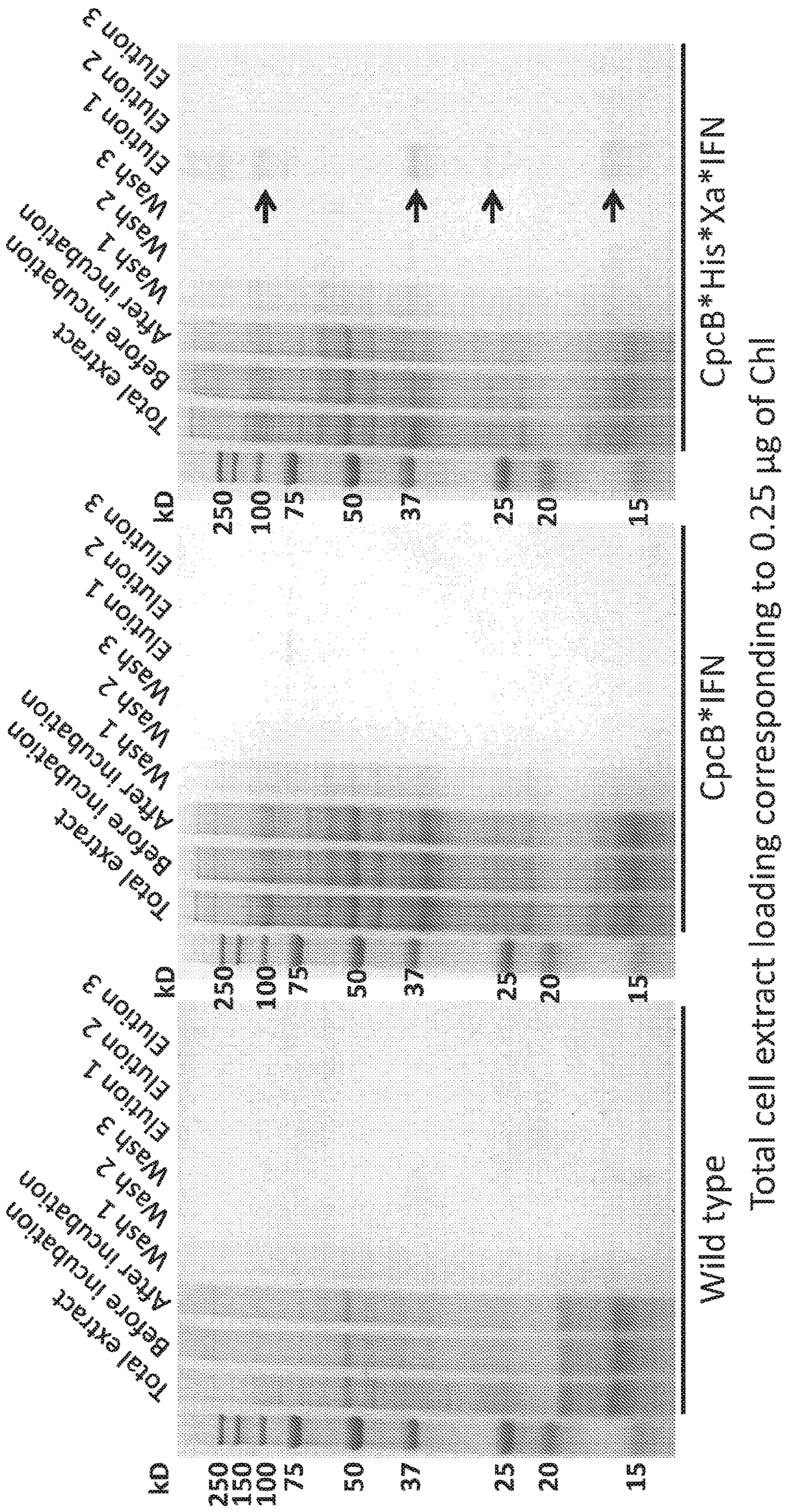

FIG. 8. Coomassie-stained SDS-PAGE gel analysis of fractions eluted with different imidazole concentrations. Fractions were obtained upon affinity chromatography purification as shown in FIG. 7. Samples were loaded on a per volume basis. Note the ~108, ~38, and ~17 kD proteins eluted from the CpcB*His*Xa*IFN extract (marked with arrows).

Figure 9:
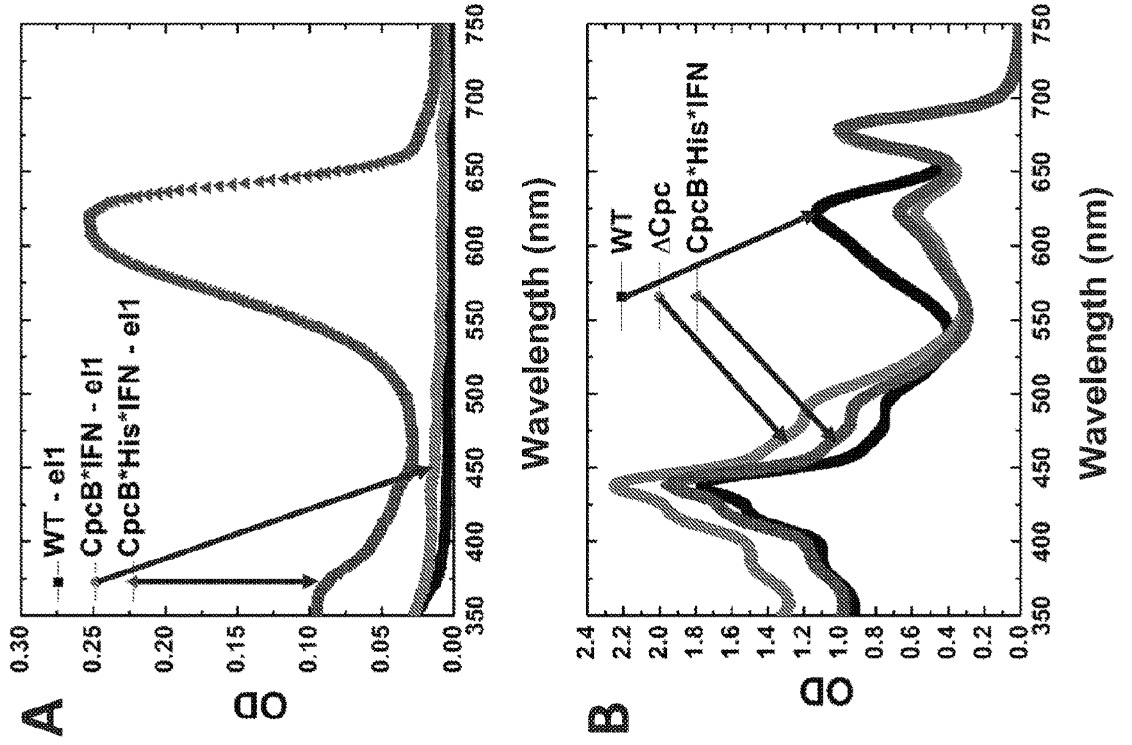

FIG. 9. Absorbance spectra of purified *Synechocystis* complexes. (A) Absorbance spectra of eluent E1 fractions from wild type, CpcB*IFN, and CpcB*His*Xa*IFN samples, as shown in FIG. 8. (B) Absorbance spectra of cellular protein extracts from wild type, Δcpc deletion mutant (Kirst et al., 2014) and CpcB*His*Xa*IFN transformant cells.

Figure 10:
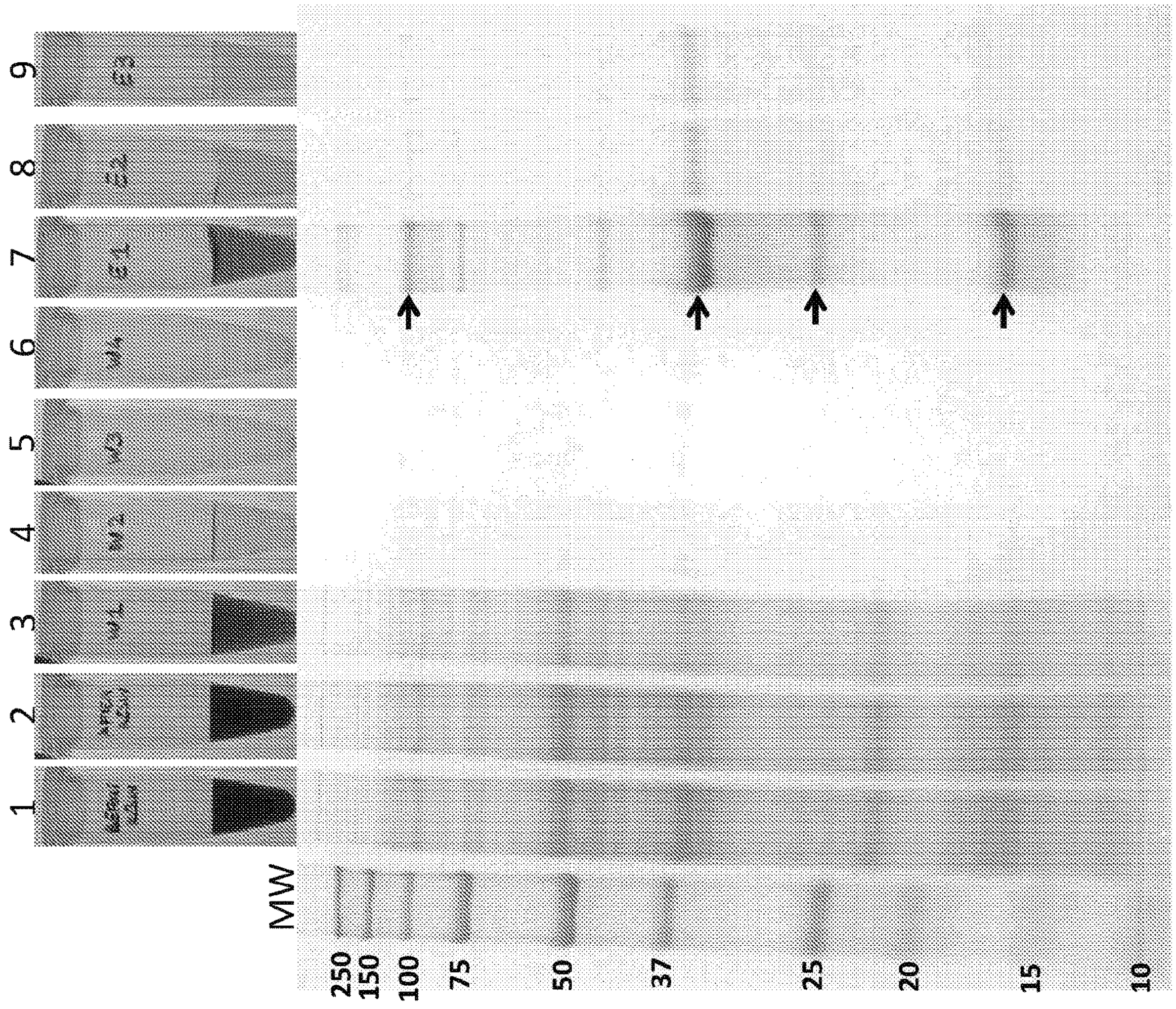

FIG. 10. Column-based purification of the CpcB*His*Xa*IFN fusion protein through cobalt affinity chromatography.

Lane 1, upper panel, shows the CpcB*His*Xa*IFN cell extracts in the presence of 5 mM imidazole prior to resin application. Lane 1, lower panel, shows the SDS-PAGE protein profile of these extracts, indicating presence of all *Synechocystis* proteins.

Lane 2, upper panel, shows the CpcB*His*Xa*IFN cell extracts after incubation with the resin but prior to washing with additional imidazole applications. Lane 2, lower panel, shows the SDS-PAGE protein profile of these extracts, obtained upon a prior removal of the resin from the mix, indicating presence of all *Synechocystis* proteins.

Lanes 3-6, upper panel, show the CpcB*His*Xa*IFN cell extracts that passed through the resin upon four consecutive washes with 5 mM imidazole and, lower panel, the SDS-PAGE protein profile of these extracts, showing a steep depletion (from lane 3 to lane 6) of total protein.

Lanes 7-9, upper panel, show the further removal of resin-bound proteins from the CpcB*His*Xa*IFN cell extracts that eluted upon three consecutive washes with 250 mM imidazole and, lower panel, the SDS-PAGE protein profile of these extracts, showing substantial enrichment in mainly four proteins with apparent molecular weights of 108, 36, 27, and 17 kD. The majority of these proteins were eluted with the first application of the 250 mM imidazole solution.

Figure 11:
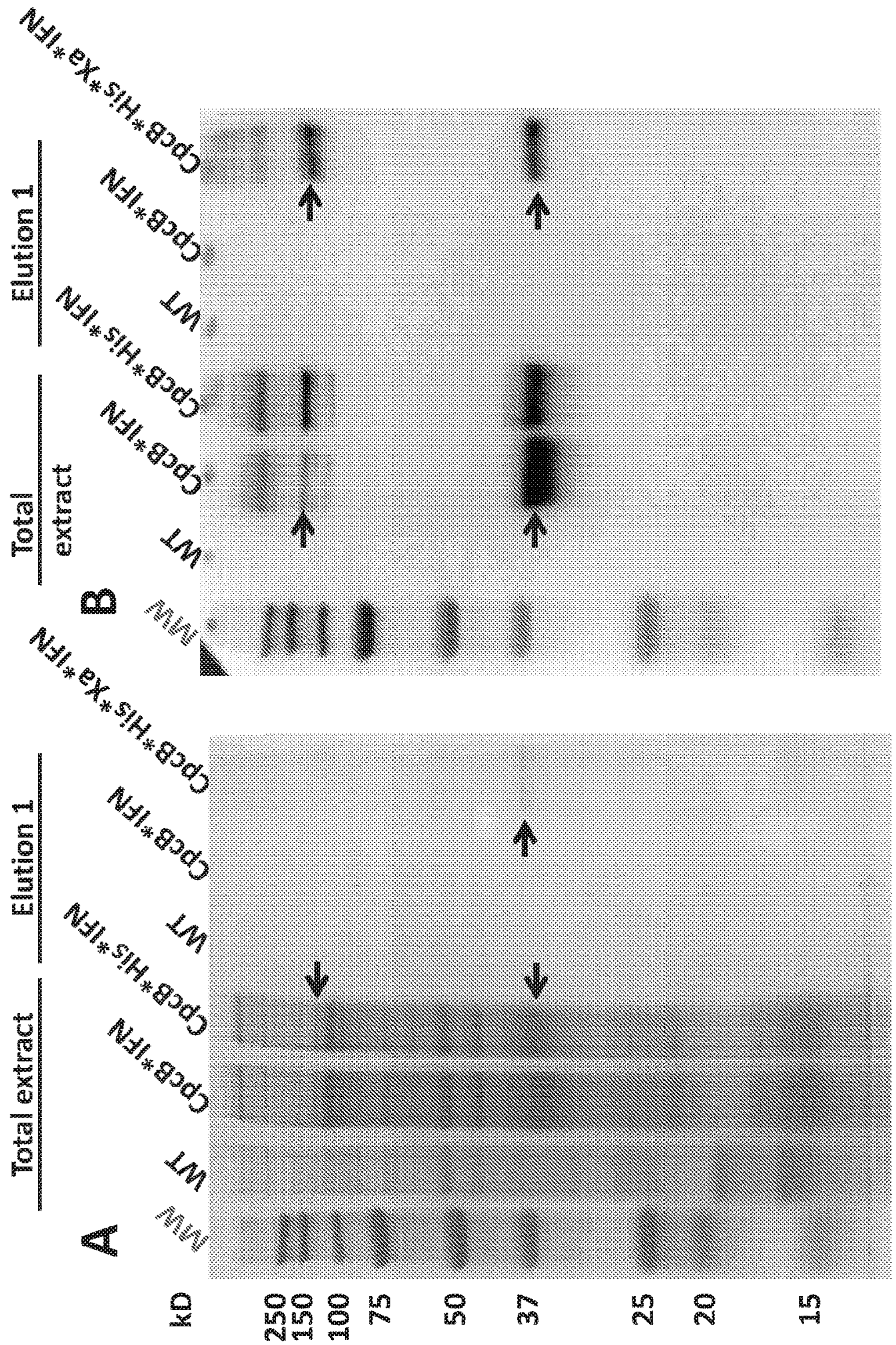

FIG. 11. (A) SDS-PAGE and Coomassie-staining analysis of *Synechocystis* wild type, CpcB*IFN, and CpcB*His*Xa*IFN total cell extract, and of proteins eluted from the resin column upon application of 250 mM imidazole. (B) Western blot analysis with specific IFN polyclonal antibodies of the proteins resolved in (A). Note the heterologous ~36 kD CpcB*His*Xa*IFN and the ~108 kD putative CpcB*His*Xa*IFN trimer (marked by arrowheads).

Figure 12:
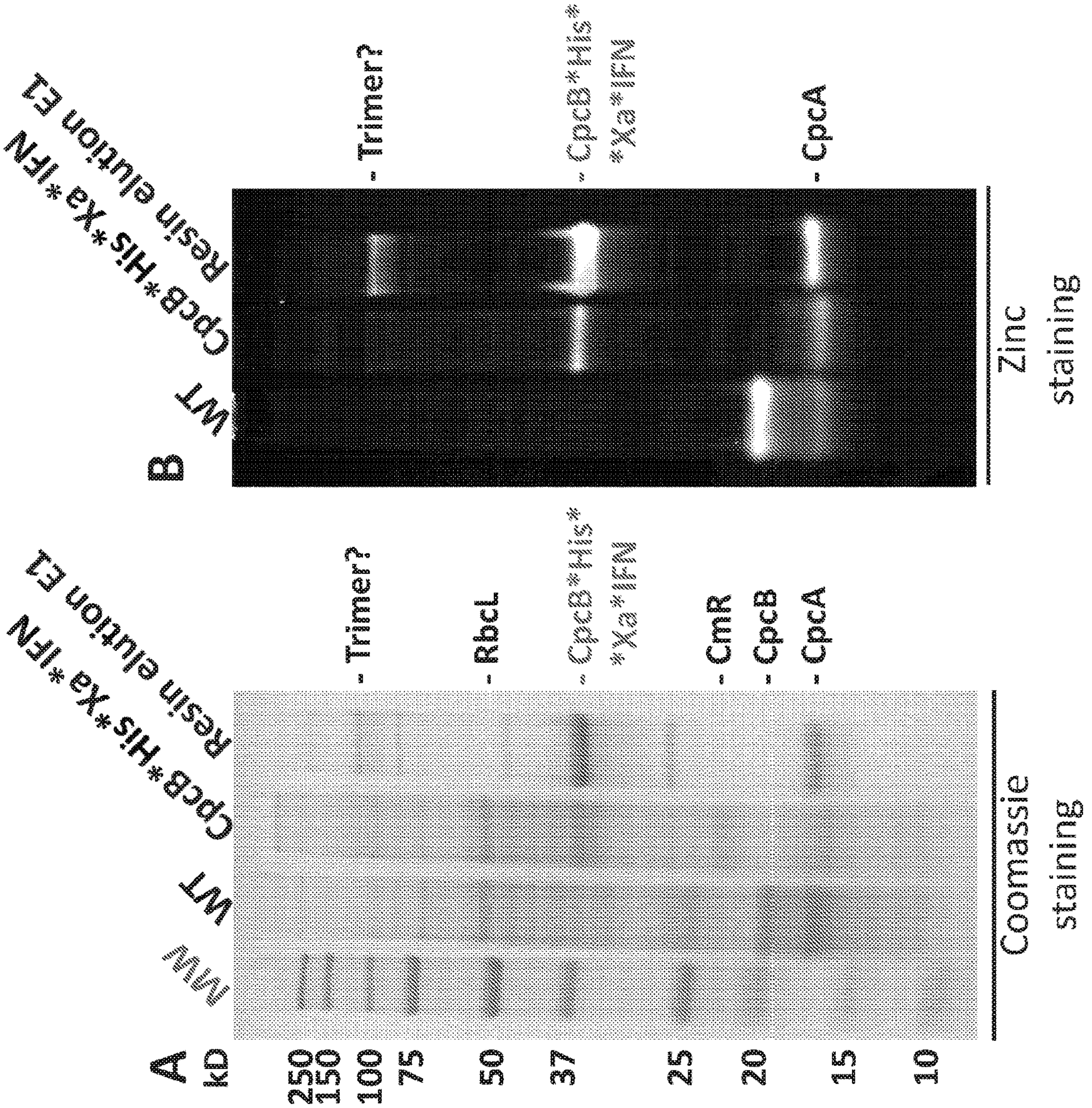

FIG. 12. (A) SDS-PAGE and Coomassie-stain analysis of *Synechocystis* wild type, CpcB*His*Xa*IFN, and resin-eluted proteins. (B) SDS-PAGE and Zinc-stain analysis of *Synechocystis* wild type, CpcB*His*Xa*IFN, and resin-eluted proteins. Zn-staining is designed to highlight the presence of bilin tetrapyrrole pigments. Individual native and heterologous proteins of interest are indicated to the right of the gels.

Figure 13:
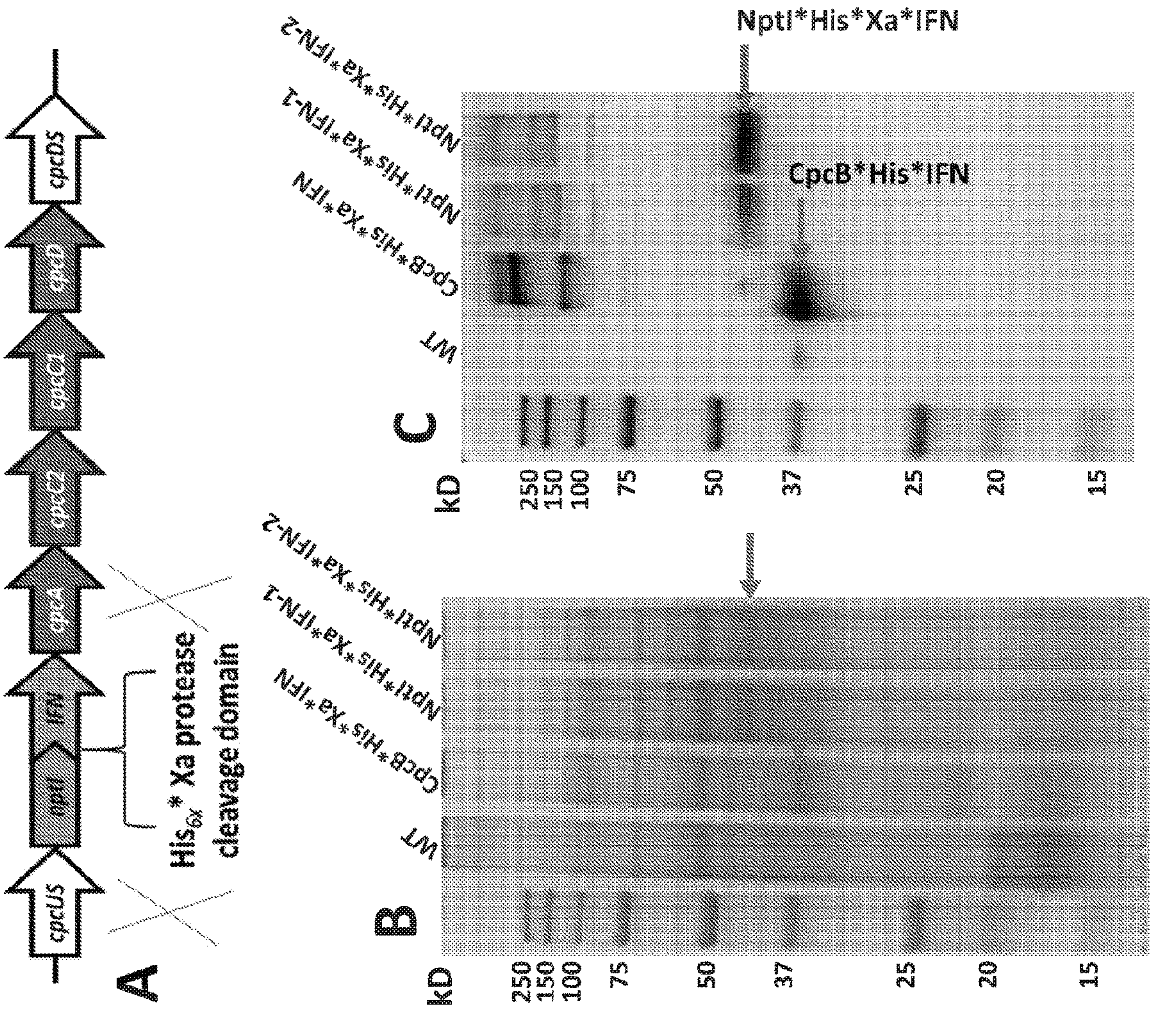

FIG. 13. (A) Map of the nptI*IFN fusion construct in the cpc operon locus. Note the presence of the His-tag and the Xa protease cleavage site in-between the two genes in the fusion. (B) SDS-PAGE and Coomassie staining of the protein extracts from wild type (WT), the cpcB*His*Xa*IFN, and two independent lines of the nptI*His*Xa*IFN transformants. (C) Western blot analysis of a duplicate gel as the one shown in (B). Specific anti-IFN polyclonal antibodies were used in this analysis. Note the specific antibody cross reactions with protein bands migrating to ~36 kD (CpcB*His*Xa*IFN) and ~46 kD (NptI*His*Xa*IFN). Also note the antibody cross reactions with protein bands of higher molecular mass.

Figure 14:
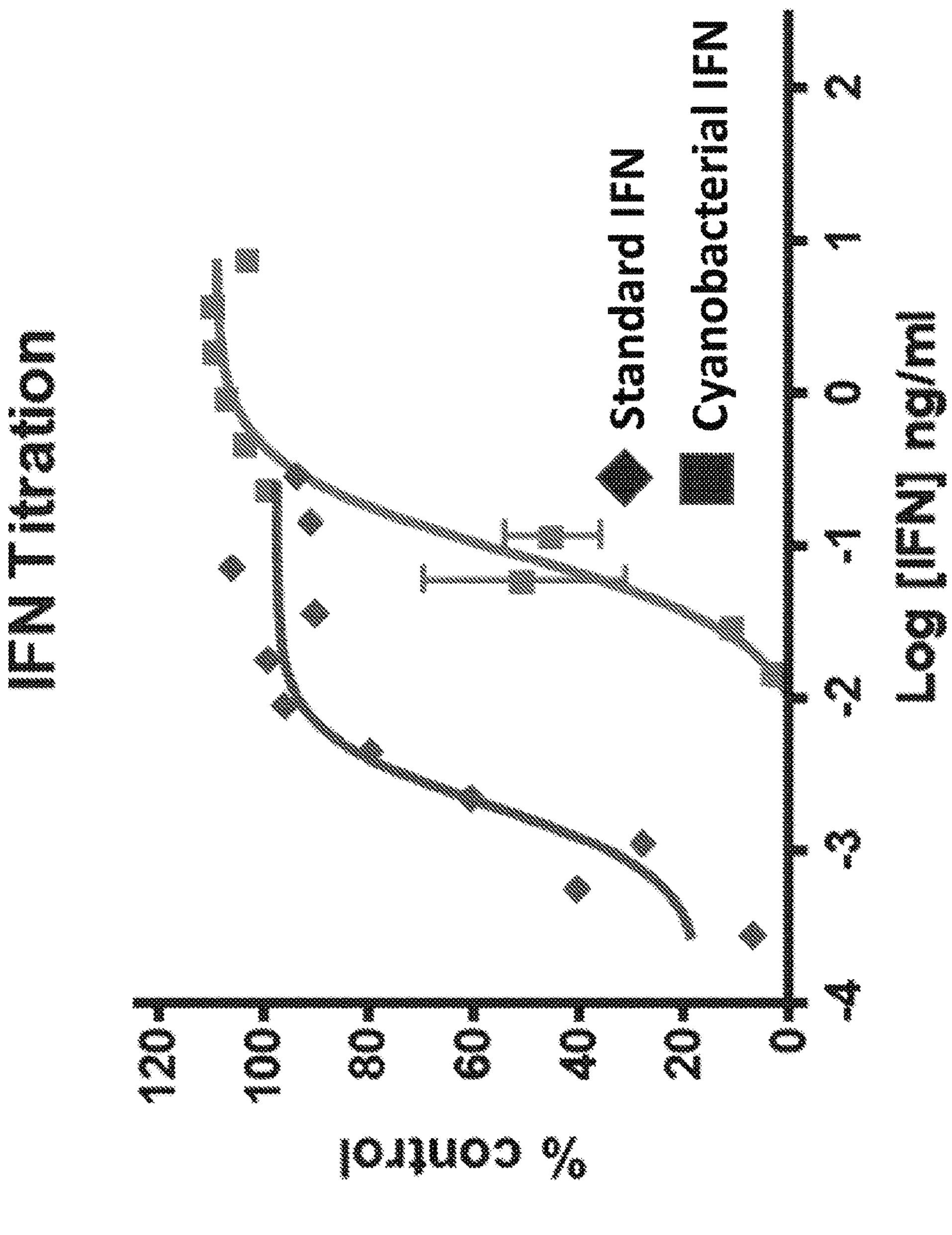

FIG. 14. Efficacy of interferon in preventing encephalomyocarditis virus (EMC) infection of human lung cells (A549), as performed by a PBL Assay Science, Piscataway, N.J. USA test. (Diamonds) IFN titration curve using a standard recombinant interferon. (Squares) IFN titration curve using the cyanobacterial CpcB*His*Xa*IFN fusion interferon. The analysis showed that 0.002 ng/mL of a standard recombinant interferon was needed to cause 50% inhibition in EMC infection, whereas 0.0875 ng/mL of cyanobacterial CpcB*His*Xa*IFN fusion interferon was required to cause 50% inhibition in EMC infection.

Figure 15:
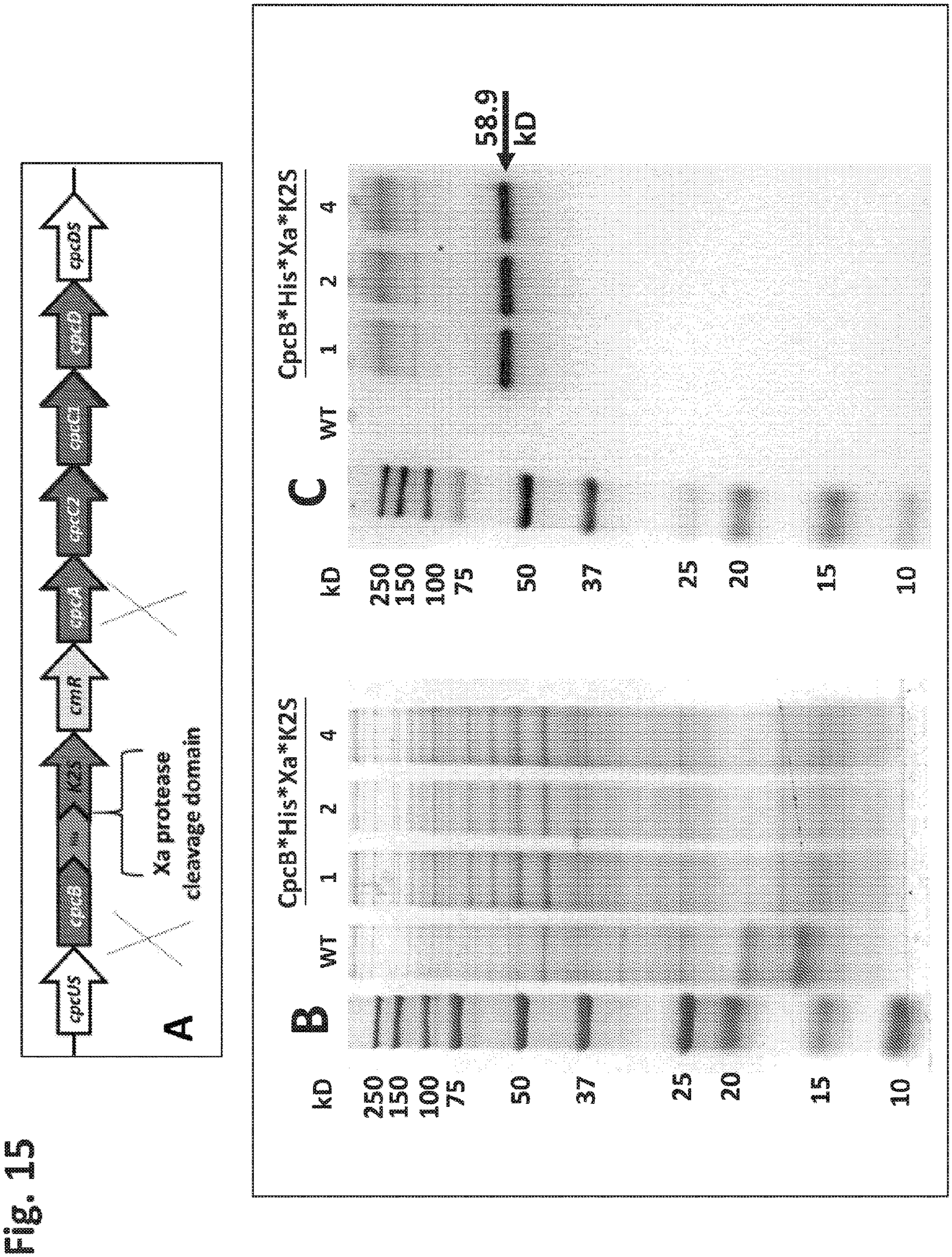

FIG. 15. (A) Map of the cpcB*His*Xa*K2S fusion construct in the cpc operon locus. Note the presence of the His-tag and the Xa protease cleavage site in-between the two genes in the fusion. (B) SDS-PAGE and Coomassie stain of the protein extracts from wild type (WT), and three independent lines of the cpcB*His*Xa*K2S transformant. (C) Western blot analysis of a duplicate gel as the one shown in (B). tissue-Plasminogen Activase recognizing polyclonal antibodies were used in this assay. Note the specific antibody cross reactions with protein bands migrating to ~58.9 kD protein band in the K2S transformants.

Figure 16:
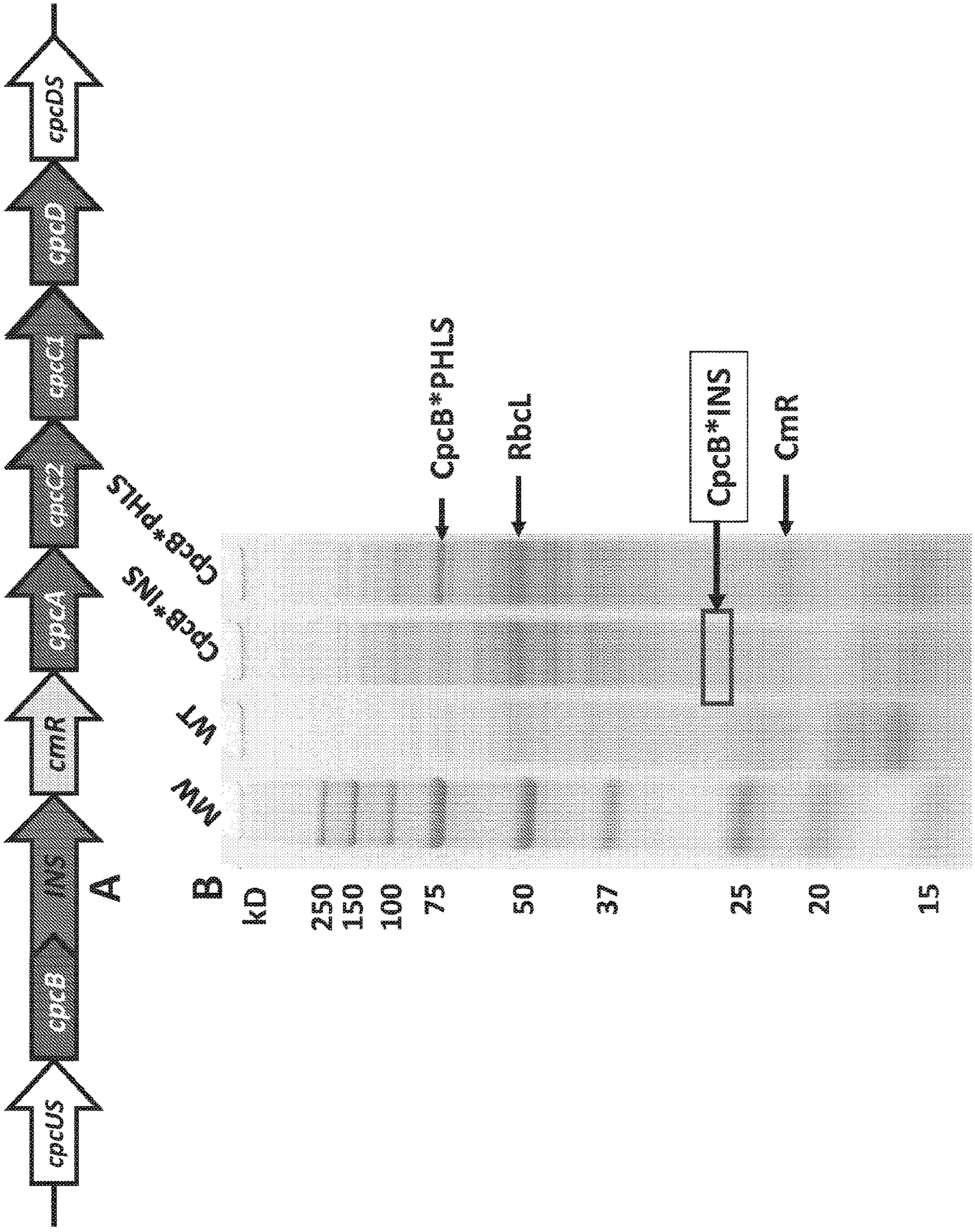

FIG. 16. (A) Map of the cpcB*INS fusion construct in the cpc operon locus. (B) SDS-PAGE and Coomassie stain of the protein extracts from wild type (WT), a CpcB*INS (insulin) containing transformant and, for comparison purposes, a CpcB*PHLS (β-phellandrene synthase) transformant. Note the 19 kD β-subunit and 17 kD α-subunit of phycocyanin in the wild type, the ~27 kD CpcB*INS (insulin) in the cpcB*INS transformant, and the ~84 kD CpcB*PHLS protein in the cpcB*PHLS transformant.

Figure 17:
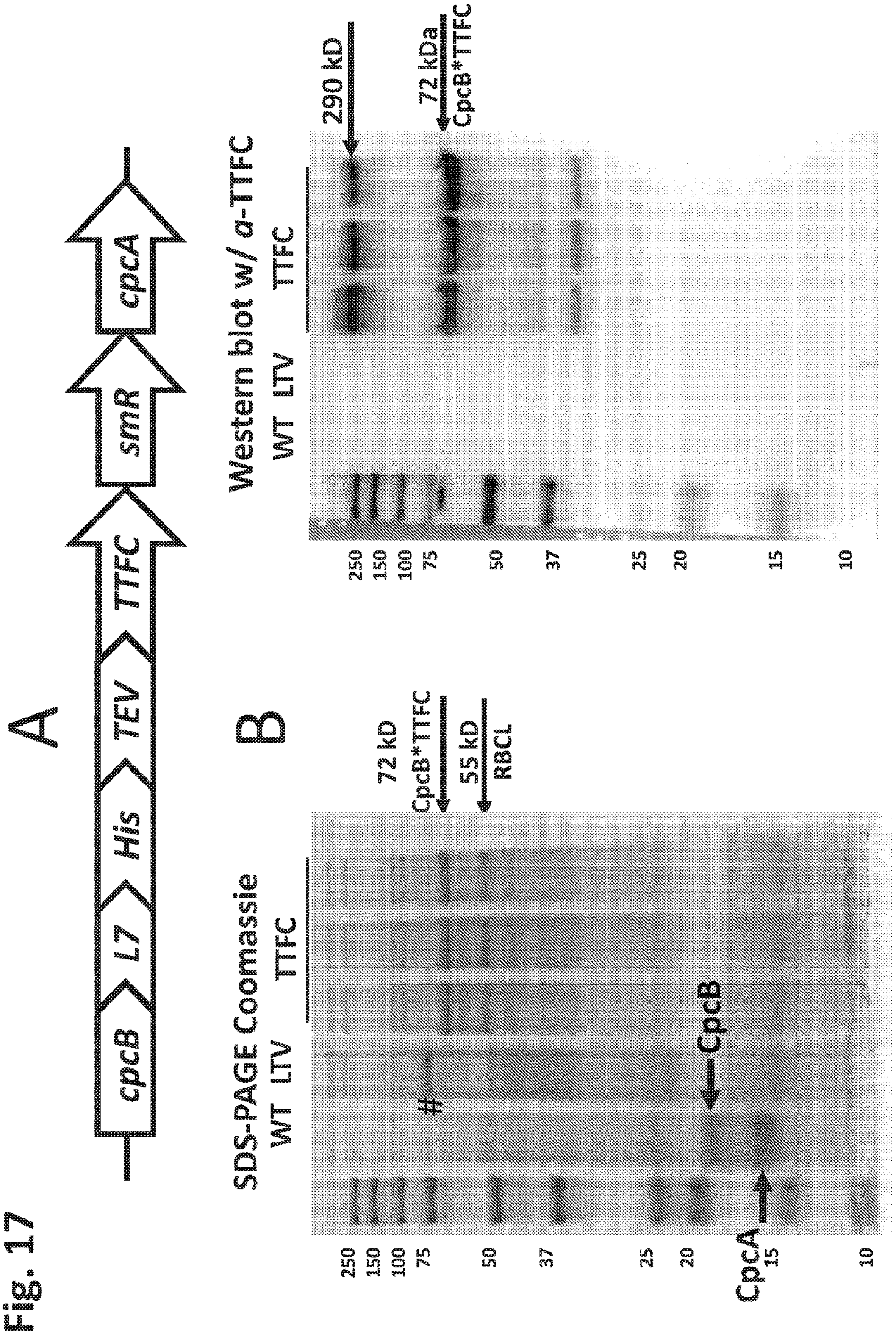

FIG. 17. (A) Map of the cpcB*L7*His*TEV*TTFC fusion construct in the cpc operon locus, including a linker of seven aminoacids (L7) and a His×6-tag (His). (B, left panel) SDS-PAGE and Coomassie stain analysis of the protein extracts from wild type (WT), the LTV recipient strain, and three *Synechocystis* transformant lines of the cpcB*L7*His*TEV*TTFC (Tetanus Toxin Fragment C). Note the presence of the 19 kD CpcB β-subunit and 17 kD CpcA α-subunit of phycocyanin in the wild type only, the ~72 kD cpcB*L7*His*TEV*TTFC protein (denoted as cpcB*TTFC) in the TTFC transformants, and the ~55 kD RBCL (large subunit of Rubisco) protein in all strains. Hashtag (#) denotes the electrophoretic mobility position of the cpcB*L7*TEV*ISPS fusion protein from the respective isoprene synthase (ISPS)-containing strain that was used as the recipient strain of the cpcB*L7*His*7EV*TTFC construct. Densitometric analysis of the SDS-PAGE Coomassie stain showed that the cpcB*L7*His*TEV*TTFC fusion protein accounted for about 28% of the total cell protein. (B, right panel) Western blot analysis of the protein profile shown in B (left panel), probed with specific polyclonal antibodies against the TTFC polypeptide. Note the antibody cross reaction with the 72 kD CpcB*L7*His*TEV*TTFC fusion protein, the ~290 kD putative trimeric [CpcB*L7*His*TEV*TTFC]×3 undissolved fusion protein complex, plus some lower molecular size putative proteolysis fragments.

Figure 18:
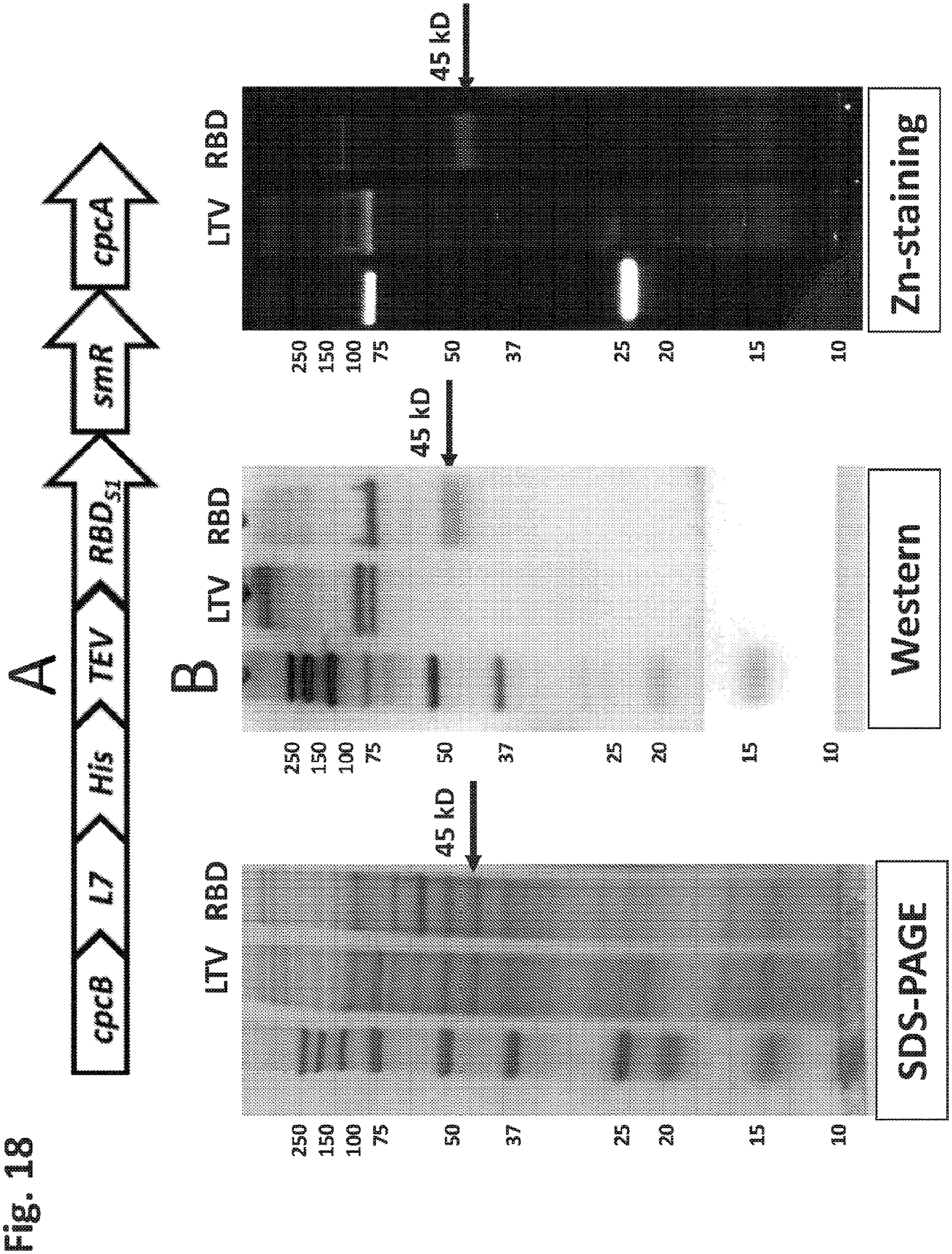

FIG. 18. (A) Map of the cpcB*L7*His*TEV*RBD fusion construct in the cpc operon locus, including a linker of seven amino acids (L7), a His×6-tag (His) and the TEV cleavage site (TEV), followed by the Receptor Binding Domain (RBD) of the S1 protein from the SARS-CoV-2. (B, left panel) SDS-PAGE and Coomassie stain of the protein extracts from wild type (WT), the LTV recipient strain, and a *Synechocystis* transformant line harboring the cpcB*L7*His*TEV*RBD fusion protein (RBD). The arrow points to the electrophoretic mobility of the 45 kD RBD fusion protein. (B, center panel). Western blot analysis of the protein profile shown in B (left panel), probed with specific polyclonal antibodies against the leader CpcB protein in the fusion construct. Note the antibody cross reaction with the 45 kD cpcB*L7*His*TEV*RBD fusion protein. (B, right panel) SDS-PAGE and Zinc-stain analysis of *Synechocystis* expressing the LTV and RBD fusion construct phenotypes. Zn-staining is designed to highlight the presence of bilin tetrapyrrole pigments. Note the Zn-staining of a band at 45 kD in the RBD expressing transformant, and the staining of a band migrating to ~85 kD in the LTV (cpcB*L7*REV*ISPS) transformant.

Figure 19:
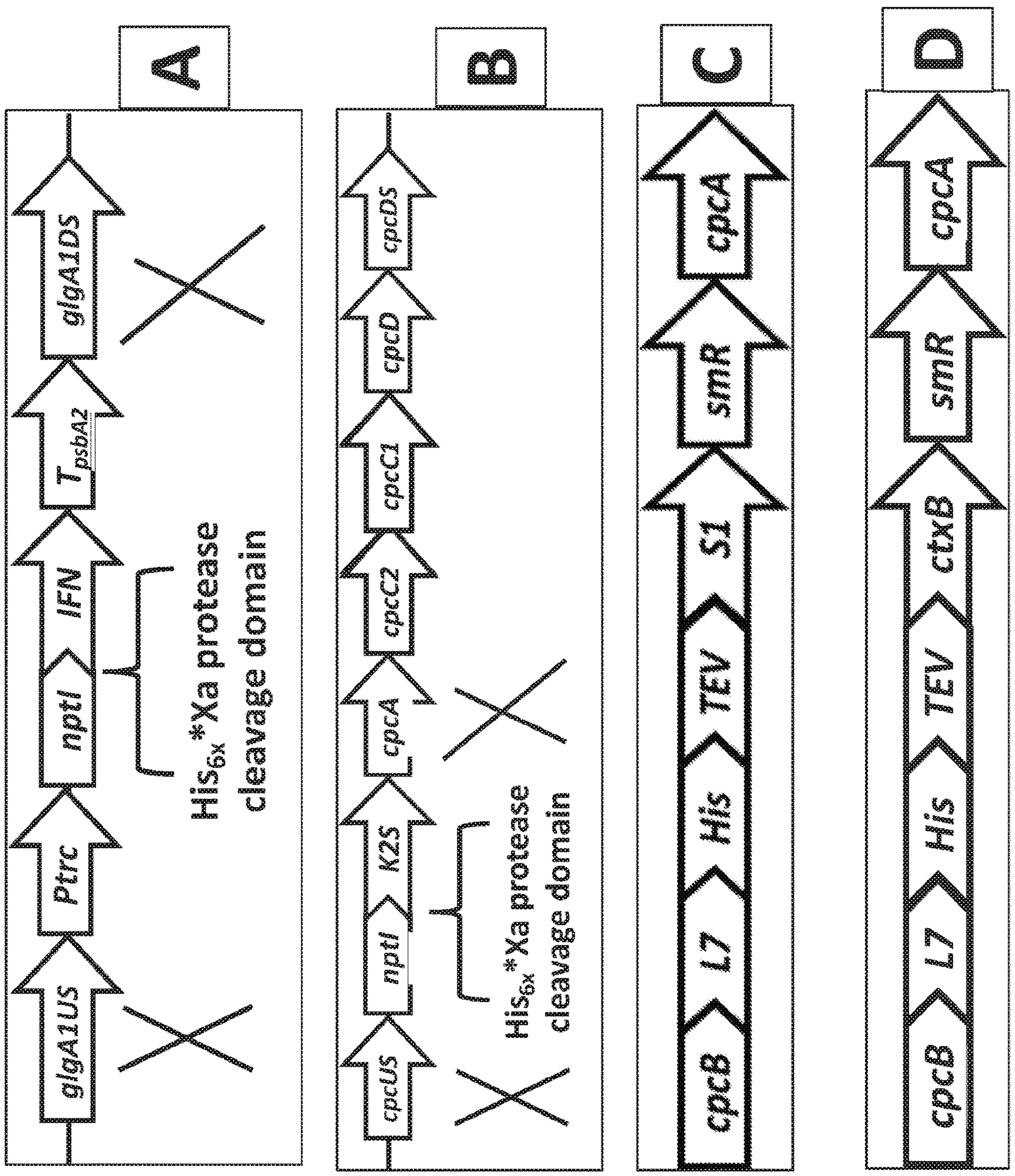

FIG. 19. Panels A-D provide schematics of illustrative expression constructs.

DETAILED DESCRIPTION OF THE INVENTION

The term "naturally-occurring" or "native" as used herein as applied to a nucleic acid, a protein, a cell, or an organism, refers to a nucleic acid, protein, cell, or organism that is found in nature. For example, a polypeptide or polynucleotide sequence that is present in an organism that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell. In some embodiments, a "heterologous" nucleic acid may comprise a nucleotide sequence that differs in sequence from the endogenous nucleotide sequence but encodes the same protein (having the same amino acid sequence) as found endogenously; or two or more nucleotide sequences that are not found in the same relationship to each other in nature, e.g., the nucleic acid is recombinant. An example of a heterologous nucleic acid is a nucleotide sequence encoding a fusion protein comprising two proteins that are not joined to one another in nature.

The term "recombinant" polynucleotide or nucleic acid refers to one that is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. A "recombinant" protein is encoded by a recombinant polynucleotide. In the context of a genetically modified host cell, a "recombinant" host cell refers to both the original cell and its progeny.

As used herein, the term "genetically modified" refers to any change in the endogenous genome of a cyanobacteria cell compared to a wild-type cell. Thus, changes that are introduced through recombinant DNA technology and/or classical mutagenesis techniques are both encompassed by this term. The changes may involve protein coding sequences or non-protein coding sequences such as regulatory sequences as promoters or enhancers.

An "expression construct" or "expression cassette" as used herein refers to a recombinant nucleic acid construct, which, when introduced into a cyanobacterial host cell in accordance with the present invention, results in increased expression of a fusion protein encoded by the nucleic acid construct. The expression construct may comprise a promoter sequence operably linked to a nucleic acid sequence encoding the fusion protein or the expression cassette may comprise the nucleic acid sequence encoding the fusion protein where the construct is configured to be inserted into a location in a cyanobacterial genome such that a promoter endogenous to the cyanobacterial host cell is employed to drive expression of the fusion protein. An "expression unit" as used herein refers to a minimal region of a polynucleotide that is expressed that provided for high level protein expression, which comprises the polynucleotide that encodes the fusion protein, as well as other genes, e.g., cpcA and cpc operon genes encoding cpc linker polypeptides CpcC2, CpcC1, and CpcD. In some embodiments, the expression unit additionally include a gene encoding an antibiotic resistance polypeptide, such as a chloramphenicol resistance gene or streptomycin resistance gene. The expression unit may also comprise additional sequences, such as nucleic acid sequences encoding a protease cleavage sites, a linker polypeptide, or a polypeptide tagging sequence, such as a His tag.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous protein" refers to a protein that is not normally or naturally found in and/or produced by a given cyanobacterium, organism, or cell in nature. As used herein, the term "endogenous protein" refers to a protein that is normally found in and/or produced by a given cyanobacterium, organism, or cell in nature.

An "endogenous" protein or "endogenous" nucleic acid is also referred to as a "native" protein or nucleic acid that is found in a cell or organism in nature.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" may include both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "promoter" or "regulatory element" refers to a region or sequence determinants located upstream or downstream from the start of transcription that are involved in recognition and binding of RNA polymerase and other proteins to initiate transcription. A "cyanobacteria promoter" is a promoter capable of initiating transcription in cyanobacteria cells. Such promoters need not be of cyanobacterial origin, for example, promoters derived from other bacteria or plant viruses, can be used in the present invention.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch. *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" in the context of polynucleotide or polypeptide sequences means that a polynucleotide or polypeptide comprises a sequence that has at least 50% sequence identity to a reference nucleic acid or polypeptide sequence. Alternatively, percent identity can be any integer from 40% to 100%. Exemplary embodiments include at least: 50%, 55%, 60%, 65%, 70%, 75%, 80%, 85%, 90%, 95%, or 99% compared to a reference sequence using the programs described herein; preferably BLAST using standard parameters, as described below.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high-performance liquid chromatography. A protein which is the predominant species present in a preparation is substantially purified. In particular, an isolated gene is separated from open reading frames which flank the gene and encode a protein other than the gene of interest.

The term "reactor" as used herein refers to the vessel in which cyanobacteria are grown.

Introduction

The present invention is based, in part, on the discovery of fusion protein constructs that can be used in cyanobacteria as transgenic protein over-expression vectors to provide high levels of transgenic animal proteins, e.g., interferons, insulin, or tPA polypeptides. Expression of transgenes in cyanobacteria using such vectors results in high levels of accumulation of a protein encoded by the transgene.

A fusion protein of the present invention comprises a protein that is to be expressed in cyanobacteria, typically a non-native protein that is not expressed in cyanobacteria, e.g., a plant protein fused to a protein that is expressed at high levels in cyanobacteria. In the context of the present invention, a protein that is "expressed at high levels in cyanobacteria" refers to a protein that accumulates to at least 1%. Such proteins, when fused at the N-terminus of a protein of interest to be expressed in cyanobacteria, are also referred to herein as "leader proteins", "leader peptides", or "leader sequences". A nucleic acid encoding a leader protein is typically referred to herein as a "leader polynucleotide" or "leader nucleic acid sequence" or "leader nucleotide sequence".

In some embodiments, a protein that is expressed at high levels is a naturally occurring protein that is expressed at high levels in wild-type cyanobacteria, and is used as endogenous "leader polypeptide sequence" in the cyanobacterial strain of origin. Such proteins include, e.g., a phycocyanin β-subunit (cpcB), a phycocyanin α-subunit (cpcA), a phycoerythrin α-subunit (cpeA), a phycoerythrin β-subunit (cpeB), an allophycocyanin α-subunit (apcA), an allophycocyanin β-subunit (apcB), a large subunit of Rubisco (rbcL), a small subunit of Rubisco (rbcS), a photosystem II reaction center protein, a photosystem 1 reaction center protein, or a rpl or rps cyanobacterial ribosomal RNA protein. In some embodiments, a protein that is expressed at high levels is a naturally occurring protein that is expressed at high levels in wild-type cyanobacteria, and it is used as heterologous leader sequence in a different cyanobacterial strain.

In some embodiments, a protein that is expressed at high levels is an exogenous protein that the cyanobacteria have been genetically modified to express at high levels. For example, proteins that provide for antibiotic resistance that are expressed to high levels in cyanobacteria, e.g., a bacterial kanamycin resistance protein, NPT, or a bacterial chloramphenicol resistance protein, CmR, may be used as a leader sequence.

The invention additionally provides nucleic acids encoding a fusion protein as described herein, as well as expression constructs comprising the nucleic acids and host cells that have been genetically modified to express such fusion proteins. In further aspects, the invention provides methods of modifying a cyanobacterial cell to overexpress a protein of interest using an expression construct of the invention and methods of producing the protein of interests and products generated by the proteins using such genetically modified cyanobacterial cells.

The invention employs various routine recombinant nucleic acid techniques. Generally, the nomenclature and the laboratory procedures in recombinant DNA technology described below are those commonly employed in the art. Many manuals that provide direction for performing recombinant DNA manipulations are available, e.g., Sambrook, Molecular Cloning, A Laboratory Manual (4th Ed, 2012); and Current Protocols in Molecular Biology (Ausubel et al., eds., 1994-2015).

Proteins Expressed at High Levels in Cyanobacteria

In the present invention, nucleic acid constructs are created in which a polynucleotide sequence encoding a protein of interest is fused to the C-terminal end of a polynucleotide that encodes a leader protein, i.e., a protein that is expressed at high levels in cyanobacteria as described herein. The protein of interest is then also expressed at high levels in conjunction with the leader sequence. In the context of the invention, a protein that is "expressed at high levels" in cyanobacteria refers to a protein that is at least 1%, typically at least 2%, at least 3%, at least 4%, at least 5%, or at least 10%, or greater, of the total protein expressed in the cyanobacteria. Expression levels in cyanobacteria may be evaluated in cells that are logarithmically growing, but may be alternatively determined in cells in a stationary phase of growth. The level of protein expression can be assessed using various techniques. In the present invention, high level expression is typically determined using SDS PAGE analysis. Following electrophoresis, the gel is stained and the level of proteins assessed by scanning the gel and quantifying the amount of protein using an image analyzer.

In some embodiments, a leader sequence in accordance with the invention encodes a naturally occurring cyanobacteria protein that is expressed at high levels in native cyanobacteria. Thus, in some embodiments, the protein is endogenous to cyanobacteria. Examples of such proteins include cpcB, cpcA, cpeA, cpeB, apcA, apcB, rbcL, rbcS, psbA, rpl, or rps. In some embodiments, the leader sequence encodes less than the full-length of the protein, but typically comprises a region that encodes at least 25%, typically at least 50%, or at least 75%, or at least 90%, or at least 95%, or greater, of the length of the protein. As appreciated by one of skill in the art, use of an endogenous cyanobacterial polynucleotide sequence for constructing an expression construct in accordance with the invention provides a sequence that need not be codon-optimized, as the sequence is already expressed at high levels in cyanobacteria. Examples of cyanobacterial polynucleotides that encode cpcB, cpcA, cpeA, cpeB, apcA, apcB, rbcL, rbcS, psbA, rpl, or rps are available at the website www.genome.microbedb.jp/cyanobase under accession numbers, as follows:

- cpcA: *Synechocystis* sp. PCC6803 sll1578, *Anabaena* sp. PCC7120 arl0529, *Thermosynechococcus elongatus* BP-1 tlr1958, *Synechococcus elongatus* PCC6301 syc0495_c, syc0500_c
- cpcB: *Synechocystis* sp. PCC6803 sll1577, *Anabaena* sp. PCC7120 arl0528, *Thermosynechococcus elongatus* BP-1 tlr1957, *Synechococcus elongatus* PCC6301 syc0496_c, syc0501_c
- cpeA: *Prochlorococcus marinus* SS120 Pro0337, *Synechococcus* sp. WH8102 SYNW2009, SYNW2016
- cpeB: *Prochlorococcus marinus* SS120 Pro0338, *Synechococcus* sp. WH8102 SYNW2008, SYNW2017
- apcA: *Synechocystis* sp. PCC 6803, slr2067: *Anabaena* sp. PCC 7120, all0450, alr0021; *Synechococcus elongatus* PCC 6301, syc1186_d
- apcB: *Synechocystis* sp. PCC 6803, slr1986, *Anabaena* sp. PCC 7120, alr0022, *Synechococcus elongatus* PCC 6301, syc1187_d
- rbcL RubisCO large subunit: *Synechocystis* sp. PCC 6803 slr0009
- rbcS RubisCO small subunit: *Synechocystis* sp. PCC 6803 slr0012
- rpl: 50S ribosomal protein of *Synechocystis*, e.g. sll1803; sll1810; ssr1398 and
- rps: 30S ribosomal protein of *Synechocystis*, e.g. sll1804; slr1984.

The polynucleotide sequence that encodes the leader protein need not be 100% identical to a native cyanobacteria polynucleotide sequence. A polynucleotide variant having at least 50% identity or at least 60% identity, or greater, to a native cyanobacterial polynucleotide sequence, e.g., a native cpcB, cpcA, cpeA, cpeB, rbcL, rbcS, psbA, rpl, or rps cyanobacteria polynucleotide sequence, may also be used, so long as the codons that vary relative to the native cyanobacterial polynucleotide are codon optimized for expression in cyanobacteria and the codons that vary relative to the wild type sequence do not substantially disrupt the structure of the protein. In some embodiments, a polynucleotide variant that has at least 70% identity, at least 75% identity, at least 80% identity, or at least 85% identity, or greater to a native cyanobacterial polynucleotide sequence, e.g., a native cpcB, cpcA, cpeA, cpeB, rbcL, rbcS, psbA, rpl, or rps cyanobacteria polynucleotide sequence, is used, again maintaining codon optimization for cyanobacteria. In some embodiments, a polynucleotide variant that has least 90% identity, or at least 95% identity, or greater, to a native cyanobacterial polynucleotide sequence, e.g., a native cpcB, cpcA, cpeA, cpeB, rbcL, rbcS, psbA, rpl, or rps cyanobacteria polynucleotide sequence, is used. The percent identity is typically determined with reference the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. The protein encoded by a variant polynucleotide sequence as described need not retain a biological function, however, a codon that varies from the wild-type polynucleotide is typically selected such that the protein structure of the native cyanobacterial sequence is not substantially altered by the changed codon, e.g., a codon that encodes an amino acid that has the same charge, polarity, and/or is similar in size to the native amino acid is selected.

In some embodiments, a polynucleotide variant of a naturally over-expressed (more than 1% of the total cellular protein) cyanobacterial gene is employed, that encodes for a polypeptide sequence that has at least 70%, or 80%, or at least 85% or greater identity to the protein encoded by the wild-type gene. In some embodiments, the polynucleotide encodes a protein that has 90% identity, or at least 95% identity, or greater, to the protein encoded by the wild-type gene. Variant polynucleotides may also be codon optimized for expression in cyanobacteria.

In some embodiments, a protein that is expressed at high levels in cyanobacteria is not native to cyanobacteria in which a fusion construct in accordance with the invention is expressed. For example, polynucleotides from bacteria or other organisms that are expressed at high levels in cyanobacteria may be used as leader sequences. In some embodiments, the polynucleotides from other organisms may be codon-optimized for expression in cyanobacteria. In some embodiments, codon optimization is performed such that codons used with an average frequency of less than 12% by *Synechocystis* are replaced by more frequently used codons. Rare codons can be defined, e.g., by using a codon usage table derived from the sequenced genome of the host cyanobacterial cell. See, e.g., the codon usage table obtained from Kazusa DNA Research Institute, Japan (website wwtw.kazusa.or.jp/codon/) used in conjunction with software, e.g., "Gene Designer 2.0" software, from DNA 2.0 (website www.dna20.com/) at a cut-off thread of 15%.

In some embodiments, a leader sequence in accordance with the present invention encodes a protein that confers antibiotic resistance. For example, in some embodiments, the leader sequence encodes neomycin phosphotransferase e.g., NPT1, which confers neomycin and kanamycin resistance. Other polynucleotides that may be employed include a chloramphenicol acetyltransferase polynucleotide, which confers chloramphenicol resistance; or a polynucleotide encoding a protein that confers streptomycin, ampicillin, erythromycin, zeocin, or tetracycline resistance, or resistance to another antibiotic. In some embodiments, the leader sequence encodes less than the full-length of the protein, but typically comprises a region that encodes at least 25%, typically at least 50%, or at least 75%, or at least 90%, or at least 95%, or greater, of the length of the protein. In some embodiments, a polynucleotide variant of a naturally occurring antibiotic resistance gene is employed. As noted above, a variant polynucleotide need not encode a protein that retains the native biological function. A variant polynucleotide typically encodes a protein that has at least 80% identity, or at least 85% or greater, identity to the protein encoded by the wild-type antibiotic resistance gene. In some embodiments, the polynucleotide encodes a protein that has 90% identity, or at least 95% identity, or greater, to the wild-type antibiotic resistance protein. Such variant polynucleotides employed as leader sequence may also be codon-optimized for expression in cyanobacteria. The percent identity is typically determined with reference to the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. A protein encoded by a variant polynucleotide sequence need not retain a biological function, however, codons that are present in a variant polynucleotide are typically selected such that the protein structure relative to the wild-type protein structure is not substantially altered by the changed codon, e.g., a codon that encodes an amino acid that has the same charge, polarity, and/or is similar in size to the native amino acid is selected.

Other leader proteins can be identified by evaluating the level of expression of a candidate leader protein in cyanobacteria. For example, a leader polypeptide that does not occur in wild type cyanobacteria may be identified by measuring the level of protein expressed from a polynucleotide codon optimized for expression in cyanobacteria that encodes the candidate leader polypeptide. A protein may be selected for use as a leader polypeptide if the protein accumulates to a level of at least 1%, typically at least 2%, at least 3%, at least 4%, at least 5%, or at least 10%, or greater, of the total protein expressed in the cyanobacteria when the polynucleotide encoding the leader polypeptide is introduced into cyanobacteria and the cyanobacteria cultured under conditions in which the transgene is expressed. The level of protein expression is typically determined using SDS PAGE analysis. Following electrophoresis, the gel is scanned and the amount of protein determined by image analysis.

Transgenes

A fusion construct of the invention may be employed to provide high level expression in cyanobacteria for any desired biopharmaceutical protein. Thus, for example, cyanobacteria can be engineered to express an animal biopharmaceutical polypeptide such as an antibody, hormone, cytokine, therapeutic enzyme and the like, as a fusion polypeptide with a protein expressed at a high level in cyanobacteria, e.g. a cpcB or other protein encoded by the Cpc operon. In some embodiments the biopharmaceutical polypeptide is expressed at a level of at least 1%, or at least 5%, or at least 10%, or at least 15%, or at least 20%, of total cellular protein as described herein.

In some embodiments, the nucleic acid sequence encoding the animal, e.g., mammalian, biopharmaceutical polypeptide is codon-optimized for expression in cyanobacteria. Alternatively, the nucleic acid sequence need not be codon-optimized, as high-level expression of the fusion polypeptide does not require codon optimization.

In some embodiments, the mature form of the biopharmaceutical polypeptide lacking the native signal sequence is expressed.

In some embodiments, the transgene that is expressed encodes an interferon, e.g., an interferon alpha, such as IFNA2. In some embodiments, the interferon is interferon-alpha, such as human interferon α-2. An illustrative polypeptide sequence is available under uniprot number P01563. The amino acid sequence of a mature form of human interferon alpha-2, which lacks the signal polypeptide, is provided in SEQ ID NO:1. In some embodiments, the IFNA2 protein is expressed as a fusion construct with cpcB, e.g., by replacing the cpcB gene in the cpc operon with a transgene encoding a cpcB*interferon fusion construct. In some embodiments, the transgene encodes an interferon polypeptide fused to an antibiotic resistance polypeptide, such as Npt1. In some embodiments, such a fusion polypeptide is introduced into the cpc operon for expression. In some embodiments, the gene encoding the Npt1*interferon fusion polypeptides is inserted to replace the cpcb gene in the cpc operon. In some embodiments, the fusion polypeptide comprises a protease cleavage site such as a Factor Xa cleavage site or alternative cleavage site, e.g., a Tobacco Etch Virus (TEV) cysteine protease cleavage site. Alternatively, the fusion polypeptide may comprise an Enteropeptidase, Thrombin, Protease 3C, Sortase A, Genase I, Intein, or a Snac-tag cleavage site (e.g., Kosobokova et al. 2016; Dang et al. 2019). In some embodiments, the fusion polypeptide may comprise a protein purification tag, such as a 6×His tag.

In some embodiments, the transgene that is expressed encodes a tPA, e.g., a human tPA lacking a native signal sequence. Human tPA has a molecular weight of about 70 kDa in the single-chain form. The tPA polypeptide had five domains: an N-terminal finger domain, an epidermal growth factor domain, a serine protease domain, and Kringle 1 and Kringle 2 domains. In some embodiments, the tPA polypeptide that is expressed is a truncated human tissue plasminogen activator (K2S, reteplase), which includes the Kringle 2 domain and the serine protease domain. Illustrative examples of tPA polypeptide sequences that can be expressed in accordance with the invention are shown in SEQ ID NOS:2 and 3. In some embodiments, the tPA that is expressed lacks the signal polypeptide. In some embodiments, the tPA incorporated into the fusion polypeptide has the amino acid sequence of SEQ ID NO:3. In some embodiments, the IFNA2 protein is expressed as a fusion construct with cpcB, e.g., by replacing the cpcB gene in the cpc operon with a transgene encoding a cpcB*tPA fusion construct. In some embodiments, the transgene encodes a tPA polypeptide fused to an antibiotic resistance polypeptide, such as Npt1. In some embodiments, such a fusion polypeptide is introduced into the cpc operon for expression. In some embodiments, the gene encoding the Npt1*tPA fusion polypeptides is inserted to replace the cpcb gene in the cpc operon. In some embodiments, the fusion polypeptide comprises a protease cleavage site such as a Factor Xa cleavage site or alternative cleavage site, e.g., a TEV cysteine protease cleavage site. Alternatively, the fusion polypeptide may comprise an Enteropeptidase, Thrombin, Protease 3C, Sortase A, Genase I, Intein, or a Snac-tag cleavage site (e.g., Kosobokova et al. 2016; Dang et al. 2019). In some embodiments, the fusion polypeptide may comprise a protein purification tag, such as a 6×His tag.

In some embodiments, the transgene that is expressed encodes an insulin e.g., a human insulin. An illustrative polypeptide sequence is available under uniprot number P01308. The amino acid sequence of a mature form of human insulin, which lacks the signal polypeptide, is provided in SEQ ID NO:4. In some embodiments, the insulin protein is expressed as a fusion construct with cpcB, e.g., by replacing the cpcB gene in the cpc operon with a transgene encoding a cpcB*insulin fusion construct. In some embodiments, the transgene encodes an insulin polypeptide fused to an antibiotic resistance polypeptide, such as Npt1. In some embodiments, such a fusion polypeptide is introduced into the cpc operon for expression. In some embodiments, the gene encoding the Npt1*insulin fusion polypeptides is inserted to replace the cpcb gene in the cpc operon. In some embodiments, the fusion polypeptide comprises a protease cleavage site such as a Factor Xa cleavage site or alternative cleavage site, e.g., a TEV cysteine protease cleavage site. Alternatively, the fusion polypeptide may comprise an Enteropeptidase, Thrombin, Protease 3C, Sortase A, Genase I, Intein, or a Snac-tag cleavage site (e.g., Kosobokova et al. 2016; Dang et al. 2019). In some embodiments, the fusion polypeptide may comprise a protein purification tag, such as a 6×His tag.

As noted above, in some embodiments, the transgene portion of a fusion construct in accordance with the invention may be codon optimized for expression in cyanobacteria. For example, in some embodiments, codon optimization is performed such that codons used with an average frequency of less than 12% by *Synechocystis* are replaced by more frequently used codons. Rare codons can be defined, e.g., by using a codon usage table derived from the sequenced genome of the host cyanobacterial cell. See, e.g., the codon usage table obtained from Kazusa DNA Research Institute, Japan (website www.kazusa.or.jp/codon/) used in conjunction with software, e.g., "Gene Designer 2.0" software, from DNA 2.0 (website www.dna20.com/) at a cut-off thread of 15%; or the software available at the website, idtdna.com/CodonOpt.

Preparation of Recombinant Expression Constructs

Recombinant DNA vectors suitable for transformation of cyanobacteria cells are employed in the methods of the invention. Preparation of suitable vectors and transformation methods can be prepared using any number of techniques, including those described, e.g., in Sambrook, Molecular Cloning, A Laboratory Manual (4th Ed, 2012); and Current Protocols in Molecular Biology (Ausubel et al., eds., 1994-2015). For example, a DNA sequence encoding a fusion protein of the present invention will be combined with transcriptional and other regulatory sequences to direct expression in cyanobacteria.

In some embodiments, the vector includes sequences for homologous recombination to insert the fusion construct at a desired site in a cyanobacterial genome, e.g., such that expression of the polynucleotide encoding the fusion construct will be driven by a promoter that is endogenous to the organism. A vector to perform homologous recombination will include sequences required for homologous recombination, such as flanking sequences that share homology with the target site for promoting homologous recombination.

Regulatory sequences incorporated into vectors that comprise sequences that are to be expressed in the modified cyanobacterial cell include promoters, which may be either constitutive or inducible. In some embodiments, a promoter for a nucleic acid construct is a constitutive promoter. Examples of constitutive strong promoters for use in cyanobacteria include, for example, the psbD1 gene or the basal promoter of the psbD2 gene, or the rbcLS promoter, which is constitutive under standard growth conditions. Various other promoters that are active in cyanobacteria are also known. These include the strong cpc operon promoter, the cpe operon and apc operon promoters, which control expression of phycobilisome constituents. The light inducible promoters of the psbA1, psbA2, and psbA3 genes in cyanobacteria may also be used, as noted below. Other promoters that are operative in plants, e.g., promoters derived from plant viruses, such as the CaMV35S promoters, or bacterial viruses, such as the T7, or bacterial promoters, such as the PTrc, can also be employed in cyanobacteria. For a description of strong and regulated promoters, e.g., active in the cyanobacterium *Anabaena* sp. strain PCC 7120 and *Synechocystis* 6803, see e.g., Elhai. *FEMS Microbiol Lett* 114: 179-184, (1993) and Formighieri, *Planta* 240:309-324 (2014).

In some embodiments, a promoter can be used to direct expression of the inserted nucleic acids under the influence of changing environmental conditions. Examples of environmental conditions that may affect transcription by inducible promoters include anaerobic conditions, elevated temperature, or the presence of light. Promoters that are inducible upon exposure to chemicals reagents are also used to express the inserted nucleic acids. Other useful inducible regulatory elements include copper-inducible regulatory elements (Mett et al., *Proc. Natl. Acad. Sci. USA* 90:4567-4571 (1993); Furst et al., Cell 55:705-717 (1988)); copper-repressed petJ promoter in *Synechocystis* (Kuchmina et al. 2012*, J Biotechn* 162:75-80); riboswitches, e.g. theophylline-dependent (Nakahira et al. 2013*, Plant Cell Physiol* 54:1724-1735; tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible promoters, such as those of the hsp70/dnaK genes (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element also can be, for example, a nitrate-inducible promoter, e.g., derived from the spinach nitrite reductase gene (Back et al., *Plant Mol. Biol.* 17:9 (1991)), or a light-inducible promoter, such as that associated with the small subunit of RuBP carboxylase or the LHCP gene families (Feinbaum et al., *Mol. Gen. Genet.* 226:449 (1991); Lam and Chua, Science 248:471 (1990)).

In some embodiments, the promoter may be from a gene associated with photosynthesis in the species to be transformed or another species. For example, such a promoter from one species may be used to direct expression of a protein in transformed cyanobacteria cells. Suitable promoters may be isolated from or synthesized based on known sequences from other photosynthetic organisms. Preferred promoters are those for genes from other photosynthetic species, or other photosynthetic organism where the promoter is active in cyanobacteria.

A vector will also typically comprise a marker gene that confers a selectable phenotype on cyanobacteria transformed with the vector. Such marker genes, include, but are not limited to those that confer antibiotic resistance, such as resistance to chloramphenicol, kanamycin, spectinomycin, G418, bleomycin, hygromycin, and the like.

Cell transformation methods and selectable markers for cyanobacteria are well known in the art (Wirth, *Mol. Gen. Genet.,* 216(1):175-7 (1989); Koksharova, *Appl. Microbiol. Biotechnol.,* 58(2): 123-37 (2002); Thelwell et al., *Proc. Natl. Acad. Sci. U.S.A.,* 95:10728-10733 (1998)).

Any suitable cyanobacteria may be employed to express a fusion protein in accordance with the invention. These include unicellular cyanobacteria, micro-colonial cyanobacteria that form small colonies, and filamentous cyanobacteria. Examples of unicellular cyanobacteria for use in the invention include, but are not limited to, *Synechococcus* and *Thermosynechococcus* sp., e.g., *Synechococcus* sp. PCC 7002, *Synechococcus* sp. PCC 6301, and *Thermosynechococcus elongatus*; as well as *Synechocystis* sp., such as *Synechocystis* sp. PCC 6803; and Cyanothece sp., such as PCC 8801. Examples of micro-colonial cyanobacteria for use in the invention, include, but are not limited to, *Gloeocapsa magma, Gloeocapsa phylum, Gloeocapsa alpicola, Gloeocapsa atrata, Chroococcus* spp., and *Aphanothece* sp. Examples of filamentous cyanobacteria that can be used include, but are not limited to, *Oscillatoria* spp., *Nostoc* sp., e.g., *Nostoc* sp. PCC 7120, and *Nostoc sphaeroides; Anabaena* sp., e.g., *Anabaena variabilis* and *Arthrospira* sp. ("*Spirulina*"), such as *Arthrospira platensis* and *Arthrospira maxima*, and *Mastigocladus laminosus*. Cyanobacteria that are genetically modified in accordance with the invention may also contain other genetic modifications, e.g., modifications to the terpenoid pathway, to enhance production of a desired compound.

Cyanobacteria can be cultured to high density, e.g., in a photobioreactor (see, e.g., Lee et al., *Biotech. Bioengineering* 44:1161-1167, 1994; Chaumont, *J Appl. Phycology* 5:593-604, 1990) to produce the protein encoded by the transgene. In some embodiments, the protein product of the transgene is purified. In many embodiments, the cyanobacteria culture is used to produce a desired, non-protein product, e.g., isoprene, a hemiterpene; β-phellandrene, a monoterpene; famesene, a sesquiterpene; or other products. The product produced from the cyanobacteria may then be isolated or collected from the cyanobacterial cell culture.

EXAMPLES

The following examples illustrate the over-expression of illustrative biopharmaceutical polypeptides in cyanobacteria.

Example 1. Expression of an Interferon in Cyanobacteria cpcB*IFN Fusion Constructs This example demonstrates the expression of the mature human interferon α-2 protein (Uniprot No. P01563), referred to in this example as IFN, in the cyanobacteria *Synechocystis* sp. PCC 6803 (*Synechocystis*). To validate the fusion constructs approach, three different DNA constructs were designed for the transformation of wild type (WT) *Synechocystis* through double homologous DNA recombination in the cpc operon locus (FIG. 1A). The nucleic acid construct IFN (FIG. 1B) was codon optimized for expression in *Synechocystis*, and designed to replace the cpcB gene in the cpc operon. IFN was followed by the chloramphenicol resistance cassette (cmR) in an operon configuration. Construct cpcB-IFN (FIG. 1C) was designed to insert both the IFN and the cmR genes after the cpcB gene in an operon configuration. Finally, construct cpcB*IFN (FIG. 1D) was designed to replace the cpcB gene in the cpc operon with the fusion construct cpcB*IFN, followed by the cmR gene in an operon configuration. A Factor Xa cleavage-encoding sequence was inserted between the cpcB and IFN genes in the construct of FIG. 1D.

Figure 1:
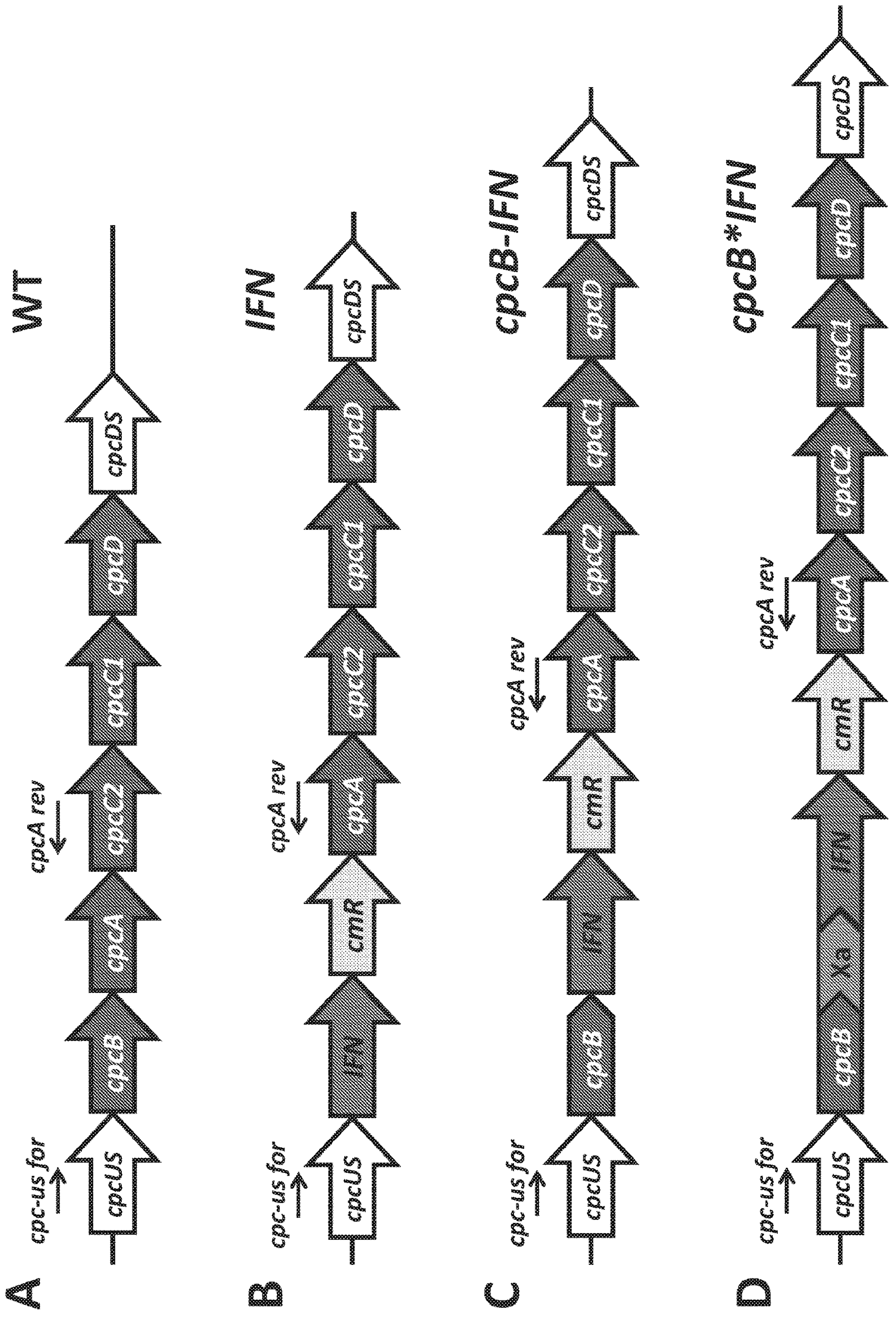
FIG. 1. Schematic overview of DNA constructs designed for the transformation of the *Synechocystis* PCC 6803 (*Synechocystis*) genome. (A) The native cpc operon, as it occurs in wild type *Synechocystis*. This DNA sequence and associated strain are referred to as the wild type (WT). (B) Insertion in the cpc operon of the codon-optimized human interferon (IFN) gene followed by the chloramphenicol (cmR) resistance cassette in an operon configuration, replacing the phycocyanin-encoding β-subunit cpcB gene of *Synechocystis*. This DNA construct is referred to as IFN; (C) Insertion in the cpc operon of the codon-optimized IFN gene immediately downstream of the phycocyanin-encoding β-subunit cpcB gene of *Synechocystis*, followed by the cmR resistance cassette, in an operon configuration. This DNA construct is referred to as cpcB-IFN; (D) Insertion in the cpc operon of the codon-optimized IFN gene as a fusion construct with the phycocyanin-encoding β-subunit cpcB gene, with the latter in the leader sequence position. The fusion construct cpcB*IFN was followed by the cmR resistance cassette in an operon configuration, cpcB and IFN genes were linked by the DNA sequence encoding the Factor Xa cleavage site. The latter comprises the Ile-Glu/Asp-Gly-Arg amino acid sequence. This DNA construct is referred to as the cpcB*IFN.
Figure 2:
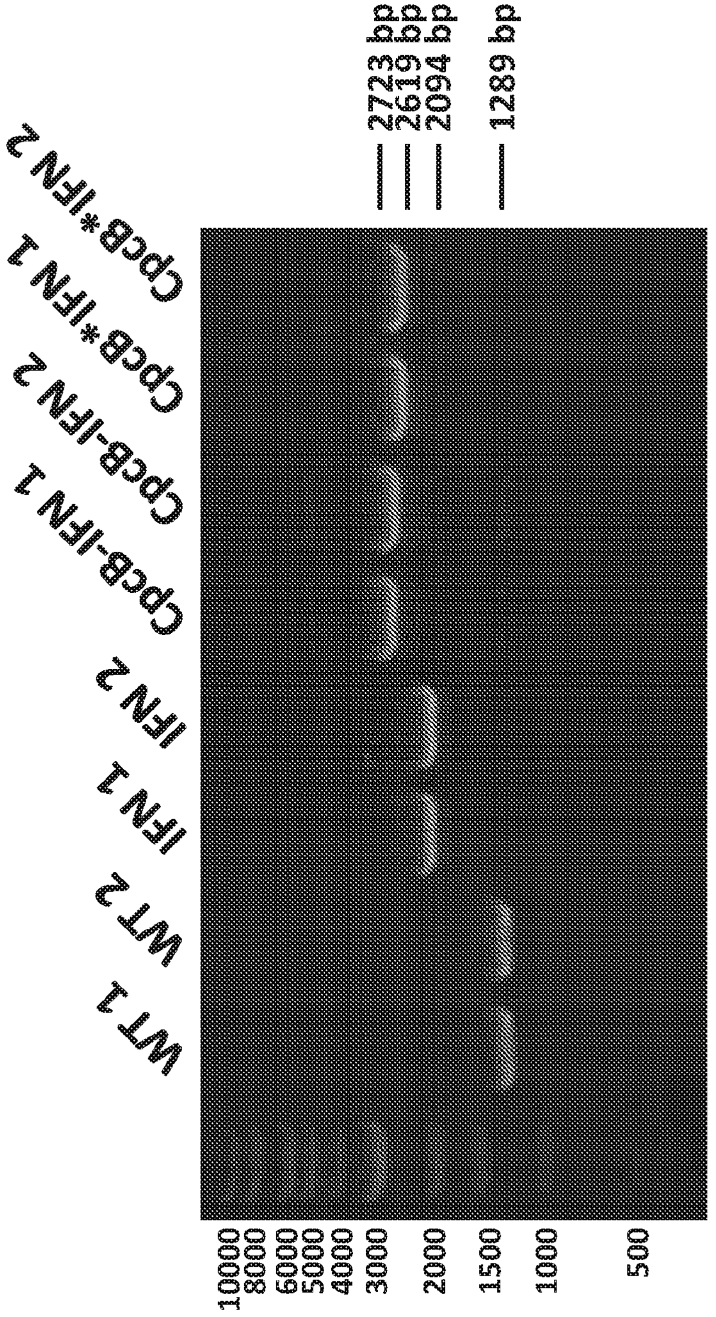
FIG. 2. Genomic DNA PCR analysis testing for transgenic DNA copy homoplasmy in *Synechocystis* transformants. Wild type and transformant strains were probed in genomic DNA PCR reactions for product generation and transgenic DNA segregation. Primers <cpc-us for> and <cpcA rev> showed substantially different and unique products in the wild type and the different transformants comprising the constructs of FIG. 1. Wild type PCR products had a 1,289 bp size, whereas the IFN, cpcB-IFN, and the cpcB*IFN transformants generated 2,094, 2,723, and 2.619 bp size products, respectively. Absence of wild type products from the latter was evidence of DNA copy homoplasmy for the transformants. (The cpcB-IFN construct generated a product size slightly larger than that of the cpcB*IFN because it contained the *Synechocystis* native cpcB-cpcA intergenic DNA sequence. Please see gene nucleotide sequences in the Supplementary Materials.)

PCR analysis to determine whether transgenic DNA copy homoplasmy was achieved. Primers cpc-us for and cpcA rev were designed on the flanking regions of the transgenic DNA insertion sites (FIG. 1). PCR amplification using WT genomic DNA as a template generated a product of 1,289 bp (FIG. 2). PCR amplification using DNA from the transformant IFN, CpcB-IFN, and CpcB*IFN strains generated the expected product sizes of 2,094 bp, 2,723 bp and 2,619 bp, respectively. DNA copy homoplasmy was evidenced by the absence of WT PCR products in the PCR amplification reactions of the IFN transformants.

Figure 3:
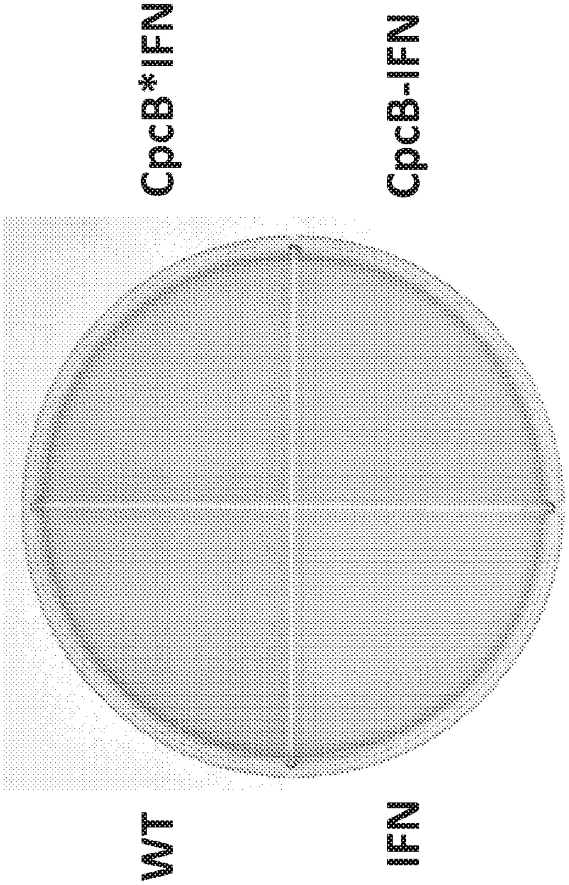
FIG. 3. Coloration of cells from photoautotrophically-grown liquid cultures showing a blue-green wild type (WT) phenotype, and greenish phenotype for the IFN, CpcB-IFN, and CpcB*IFN-containing transformants. The latter did not assemble phycocyanin rods, hence the absence of the distinct blue cyanobacterial coloration from the cells.

After DNA copy homoplasmy was achieved, WT and transformant strains were grown photo-autotrophically in liquid BG-11 cultures. The visual phenotype (FIG. 3) was noticeably different between the WT and transformant strains. The WT cells had a blue-green coloration, consistent with the presence of blue phycocyanin and green chlorophyll pigments in their functional light-harvesting antennae. All transformant strains showed a yellow-green pigmentation, suggesting lack of phycocyanin, which is responsible for the blue pigmentation of the cells. This is consistent with previously reported results (Kirst et al. 2014; Formighieri and Melis 2015; Chaves and Melis 2016) and underscores the absence of assembled phycocyanin rods in the transformants.

Figure 4:
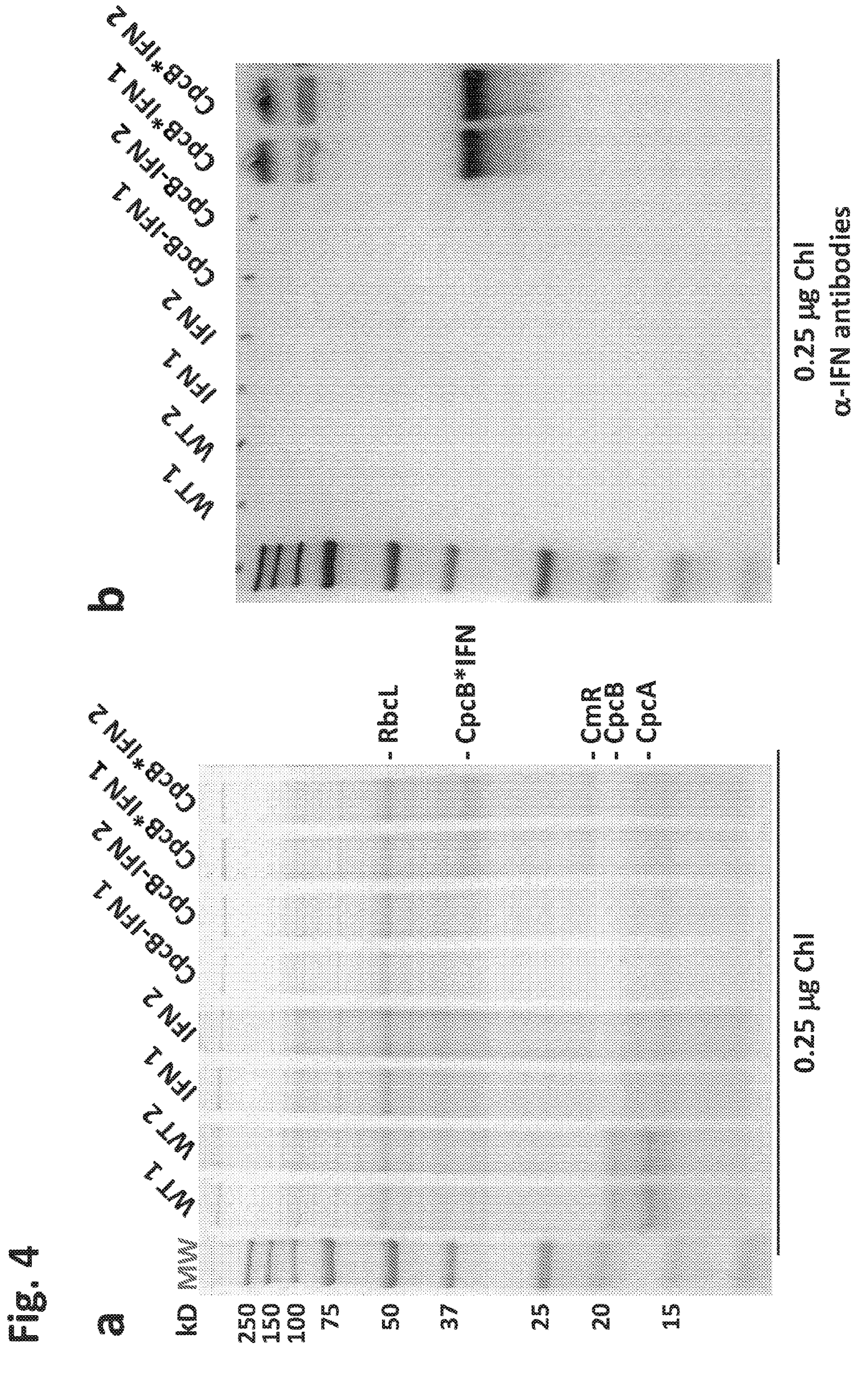
FIG. 4. Protein expression analysis of *Synechocystis* wild type and transformants. (A) Total cellular protein extracts were resolved by SDS-PAGE and visualized by Coomassie-stain. Two independent replicates of total protein extracts from wild type (WT), and IFN, CpcB-IFN and CpcB*IFN transformant cells were loaded onto the SDS-PAGE. Individual native and heterologous proteins of interest are indicated to the right of the gel. Sample loading corresponds to 0.25 μg of chlorophyll. Note the clear presence of a heterologous protein migrating to ~36 kD in the CpcB*IFN fusion extracts. (B) Total protein extracts of (A) were subjected to Western-blot analysis with loading of the lanes as per FIG. 4A. Specific polyclonal antibodies against the human IFN protein were used to probe target proteins. Sample loading corresponds to 0.25 μg of chlorophyll. Note the specific antibody cross-reaction with proteins migrating to ~36 and ~108 kD in the cpcB*IFN fusion and the absence of a cross reaction with any protein from the IFN and cpcB-IFN transformant cells. The latter do not seem to make/accumulate IFN.

Protein analysis of total cell extracts from WT and transformant *Synechocystis* was performed using SDS-PAGE followed by Coomassie blue staining and Western blot analysis (FIG. 4). Two replicate samples of WT protein extracts showed the presence of CpcB β-subunit and CpcA α-subunit of phycocyanin as the dominant protein bands, migrating to ~19 and ~17 kD, respectively. Another dominant band in the SDS-PAGE profile was the large subunit of Rubisco (RbcL), migrating to about ~56 kD (FIG. 4A). The latter was used as a normalization factor in protein quantification and as a loading control of the gels.

CpcB and CpcA subunits were not evident in the protein extracts of the transformants because of inability of these transformants to assemble the phycobilisome-peripheral phycocyanin rods. The IFN and cpcB-IFN transformants failed to show accumulation of recombinant IFN protein in the expected ~19 kD region, both in the SDS-PAGE and the associated Western blot (FIG. 4B, IFN and CpcB-IFN), suggesting either very-low levels or absence of the recombinant IFN protein from these samples. These results show that the powerful cpc promoter was not sufficient to support IFN (~19 kD) protein expression/accumulation in *Synechocystis*. In contrast, protein extracts from the cpcB*IFN fusion transformants showed a clear presence of an abundant protein with electrophoretic mobility to ~36 kD. This band was attributed to accumulation of the CpcB*IFN fusion protein (FIG. 4A, CpcB*IFN). Identification of the ~36 kD protein was tested by Western blot analysis with specific polyclonal antibodies raised against the human IFN protein (FIG. 4B, CpcB*IFN). A strong reaction between the polyclonal antibodies and a protein band migrating to ~36 kD suggested that this band is the recombinant CpcB*IFN protein. Moreover, binding was also detected with protein bands at a higher MW, suggesting the formation/presence of complexes (~108 kD) containing the CpcB*IFN fusion protein.

To evaluate the effect of DNA codon-use optimization on the IFN protein expression level, CpcB*IFN fusion DNA constructs were designed using the *Synechocystis* codon optimized IFN as well as the native unoptimized human DNA sequence (termed IFN') for comparative expression measurements in *Synechocystis*. The latter construct harbored the same elements of the CpcB*IFN fusion, with the exception of the IFN gene that was replaced by the human native IFN' sequence (no codon-use optimization). Wild type (WT). cpcB*IFN', and cpcB*IFN transformant strains were grown in parallel, and total cell proteins were extracted and subjected to SDS-PAGE analysis. Upon Coomassie staining of the SDS-PAGE (FIG. 5), the WT protein extract showed as main subunits the 56 kD RbcL, 19 kD CpcB, and 17 kD CpcA. The latter two subunits were missing from the extract of the transformant cells, shown in three independent replicates per transformant in FIG. 5. Densitometric analysis of Coomassie stained SDS-PAGE (FIG. 5) showed the presence of RbcL to ~12.5% of total cellular protein. Fusion constructs accumulated to ~10.2% in the cpcB*IFN' and ~11.8% in cpcB*IFN codon-optimized transformant strains. Validation of the Coomassie stained SDS-PAGE protein assignments was obtained through Western blot analysis with specific polyclonal antibodies (not shown).

Figure 6:
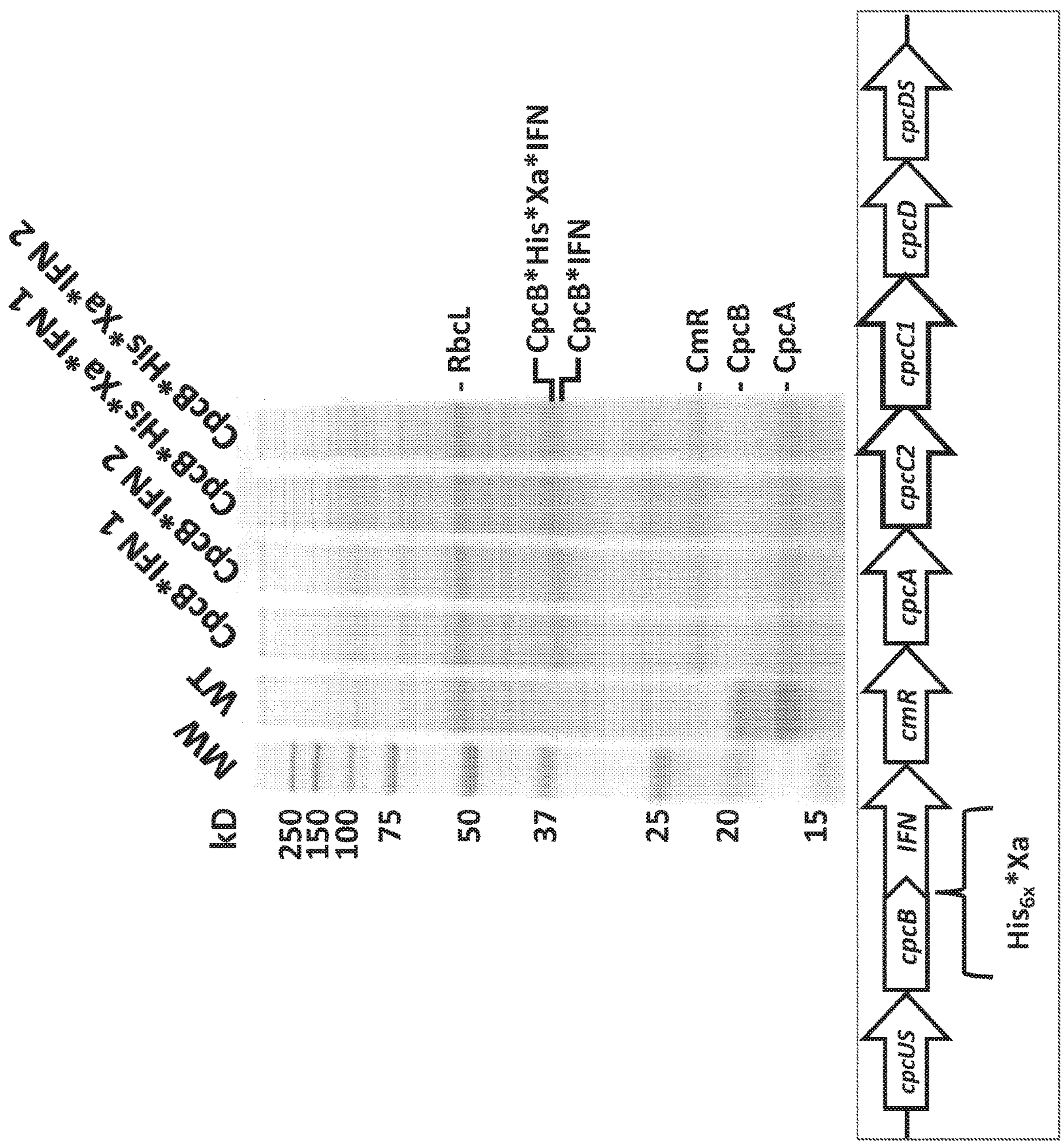
FIG. 6. Protein expression analysis of *Synechocystis* wild type (WT) and transformants harboring the cpcB*IFN fusion construct. Total cellular protein extracts were resolved by SDS-PAGE and visualized by Coomassie-stain. Two different versions of the fusion construct were used comprising the CpcB*IFN fusion and the more extensive cpcB*His*Xa*IFN fusion configuration, followed by the cmR resistance cassette. Equivalent amount of the CpcB*IFN and the CpcB*His*Xa*IFN fusion proteins were expressed in *Synechocystis*. Individual native and heterologous proteins of interest are indicated to the right of the gel. Sample loading corresponds to 0.25 μg of chlorophyll.

The above results showed that IFN successfully accumulated in *Synechocystis* only when expressed in a fusion construct configuration with the native highly-expressed CpcB subunit of phycocyanin, regardless of whether the IFN gene was codon-optimized or not. In order to isolate the recombinant fusion protein, we designed a new DNA construct referred to as the cpcB*His*Xa*IFN, based on the previous CpcB*IFN construct (FIG. 6). A DNA fragment encoding the domain of six histidines and the Factor Xa cleavage-site was inserted between the cpcB and the IFN genes in the fusion construct. Protein analysis was then conducted on the transformant lines. Coomassie staining of the SDS-PAGE profile (FIG. 6) showed the abundant RbcL, CpcB and CpcA subunits in the wild type extracts (FIG. 6, WT).

The cpcB*IFN transformants lacked the CpcB and CpcA proteins but accumulated the CpcB*IFN as a ~36 kD protein (FIG. 6, CpcB*IFN). The cpcB*His*Xa*IFN transformants also lacked the CpcB and CpcA proteins but accumulated an abundant protein band with a slightly higher apparent molecular mass than that of the CpcB*IFN (FIG. 6, CpcB*His*Xa*IFN). This band was attributed to the CpcB*His*Xa*IFN protein. The fact that CpcB*His*Xa*IFN protein band showed a similar abundance as that of the CpcB*IFN construct suggested that the His*Xa addition to the CpcB*IFN fusion did not adversely affect the expression level of this recombinant protein.

Batch-Based Purification of the cpcB*His*Xa*IFN Recombinant Protein

We initially applied a "batch" purification procedure to the recombinant CpcB*His*Xa*IFN protein using a His-Select resin (Sigma) and by following the manufacturer's instructions. The procedure was conducted in Eppendorf tubes, thereby minimizing the amount of resin and cell extract used. Total cell extracts from WT, cpcB*IFN, and cpcB*His*Xa*IFN fusion construct transgenic cells were employed in a side-by-side comparative resin treatment and purification analysis. Prior to incubation with the resin, cellular extracts were incubated on ice for 20 min in the presence of 1% Triton X-100 to disperse cellular aggregates that appeared to interfere with the precipitation of the resin upon centrifugation. Un-solubilized cell debris were pelleted and discarded following a brief centrifugation. The supernatant, containing the cellular protein extracts, was incubated with the resin for 5 min, followed by centrifugation to pellet the resin and any His-tagged proteins bound to it.

Lane 1 in FIG. 7 shows the cell extracts (upper panel) and the resin (lower panel) of the wild type, cpcB*IFN, and cpcB*His*Xa*IFN fusion construct transgenic cells prior to incubation with the resin. The resin had a natural pink coloration.

Lane 2 in FIG. 7 shows the cell extracts (upper panel) and the resin pellet (lower panel) of the wild type, cpcB*IFN, and cpcB*His*Xa*IFN cell lines following a 5-min incubation with the resin and a subsequent centrifugation. There was a blue coloration of the resin pellet and green coloration of the supernatant.

Lanes 3-5 in FIG. 7 show the remaining extracts (upper panels) and the resin pellet (lower panels) of the wild type, cpcB*IFN, and cpcB*His*Xa*IFN cell lines following a consecutive wash of the resin with a buffer containing 10 mM imidazole to remove non-target proteins. The supernatant was clear and there was a pink coloration of the resin after the third wash (lane 5) for the wild type and cpcB*IFN transformants, suggesting absence of His-tagged proteins. There was a blue coloration of the resin in the cpcB*His*Xa*IFN sample, which was retained in this pellet (lanes 3-5) in spite of the repeated 10 mM imidazole wash, suggesting the presence and binding to the resin of blue-colored His-tagged proteins.

Lanes 6-8 in FIG. 7 show the subsequent extracts (upper panel) and the resin pellet (lower panel) of the wild type, cpcB*IFN, and cpcB*His*Xa*IFN cell lines following a wash of the resin three times with a buffer containing 250 mM of imidazole, designed to dissociate His-tagged proteins from the resin. There was a bluish color to the supernatant in lanes 6 and 7 and a corresponding loss of the blue color from the resin pellet, suggesting the specific removal of His-tagged proteins from the resin under these conditions.

Fractions eluted from the resin upon application of 250 mM imidazole were analyzed by SDS-PAGE (FIG. 8). Elution fractions from both WT and the cpcB*IFN transgenic extracts showed no protein bands in the Coomassie stained gels (FIG. 8, left and middle panels), whereas eluent 1 (E1) from the cpcB*His*Xa*IFN extracts clearly showed the presence of protein bands, with the most abundant migrating to ~36 kD, attributed to the CpcB*His*Xa*IFN fusion protein. Secondary bands migrating to ~17 kD, ~27 kD, and ~108 kD were also noted (FIG. 8, right panel). The ~17 kD protein was attributed to the CpcA α-subunit of phycocyanin. The ~27 kD protein could be the CpcG1 subunit of the phycobilisome, a phycocyanin rod-core linker polypeptide (Kondo et al., 2005), and the ~108 kD band is tentatively attributed to a CpcB*His*Xa*IFN trimer, as it was shown to contain the CpcB*His*Xa*IFN fusion protein (see below).

The nature of the pigmentation of proteins from eluent 1 of the cell extracts was investigated through spectrophotometric analysis (FIG. 9A). The spectra of E1 from the WT and CpcB*IFN extracts did not show any absorbance features, consistent with absence of coloration in lanes 6-8 (FIG. 7) of these samples. Eluent 1 from the CpcB*His*Xa*IFN sample showed a distinct absorbance band with a peak at ~625 nm and a secondary broad band peaking in the UV-A region of the spectrum. This closely resembled the absorbance spectrum of phycocyanin from *Synechocystis* (Kirst et al. 2014), suggesting the presence of bilin pigment covalently-bound to the CpcB*His*Xa*IFN fusion protein. To further investigate this observation, absorbance spectra of total protein extracts from WT and cpcB*His*Xa*IFN transformant cells were also measured. These were compared with the absorbance spectrum of cells lacking phycocyanin due to a Δcpc operon deletion (Kirst et al. 2014). The spectrum of WT cells showed typical absorbance bands of chlorophyll at 680 nm and phycocyanin at 625 nm (FIG. 9B). The extract from the Δcpc transformants showed the specific Chl absorbance peak at 680 nm, whereas the phycocyanin absorbance peak at around 625 nm was missing (FIG. 9B). The absorbance spectrum from the cpcB*His*Xa*IFN transformant cells showed a substantially lower absorbance at about 625 nm due to depletion of phycocyanin, but this lowering was not as extensive as that observed with the Δcpc cells (FIG. 9B). The difference, and apparent low-level absorbance of the cpcB*His*Xa*IFN cells at 625 nm, suggests that the CpcB protein, albeit in a fusion construct configuration with the IFN, and/or the CpcA protein that apparently accompanies this recombinant protein, covalently bind at least some of the phycobilin pigment that is naturally associated with it, and which is manifested in the blue coloration of the E1 eluent.

Column-Based Purification of the cpcB*his*Xa*IFN Recombinant Proteins

Based on the initial encouraging results obtained with the "batch" purification approach, we proceeded to conduct a "column-based" purification of the His-tagged proteins (FIG. 10). This experimental work was conducted as an alternative method in an attempt to elute a greater amount of the CpcB*His*Xa*IFN protein. Total protein extract from the cpcB*His*Xa*IFN transformant cells, mixed with 5 mM imidazole, was loaded onto the resin. Four subsequent washing steps were conducted with 5 mM imidazole to remove non-target proteins from the resin. After these washing steps, elution of the target protein with 250 mM imidazole was undertaken. The pigmentation pattern of the resulting fractions was in accordance with the results obtained with the "batch-based" purification (please see below).

Lane 1 in FIG. 10, upper panel, shows the cpcB*His*Xa*IFN cell extracts that were incubated in the presence of 5 mM imidazole prior to loading on the resin. Lane 1 in FIG. 10, lower panel, shows the SDS-PAGE protein profile of these extracts, indicating presence of all expected *Synechocystis* proteins.

Lane 2 in FIG. 10, upper panel, shows the cpcB*His*Xa*IFN cell extracts after incubation with the resin but prior to washing with additional imidazole. Lane 2 in FIG. 10, lower panel, shows the SDS-PAGE protein profile of these extracts, obtained upon removal of the resin from the mix, again indicating presence of all expected *Synechocystis* proteins Lanes 3-6 in FIG. 10 (upper panel) show the cpcB*His*Xa*IFN cell extracts that were removed from the resin upon four consecutive washes with 5 mM imidazole and (FIG. 10, lower panel) the SDS-PAGE protein profile of these extracts, showing removal of the majority of cellular proteins in the first wash (FIG. 10, lane 3) and the virtual absence of cell proteins (lane 4 to lane 6) in three additional wash steps with 5 mM imidazole.

Lanes 7-9 in FIG. 10 (upper panel) show the further removal of bound His-tagged proteins from the cpcB*His*Xa*IFN cell extracts. These eluted from the resin upon three consecutive washes with 250 mM imidazole. FIG. 10 (lower panel) is the SDS-PAGE protein profile of these extracts, showing substantial enrichment in mainly four proteins with apparent molecular weights of ~108, 36, 27, and 17 kD. The majority of these proteins were eluted upon the first application of the 250 mM imidazole (FIG. 10, lane 7), as subsequent elution treatments (FIG. 10, lanes 8 and 9) produced much lower levels of protein eluent. Western blot analysis with specific anti-IFN antibodies showed strong cross reactions with the 36 and 108 kD protein bands only (FIG. 11). The ~17 kD protein was attributed to the CpcA α-subunit of phycocyanin, as it reacted with CpcA-specific antibodies (not shown, but see also below), whereas the 27 kD protein was attributed to the CpcG1 linker polypeptide (Kondo et al. 2005) that helped to bind the CpcA α-subunit to the CpcB*His*Xa*IFN fusion complex, thereby explaining the simultaneous elution of all three proteins from the resin.

Blue Coloration of the Target Proteins

The blue coloration of the target proteins (FIGS. 7 and 10) and the absorbance spectral evidence of FIG. 9A, suggested the presence of bilin in association with the recombinant CpcB*His*Xa*IFN protein. This finding was surprising as CpcB*fusion constructs are known to abolish the assembly of the phycocyanin peripheral rods of the phycobilisome (Formighieri and Melis 2015; 2016; Chaves et al. 2017; Betterle and Melis 2018; 2019), leading to the assumption of a CpcB inability to bind bilin. To further test the spectrophotometric suggestion of bilin presence (FIG. 9A), SDS-PAGE analysis of protein extracts from wild type, the cpcB*His*Xa*IFN transformant, and the resin column-based 1st eluent proteins of the latter (FIG. 12A) were subjected to "zinc-staining" (please see Materials and methods). Zinc-staining is designed to specifically label the open tetrapyrroles that are covalently bound to *Synechocystis* proteins. FIG. 12B shows the result of the Zn-staining of proteins in a duplicate gel, as the one shown in FIG. 12A. In the WT, Zn-staining occurred for proteins migrating to ~19 and ~17 kD, attributed to the native CpcB and CpcA phycocyanin subunits. Zn-staining of the total CpcB*His*Xa*IFN transformant cell extract occurred for protein bands migrating to ~36 and ~17 kD, attributed to the CpcB*His*Xa*IFN and the CpcA proteins, respectively. Zn-staining of the first resin eluent (E1) fraction occurred for protein bands migrating to ~108, ~36 and ~17 kD, putatively attributed to a CpcB*His*Xa*IFN trimer, the CpcB*His*Xa*IFN monomer and the CpcA proteins, respectively. These results corroborate the evidence based on spectrophotometry and Western blot analysis, clearly showing the presence of bilin in association with the CpcB*His*Xa*IFN fusion and residual CpcA proteins.

nptI*IFN Fusion Constructs

To further evaluated fusion constructs in the expression and accumulation of biopharmaceutical proteins, two different fusion constructs were designed for the transformation of wild type (WT) *Synechocystis*, based on the nptI gene serving as the leader sequence in a nptI*IFN configuration and through homologous DNA recombination in the cpc operon or glgA1 locus sites (FIG. 13A). In such constructs, the NptI protein served as the antibiotic selection marker, in addition to being the leader protein sequence in the fusion construct (Betterle and Melis 2018; 2019). SDS-PAGE profile of *Synechocystis* protein extracts showed absence of IFN from the wild type, as expected (FIG. 13B, WT). The cpcB*His*Xa*IFN transformant showed the expected accumulation of a protein band migrating to about 36 kD (FIG. 13B, cpcB*His*Xa*IFN), whereas two different lines of a transformant expressing the nptI*His*Xa*IFN construct in the cpc operon locus showed the presence of a 46 kD protein attributed to this fusion. Positive identification of these assignments was offered by the Western blot analysis of duplicate gels as the one shown in FIG. 13C, further confirming the relative abundance of the fusion constructs expressed in the different *Synechocystis* genome loci.

Antiviral Activity of the Native and CpcB*IFN Fusion Protein

Activity the cyanobacterial recombinant CpcB*His*Xa*IFN protein was compared with that of commercially-available native interferon provided by the PBL Assay Science. Piscataway, N.J., USA (FIG. 14). The results showed that 0.0875 ng/mL of CpcB*His*Xa*IFN fusion interferon was needed to cause a 50% inhibition in encephalomyocarditis (EMC) virus infection, whereas the commercial control required 0.002 ng/mL to cause a 50% inhibition in EMC infection. Part of the difference in sensitivity is probably due to the presence of the CpcB leader sequence in the CpcB*His*Xa*IFN fusion protein, which may have slowed the activity of the fusion IFN. This assumption was validated upon measurements with the cyanobacterial recombinant IFN protein, from which the CpcB leader sequence was removed (Xa excision function).

Example 2. Expression of Tissue Plasminogen Activator Derivative K2S Protein in Cyanobacteria K2S Fusion Constructs The fusion constructs approach was also implemented with the tissue plasminogen activator derivative K2S protein. The modified cpc operon with the cpcB*His*Xa*K2S construct was coupled with the chloramphenicol (cmR) resistance cassette and expressed under the control of the cpc promoter (FIG. 15A). A similar construct was made in which the Factor Xa protease cleavage domain was replaced by the Tobacco Etch Virus (TEV) cysteine protease cleavage site. SDS-PAGE analysis of the total protein content of wild type, cpcB*His*Xa*K2S, and cpcB*His*TEV*K2S are shown in FIG. 15B. A single WT and three independent lines of each the cpcB*His*Xa*K2S, and cpcB*His*TEV*K2S transformants are shown in this figure. Western blot analysis of the same protein profile was conducted with polyclonal antibodies raised against the CpcA α-subunit of phycocyanin, which also recognize the CpcB β-subunit (FIG. 15C). The results clearly show that dominant in the wild type 19 kD CpcB β-subunits and CpcA α-subunits of phycocyanin are absent in the cpcB*His*Xa*K2S, and cpcB*His*TEV*K2S transformants. This is consistent with previous results on the protein phenotype of cpcB*fusion transformants, and it serves as evidence that the cpcB*His*Xa*K2S, and cpcB*His*TEV*K2S transformants have reached a state of transgenic DNA homoplasmy, underlined by the absence of wild type products in the CpcB and CpcA electrophoretic mobility region. The results also show expression of the CpcB*His*Xa*K2S, and CpcB*His*TEV*K2S transgenic proteins, evidenced by the presence of 58.9 kD protein bands in the gels and the corresponding Western blots (FIG. 15C).

Example 3. Expression of Insulin in Cyanobacteria

Insulin Fusion Construct

The fusion constructs approach was further implemented with the human pro-insulin protein expression. The modified cpc operon with the cpcB*INS construct was coupled with the kanamycin (nptI) resistance cassette and expressed under the control of the cpc promoter (FIG. 16A). SDS-PAGE profile analysis of the total protein content of wild type, cpcB*INS, and an earlier transformant carrying the β-phellandrene synthase gene (PHLS) from lavender were compared (FIG. 16B). The results clearly showed that dominant in the wild type ~19 kD CpcB β-subunit and ~17 kD CpcA α-subunit of phycocyanin are absent in the cpcB*INS, as they are also absent from the cpcB*PHLS transformants. This is consistent with previous results on the protein phenotype of "cpcB*fusion" transformants, and serves as evidence that the cpcB*INS transformants have reached a state of transgenic DNA homoplasmy, underscored by the absence of wild type products in the CpcB and CpcA electrophoretic mobility region. The results also showed expression of the CpcB*INS transgenic protein, evidenced by the presence of ~28 kD protein band specifically in the respective gel lanes (FIG. 16B, CpcB*INS).

Example 4. Expression of the Tetanus Toxin Fragment C (TTFC) in Cyanobacteria

TTFC Fusion Construct

The fusion construct approach was also reduced to practice with the over-expression of the Tetanus Toxin Fragment C (TTFC) protein in cyanobacteria. The modified cpc operon, in this case with the cpcB*L7*His*TEV*TTFC construct, was coupled with the streptomycin (smR) resistance cassette and expressed under the control of the cpc promoter (FIG. 17A). The work compared the SDS-PAGE profile of the total protein content of wild type, the recipient LTV strain (a transformant carrying the isoprene synthase gene from lavender), and the cpcB*L7*His*TEV*TTFC fusion construct (FIG. 17B, left panel). In this configuration, presence of the His-tag allowed for a subsequent isolation and purification of the fusion protein. The SDS-PAGE Coomassie stain results clearly showed that the dominant in the wild type ~19 kD CpcB β- and ~17 kD CpcA α-subunits of phycocyanin are absent from the TTFC (cpcB*L7*His*TEV*TTFC) transformant, as they are also absent from the LTV (cpcB*L7*TEV*ISPS) transformant. This is consistent with previous results on the protein phenotype of "cpcB*fusion" transformants, and serves as evidence that the cpcB*L7*His*TEV*TTFC transformants have reached a state of transgenic DNA homoplasmy, underscored by the absence of wild type products in the CpcB and CpcA electrophoretic mobility region. Importantly, densitometric analysis of the SDS-PAGE Coommassie stain showed that the 72 kD cpcB*L7*His*TEV*TTFC fusion protein accounted for about 28% of the total cell protein. These results were validated by Western blot analysis, probed with specific polyclonal antibodies against the TTFC polypeptide (FIG. 173, right panel). Noted was the antibody cross reaction with the 72 kD cpcB*L7*His*TEV*TTFC fusion protein, but also with a ~290 kD putative trimeric [cpcB*L7*His*TEV*TTFC]×3 undissolved fusion protein complex, plus some lower molecular size putative proteolysis fragments of the cpcB*L7*His*TEV*TTFC fusion protein.

Example 5. Expression of the Receptor Binding Domain (RBD) of the SARS-CoV-2 Virus in Cyanobacteria RBD Fusion Construct The fusion construct approach was also reduced to practice with the over-expression of a viral protein, the Receptor Binding Domain (RBD) of the spike (S) protein from the SARS-CoV-2, which causes the coronavirus disease 2019 (COVID-19). Map of the modified cpc operon expressing the cpcB*L7*His*TEV*RBD fusion construct, including a linker of seven amino acids (L7), a His×6-tag (His) and the TEV cleavage factor, followed by the Receptor Binding Domain (RBD) of the spike (S1) protein from the SARS-CoV-2 virus is shown in FIG. 18 (A). SDS-PAGE and Coomassie stain of the protein extracts from the LTV recipient strain (LTV), and a transformant line harboring the cpcB*L7*His*TEV*RBD fusion protein (RBD) are shown in FIG. 18 (B, left panel). The arrow points to the electrophoretic mobility of the 45 kD RBD fusion protein, which partially overlaps a native *Synechocystis* 44 kD protein. Western blot analysis of the electropheretically-resolved protein profile for the LTV and RBD *Synechocystis* strains, probed with specific polyclonal antibodies against the leader CpcB protein, showed an antibody cross reaction with the 45 kD cpcB*L7*His*TEV*RBD fusion protein (FIG. 18 B, middle panel). Further identification of the 45 kD protein in the RBD sample was achieved by Zinc-stain analysis of the electophretically-separated proteins from *Synechocystis* expressing the LTV and RBD fusion construct phenotypes (FIG. 18 B, right panel). Zn-staining is designed to highlight the presence of bilin tetrapyrrole pigments. Note the specific Zn-staining of a band at 45 kD in the RBD expressing transformant, attributed to the presence of the bilin-binding CpcB protein in the cpcB*L7*His*TEV*RBD fusion protein. (A protein band migrating to about 85 kD is also stained with Zn, and is attributed to the bilin-binding CpcB protein in the cpcB*L7*His*TEV*ISPS expressing construct, which is larger than the RBD-containing one.)

Summary of Examples

Eukaryotic transgenes of plant and animal origin are not always expressed to significant levels in cyanobacteria (Desplancq et al. 2005; 2008; Jindou et al. 2014; Formighieri and Melis 2015). Based on these results, the choice of a strong promoter, such as cpc, was necessary but not sufficient to provide high levels of terpene synthase expression in cyanobacteria. Previous investigations pointed to the importance of efficient translation for protein accumulation. This also appears to be the case in the illustrative examples provided above.

The cpc operon promoter controls expression of the abundant phycocyanin subunits and their associated linker polypeptides of the phycobilisome light-harvesting antenna (FIG. 1A). This endogenous strong promoter was employed in an effort to drive heterologous expression of the codon-optimized IFN gene. However, of the three IFN construct configurations (FIG. 1*b*, 1*c*, and 1*d*), only the fusion construct cpcB*Xa*IFN produced substantial amounts of the transgenic IFN protein (FIG. 1*d*). Earlier real time RT-qPCR analysis compared transcript levels of plant-origin transgenes, under the same different configurations as those depicted in FIG. 1. The analysis revealed that such transgene constructs resulted in about equal rates of transcription and showed comparable steady-state levels of eukaryotic transgene mRNA (Formighieri and Melis 2016). Hence, the rate of transcription does not appear to be the determinant of recombinant protein abundance in this case.

Protein synthesis was later investigated by analyzing the polyribosomes distribution profile associated with the various transcripts (Formighieri and Melis 2016). A high density of polyribosomes in prokaryotes, such as cyanobacteria, was attributed to a ribosome pileup, when a slower ribosome migration rate on the mRNA causes multiple ribosomes to associate with the same mRNA molecule (Qin and Fredrick 2013). This was observed to be the case for the FIG. 1*b*- and 1*c*-type constructs resulting in low transgenic protein accumulation (Formighieri and Melis 2016). Conversely, a low density of polyribosomes is attributed to efficient ribosome migration on the mRNA, resulting in efficient translation and high levels of protein accumulation (Qin and Fredrick 2013). This was observed to be the case for the FIG. 1*d*-type constructs of high transgenic protein accumulation (Formighieri and Melis 2016).

Figure 5:
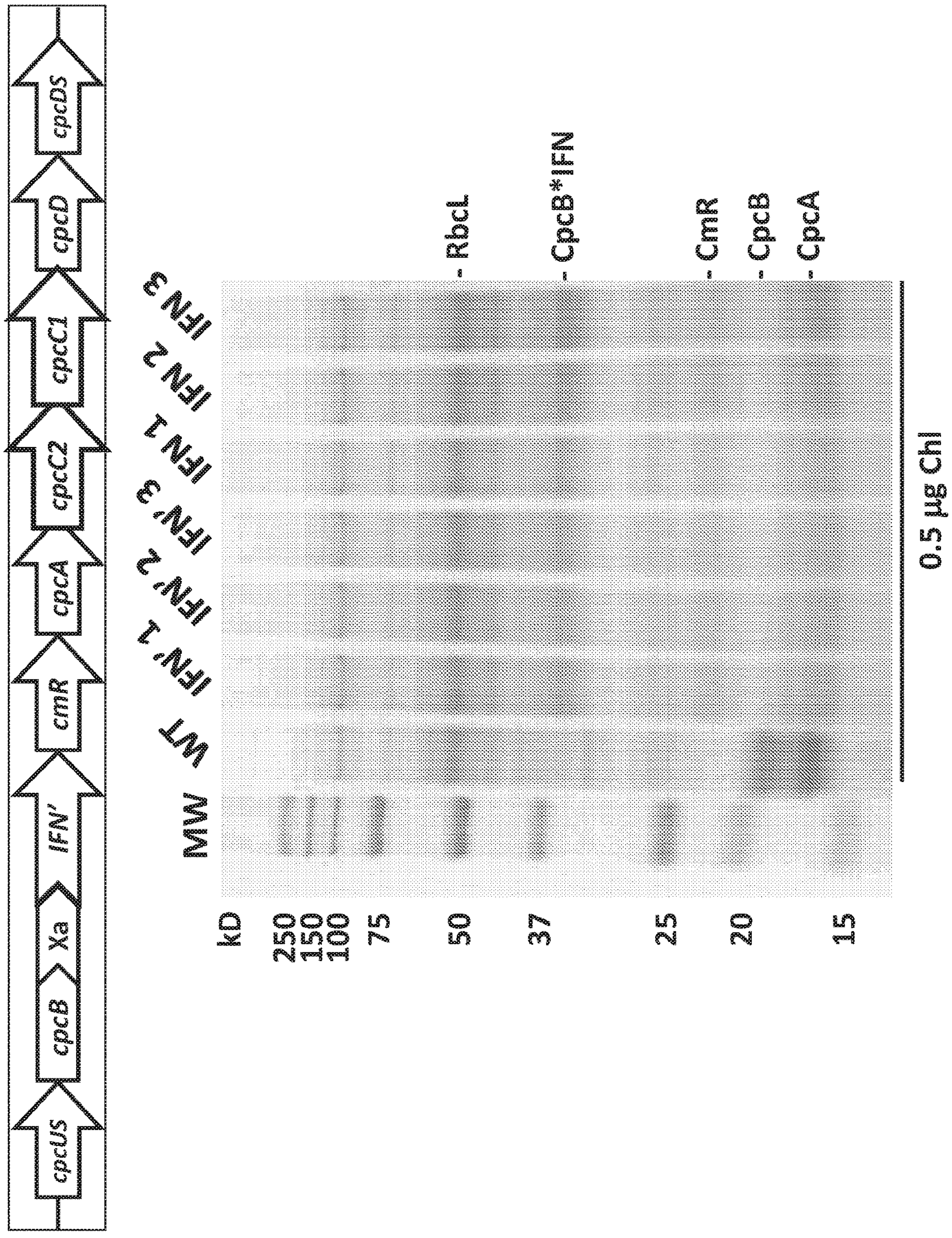
FIG. 5. Protein expression analysis of *Synechocystis* wild type (WT) and transformants harboring the cpcB*IFN fusion construct. Total cellular protein extracts were resolved by SDS-PAGE and visualized by Coomassie-stain. Two different versions of the IFN gene were used: the human native IFN' and the *Synechocystis* codon-optimized IFN gene. Note the presence of heterologous proteins migrating to ~36 kD (CpcB*IFN) and ~23 kD (CmR) in the transformants but not in the wild type. Also note the presence of the ~19 kD CpcB β-subunit and the ~17 kD CpcA α-subunit of phycocyanin in the wild type but not in the transformants. Sample loading corresponds to 0.5 μg of chlorophyll. Quantification of the CpcB*IFN protein accumulation relative to that of the Rubisco large subunit (RbcL) is given in the results of Table 1.

It is of interest that elution of the CpcB*His*Xa*IFN protein from the corresponding cell lysates showed a bluish coloration, which was attributed to the binding of the blue bilin to both the CpcB protein in the CpcB*His*Xa*IFN transformant and to the small amounts of the phycocyanin α-subunit present. Both of these apparently carry the tetrapyrrole chromophore, as evidenced by the typical phycocyanin absorbance spectra of these extracts (FIG. 9*a*) and by the Zn-staining of the proteins (FIG. 12). However, unlike the in vivo situation when about equal amounts of CpcB and CpcA are noted (FIG. 5, WT), there appeared to be no stoichiometry of CpcB*His*Xa*IFN and CpcA in the transformants (FIG. 5, IFN). The role of small amounts of CpcA in stabilizing the CpcB*His*Xa*IFN recombinant protein is not known at present.

Materials and Methods

*Synechocystis* Strains, Recombinant Constructs, and Culture Conditions.

The cyanobacterium *Synechocystis* sp. PCC 6803 (*Synechocystis*) was used as the experimental strain in this work and referred to as the wild type (WT). Gene sequences encoding the human interferon α-2 protein (referred to in the Examples as IFN) and human pro-insulin protein, both without the corresponding N-terminal signal peptides, were codon optimized for protein expression in *Synechocystis* using an open software system available on website, idtdna.com/CodonOpt. Gene sequence encoding the tissue plasminogen activator derivative K2S protein (sequence variable at www site drugbank.ca/drugs/DB00015) was codon optimized using the same above-cited open software. DNA constructs for *Synechocystis* transformation were synthesized by Biomatik USA (Wilmington, Del.). Sequences of the DNA constructs are shown in the Supplemental Materials.

*Synechocystis* transformations were carried out according to established protocols (Eaton-Rye, 2011; Williams, 1988; Lindberg et al., 2010). Wild type and transformants were maintained on BG11 media supplemented with 1% agar, 10 mM TES-NaOH (pH 8.2) and 0.3% sodium thiosulfate. Liquid cultures of BG11 were buffered with 25 mM sodium bicarbonate, pH 8.2, and 25 mM dipotassium hydrogen phosphate, pH 9, and incubated in the light upon slow continuous bubbling with air at 26° C. Transgenic DNA copy homoplasmy in the cells was achieved upon transformant incubation on agar in the presence of increasing concentrations of chloramphenicol (3-25 μg/mL). Growth of the cells was promoted by using a balanced combination of white LED bulbs supplemented with incandescent light to yield a final visible light (PAR) intensity of ~100 μmol photons $m^{-2}$ $s^{-1}$.

Genomic DNA PCR Analysis of *Synechocystis* Transformants.

Genomic DNA templates were prepared, as previously described (Formighieri and Melis, 2014a). A 20 μL culture aliquot was provided with an equal volume of 100% ethanol followed by brief vortexing. A 200 μL aliquot of a 10% (w/v) Chelex®100 Resin (BioRad) suspension in water was added to the sample prior to mixing and heating at 98° C. for 10 min to lyse the cells. Following centrifugation at 16,000 g for 10 min to pellet cell debris, 5 μL of the supernatant was used as a genomic DNA template in a 25 μL PCR reaction mixture. Q5® DNA polymerase (New England Biolabs) was used to perform the genomic DNA PCR analyses. Transgenic DNA copy homoplasmy in *Synechocystis* was tested using suitable primers listed in the Supplemental Materials. The genomic DNA location of these primers is indicated in FIG. 1 for the appropriate DNA constructs.

Protein Analysis

Cells in the mid exponential growth phase ($OD_{730}$~1) were harvested by centrifugation at 4,000 g for 10 min. The pellet was resuspended in a solution buffered with 25 mM Tris-HCl, pH 8.2, also containing a cOmplete™ mini protease inhibitor cocktail (Roche; one 50 mg tablet was added per 50 mL suspension). Cells were broken by passing the suspension through a French press cell at 1,500 psi. A slow speed centrifugation (350 g for 3 min) was applied to remove unbroken cells. For protein electrophoretic analysis, sample extracts were solubilized upon incubation for 1 h at room temperature in the presence of 125 mM Tris-HCl, pH 6.8, 3.5% SDS, 10% glycerol, 2 M urea, and 5% β-mercaptoethanol. SDS-PAGE was performed using Mini-PROTEAN TGX precast gels (BIORAD). Densitometric quantification of target proteins was performed using the BIORAD (Hercules, CA) Image Lab software. A subsequent Western blot analysis entailed transfer of the SDS-resolved proteins to a 0.1 μm pore size PVDF membrane (Life Technologies, Carlsbad, CA). Protein transfer to PVDF was followed by protein probing with rabbit-raised CpcA specific polyclonal antibodies (Abbiotec, San Diego, CA), as previously described (Formighieri and Melis, 2015;), or IFN-specific polyclonal antibodies (Abcam, Cambridge, MA).

Recombinant Protein Purification

Total cellular extracts (concentration 100 μg dcw $mL^{-1}$) from wild-type and transformant strains of *Synechocystis* were gently solubilized upon incubation with 1% Triton X-100 at 0° C. for 20 min. Solubilization of the extracts was conducted in an ice-water bath, upon gentle shaking. Following this solubilization treatment, samples were centrifuged at 10,000 g for 10 min to remove cell debris and insoluble material. His-Select resin (Sigma, Saint Louis, MO) was employed as a solid phase for protein binding and purification through cobalt affinity chromatography. Manufacturer's instructions were followed for both batch-type and column-based binding and purification. The washing solution was buffered with 20 mM Hepes, pH 7.5, and contained 150 mM NaCl and 10 mM imidazole to help remove non-target proteins. The elution solution was buffered with 20 mM Hepes, pH 7.5, and contained 150 mM NaCl and 250 mM imidazole to elute target protein from the resin.

Zn-Staining

SDS-PAGE was incubated in 5 mM zinc sulfate for 30 min X (Li et al. 2016). To detect covalent chromophore-binding polypeptides, zinc induced fluorescence was monitored by Chemidoc imaging system (BIORAD), employing UV light as a light source. Loading of total protein extracts was the same as for the Coomassie-stained SDS-PAGE.

Interferon Activity

Viruses replicate by co-opting normal host cell functions, turning cells into viral factories. Interferon protects cells by binding to extracellular receptors activating a cascade of signals that shuts down both de novo protein and DNA synthesis, depriving the invader the means to replicate. This puts the cells into a semi dormant state, preventing the production of new virus. This is most evident in the life cycle of lytic viruses which normally burst or lyse target cells, but fail to do so when cells are in an interferon-induced antiviral state. One can assess interferon activity by visually comparing the number of intact/lysed cells for a particular concentration of interferon added.

To assess interferon activity, we contracted the services of PBL Assay Science, Piscataway, NJ, USA, a commercial biomedical testing company, to impartially compare a commercially-available interferon against our own cyanobacterially-generated fusion IFN using the cytopathic effect (CPE) assay.

The PBL test entailed cells that were (1) untreated; (2) incubated with the encephalomyocarditis (EMC) virus alone; (3) pre-incubated with increasing concentrations of commercial interferon (provided by PBL Assay Science, Piscataway, N.J., USA); or (4) pre-incubated with our cyanobacteria-derived interferon at various concentrations of protein ranging from $1\times10^{-3}$ to $1\times10^{-7}$ μg/mL.

Samples were titrated in % well plates, and protection against the EMC virus was determined in comparison to the virus (no IFN) and cell (no virus) controls. The samples were run in duplicate alongside Human Interferon Alpha (INF-α) in a viral challenge assay using the encephalomyocarditis virus (EMC) on A549 human cells.

After maturation of the viral cytopathic effect (CPE), the live cells were fixed and stained using a mixture of 2 mL of 4% formaldehyde, 5% glycerol and 0.5% crystal violet stains per well and allowed to sit at for 60 min at room temperature. Plates were then washed 6-times in running water and dried upside down on filter paper. The dye was subsequently solubilized and assayed by absorbance readings at 570 nm.

All references, including publications, accession numbers, patent applications, and patents, cited herein are hereby incorporated by reference for the purpose for which it is cited to the same extent as if each reference were individually and specifically indicated to be incorporated by reference.

LISTING OF REFERENCES CITED BY IN SPECIFICATION BY AUTHOR, PUBLICATION YEAR

Baier T, Kros D, Feiner R C, Lauersen K J, Müller K M, Kruse O (2018) Engineered fusion proteins for efficient protein secretion and purification of a human growth factor from the green microalga *Chlamydomonas reinhardiii*. ACS Synth Biol. 7(11):2547-2557. doi: 10.1021/acssynbio.8b00226.

Bentley F K, Melis A (2012) Diffusion-based process for carbon dioxide uptake and isoprene emission in gaseous/aqueous two-phase photobioreactors by photosynthetic microorganisms. Biotech Bioeng 109:100-109 doi: 10.1002/bit.23298

Bentley F K, Garcia-Cerdán J G, Chen H-C, Melis A (2013) Paradigm of monoterpene (β-phellandrene) hydrocarbons production via photosynthesis in cyanobacteria. Bioenergy Res 6, 917-929. doi: 10.1007/s12155-013-9325-4

Bentley F K, Zurbriggen A, Melis A (2014) Heterologous expression of the mevalonic acid pathway in cyanobacteria enhances endogenous carbon partitioning to isoprene. Molecular Plant 7:71-86; doi:10.1093/mp/sst134

Betterle N, Melis A (2018) Heterologous leader sequences in fusion constructs enhance expression of geranyl diphosphate synthase and yield of β-phellandrene production in cyanobacteria (*Synechocystis*). ACS Synth Biol 7:912-921

Bis R L, Stauffer T M, Singh S M, Lavoie T B, Krishna M. G. Mallela K M G (2014) High yield soluble bacterial expression and streamlined purification of recombinant human interferon a-2a. Protein Expression and Purification 99, 138-146

Chaves J E, Rueda Romero P, Kirst H, Melis A (2016) Role of isopentenyl-diphosphate isomerase in heterologous cyanobacterial (*Synechocystis*) isoprene production. Photosynth Res 130:517-527. doi:10.1007/s11120-016-0293-3

Chaves J E, Melis A (2018) Biotechnology of cyanobacterial isoprene production. Appl Microbiol Biotechnol 102(15): 6451-6458

Chen H-C, Melis A (2013) Marker-free genetic engineering of the chloroplast in the green microalga *Chlamydomonas reinhardtii*. Plant Biotech J. 11, 818-828; DOI: 10.1111/pbi.12073

Clark E D (2001) Protein refolding for industrial processes. Curr Opin Biotechnol 12, 202-207

Coragliotti A T, Beligni M V, Franklin S E, Mayfield S P (2011) Molecular factors affecting the accumulation of recombinant proteins in the *Chlamydomonas reinhardtii* chloroplast. Mol Biotechnol 48:60-75

Dang B, Mravic M, Hu H. Schmidt N, Mensa B, DeGrado W F (2019) Nat Methods 16(4):319-322. doi: 10.1038/s41592-019-0357-3. Epub 2019 Mar. 25.

Demain A L, Vaishna P (2009) Production of recombinant proteins by microbes and higher organisms. Biotechnol. Adv. 27, 297-306

Desplancq D, Rinaldi A-S, Horzer H, Ho Y, Nierengarten H, R Andrew Atkinson R A, Kieffer B, Weiss E (2005) Combining inducible protein overexpression with NMR-grade triple isotope labeling in the cyanobacterium *Anabaena* sp. PCC 7120. BioTechniques 39, 405-411

Desplancq D, Rinaldi A-S. Horzer H, Ho Y, Nierengarten H, R. Andrew Atkinson R A, Kieffer B, Weiss E (2008) Automated overexpression and isotopic labelling of biologically active oncoproteins in the cyanobacterium *Anabaena* sp. PCC 7120. Biotechnol Appl Biochem 51, 53-61 doi:10.1042/BA20070276

Davies F K, Work V H, Beliaev A S, Posewitz M C (2014) Engineering limonene and bisabolene production in wild type and a glycogen-deficient mutant of *Synechococcus* sp. PCC7002. Front. Bioeng. Biotechnol. 2, 21.

Dyo Y M, Purton S (2018) The algal chloroplast as a synthetic biology platform for production of therapeutic proteins. Microbiol 164(2):113-121. doi: 10.1099/mic.0.000599.

Englund E, Shabestary K, Hudson E P, Lindberg P (2918) Systematic overexpression study to find target enzymes enhancing production of terpenes in *Synechocystis* PCC 6803, using isoprene as a model compound. Metab Eng. 49:164-177. doi: 10.1016/j.ymben.2018.07.004. Epub 2018 Jul. 17

Formighieri C, Melis A (2014a) Regulation of β-phellandrene synthase gene expression, recombinant protein accumulation, and monoterpene hydrocarbons production in *Synechocystis* transformants. Planta 240, 309-324. doi: 10.1007/s00425-014-2080-8

Gregory J A, Topol A B, Doemer D Z, Mayfield S (2013) Alga-produced cholera toxin-Pfs25 fusion proteins as oral vaccines. Appl Environ Microbiol 79:3917-3925.

Halfmann C. Gu L, Zhou R (2014a) Engineering cyanobacteria for the production of a cyclic hydrocarbon fuel from $CO_2$ and $H_2O$. Green Chem. 16, 3175-3185

Halfmann C, Gu L, Gibbons W, Ruanbao Zhou R (2014b) Genetically engineering cyanobacteria to convert $CO_2$, water, and light into the long-chain hydrocarbon famesene. Appl Microbiol Biotechnol 98:9869-9877

Hidalgo D, Abdoli-Nasab M, Jalali-Javaran M, Bru-Martinez R. Cusido R M, Corchete P, Palazon J (2017) Biotechnological production of recombinant tissue plasminogen activator protein (reteplase) from transplastomic tobacco cell cultures. Plant Physiol Biochem 118, 130-137. http://dx.doi.org/10.1016/j.plaphy.2017.06.013

Kondo K, Geng X, Katayama M. Ikeuchi M (2005) Distinct roles of CpcG1 and CpcG2 in phycobilisome assembly in the cyanobacterium *Synechocystis* sp. PCC 6803. Photosyn Res
84:269-73

Jindou S, Ito Y, Mito N, Uematsu K. Hosoda A, Tamura H (2014) Engineered platform for bioethylene production by a cyanobacterium expressing a chimeric complex of plant enzymes. *ACS Synth. Biol.* 37, 487-496

Jones C S, Mayfield S P (2013) Steps toward a globally available malaria vaccine: harnessing the potential of algae for future low cost vaccines. Bioengineered 4:164-167

Kosobokova E N, Skrypnik K A, Kosorukov V S (2016) Overview of fusion tags for recombinant proteins. Biochemistry (Mosc). 81(3):187-200. doi: 10.1134/S0006297916030019.

Lin Y, Garvey C J, Birch D, Corkery R W, Loughlin P C, Scheer H, Willows R D, Chen M (2016) Characterization of red-shifted phycobilisomes isolated from the chlorophyll f-containing cyanobacterium *Halomicronema hongdechloris*. Biochim Biophys Acta. 1857, 107-114

Lindberg P, Park S, Melis A (2010) Engineering a platform for photosynthetic isoprene production in cyanobacteria, using *Synechocystis* as the model organism. Metab Eng 12:70-79. doi: 10.1016/j.ymben.2009.10.001

Luo X-G, Tian W-J, Ni M, Jing X-L, Lv L-H, Wang N, Jiang Y, Zhang T-C (2011) Soluble expression of active recombinant human tissue plasminogen activator derivative (K2S) in *Escherichia coli*. Pharmaceutical Biology 49:653-657

Nordt T K, Bode C (200). Thrombolisys: newer trombolytic agents and their role in clinical medicine. Hearth 89, 1358-1362

Parkin J, Cohen B (2001) An overview of the immune system. *Lancet.* 357 (9270): 1777-1789. doi:10.1016/S0140-6736(00)04904-7

Qin D, Fredrick K (2013) Analysis of polysomes from bacteria. Methods Enzymol 530:159-172

Qiu J I, Swartz J R, Georgiou G (1998) Expression of active human tissue-type plasminogen activator in *Escherichia coli.* Appl Environ Microbiol 64:4891-4896

Rasala B A, Mayfield S P (2015) Photosynthetic biomanufacturing in green algae; production of recombinant proteins for industrial, nutritional, and medical uses. Photosynth Res 123:227-239

Sonksen P, Sonksen J (2000) Insulin understanding its action in health and disease. British Journal of Anaesthesia 85(1): 69-79 doi:10.1093/bja/85.1.69. PMID 10927996

Stryer L (1995) Biochemistry (Fourth ed.). New York: W.H. Freeman and Company. pp. 773-774. ISBN 0 7167 2009 4

Surzycki R, Greenham K, Kitayama K, Dibal F, Wagner R, Rochaix J-D, Ajam T. Surzycki S (2009) Factors effecting expression of vaccines in microalgae. Biologicals 37:133-138

Tran M, Zhou B, Pettersson P L, Gonzalez M J, Mayfield S P (2009) Synthesis and assembly of a full-length human monoclonal antibody in algal chloroplasts. Biotechnol Bioeng 104:663-673.

Ungerer J, Tao L, Davis M, Ghirardi M. Maness P-C. Yu J (2012) Sustained photosynthetic conversion of $CO_2$ to ethylene in recombinant cyanobacterium *Synechocystis* 6803. Energy Environ Sci 5:8998-9006

Vijay D, M Akhtar, M K, Hess W R (2019) Genetic and metabolic advances in the engineering of cyanobacteria. Current Opinion in Biotechnology 59:150-156.

Voet D, Voet J G (2011) *Biochemistry* (4th ed.). New York: Wiley.

Wilson S A, Roberts S C (2012) Recent advances towards development and commercialization of plant cell culture processes for the synthesis of biomolecules. Plant Biotech. J. 10, 249-268.

Xiong W. Morgan J A, Ungerer J, Wang B. Maness P-C, Yu J (2015) The plasticity of cyanobacterial metabolism supports direct $CO_2$ conversion to ethylene. Nature Plants 1, Article Number 15053.

Youchun Z, Ge W, Kong Y, Zhang C (2003) Cloning, expression and renaturation studies of reteplase. J. Microbiol. Biotechnol. 13 (6), 989-992.

Zhou J. Zhang H, MengH, Zhu Y, Bao G, Zhang Y, Li Y, Ma Y (2014) Discovery of a super-strong promoter enables efficient production of heterologous proteins in cyanobacteria. Scientific Rep 4(1), 4500

TABLE 1

Quantification of the RbcL and CpcB*IFN fusion proteins as percent of the total Synechocystis proteins loaded onto the SDS-PAGE lanes of FIG. 5. RbcL levels were measured to account for ~12.5% ± 0.5, CpcB*IFN' accounted for 10.2% ± 0.2, whereas the CpcB*IFN accounted for 11.8% ± 0.1 of the total cellular proteins.

| Protein measured | IFN' 1 | IFN' 2 | IFN' 3 | IFN 1 | IFN 2 | IFN 3 |
|---|---|---|---|---|---|---|
| RbcL | 12.1 | 12.4 | 13.2 | 11.9 | 12.9 | 12.6 |
| CpcB*IFN | 10.4 | 9.9 | 10.2 | 11.8 | 11.9 | 11.7 |

ILLUSTRATIVE SEQUENCES

SEQ ID NO:1 Human Interferon Alpha-2 (165 Amino Acids in Length)

CDLPQTHSLGSRRTLMLLAQMRKISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE

SEQ ID NO:2 Human Tissue-Type Plasminogen Activator (562 Amino Acids in Length). The signal peptide is underlined.

MDAMKRGLCCVLLLCGAVFVSPSQEIHARFRRGARSYQVICRDEKTQMIY

QQHQSWLRPVLRSNRVEYCWCNSGRAQCHSVPVKSCSEPRCFNGGTCQQA

LYFSDFVCQCPEGFAGKCCEIDTRATCYEDQGISYRGTWSTAESGAECTN

WNSSALAQKPYSGRRPDAIRLGLGNHNYCRNPDRDSKPWCYVFKAGKYSS

EFCSTPACSEGNSDCYFGNGSAYRGTHSLTESGASCLPWNSMILIGKVYT

AQNPSAQALGLGKHNYCRNPDGDAKPWCHVLKNRRLTWEYCDVPSCSTCG

LRQYSQPQFRIKGGLFADIASHPWQAAIFAKHRRSPGERFLCGGILISSC

WILSAAHCFQERFPPHHLTVILGRTYRVVPGEEEQKFEVEKYIVHKEFDD

DTYDNDIALLQLKSDSSRCAQESSVVRTVCLPPADLQLPDWTECELSGYG

KHEALSPFYSERLKEAHVRLYPSSRCTSQHLLNRTVTDNMLCAGDTRSGG

PQANLHDACQGDSGGPLVCLNDGRMTLVGIISWGLGCGQKDVPGVYTKVT

NYLDWIRDNMRP

SEQ ID NO:3 Truncated Human Tissue Plasminogen Activator (K(2S Reteplase) Amino Acid Sequence (355 Amino Acids in Length)

SYQGNSDCYFGNGSAYRGTHSLTESGASCLPWNSMILIGKVYTAQNPSAQ

ALGLGKHNYCRNPDGDAKPWCHVLKNRRLTWEYCDVPSCSTCGLRQYSQP

QFRIKGGLFADIASHPWQAAIFAKHRRSPGERFLCGGILISSCWILSAAH

CFQERFPPHHLTVILGRTYRVVPGEEEQKFEVEKYIVHKEFDDDTYDNDI

ALLQLKSDSSRCAQESSVVRTVCLPPADLQLPDWTECELSGYGKHEALSP

FYSERLKEAHVRLYPSSRCTSQHLLNRTVTDNMLCAGDTRSGGPQANLHD

ACQGDSGGPLVCLNDGRMTLVGIISWGLGCGQKDVPGVYTKVTNYLDWIR

DNMRP

SEQ ID NO:4 Human Pro-Insulin Amino Acid Sequence (86 Amino Acids in Length)

FVNQHLCGSHLVEALYLVCGERGFFYTPKTRREAEDLQVGQVELGGGPGA

GSLQPLALEGSLQKRGIVEQCCTSICSLYQLENYCN

SEQ ID NO: 15 TTFC, Tetanus Toxin Fragment C (451 Amino Acids in Length)

KNLDCWVDNEEDIDVILKKSTILNLDINNDHISDISGFNSSVITYPDAQL

VPGINGKAIHLVNNESSEVIVHKAMDIEYNDMFNNFTVSFWLRVPKVSAS

HLEQYDTNEYSIISSMKKYSLSIGSGWSVSLKGNNLIWTLKDSAGEVRQI

-continued

TFRDLSDKFNAYLANKWVFITITNDRLSSANLYINGVLMGSAEITGLGAI
REDNNITLKLDRCNNNNQYVSIDKFRIFCKALNPKEIEKLYTSYLSITFL
RDFWGNPLRYDTEYYLIPVAYSSKDVQLKNITDYMYLTNAPSYTNGKLNI
YYRRLYSGLKFIIKRYTPNNEIDSFVRSGDFIKLYVSYNNNEHIVGYPKD
GNAFNNLDRILRVGYNAPGIPLYKKMEAVKLRDLKTYSVQLKLYDDKDAS
LGLVGTHNGQIGNDPNRDILIASNWYFNHLKDKTLTCDWYFVPTDEGWTN
D

SEQ ID NO: 16 Receptor Binding Domain (RBD) of the S1-spike protein from the SARS-CoV-2 virus (223 amino acids in length)

RVQPTESIVRFPNITNLCPFGEVFNATRFASVYAWNRKRISNCVADYSVL
YNSASFSTFKCYGVSPTKLNDLCFTNVYADSFVIRGDEVRQIAPGQTGKI
ADYNYKLPDDFTGCVIAWNSNNLDSKVGGNYNYLYRLFRKSNLKPFERDI
STEIYQAGSTPCNGVEGFNCYFPLQSYGFQPTNGVGYQPYRVVVLSFELL
HAPATVCGPKKSTNLVKNKCVNF

SEQ ID NO: 17 the S1-Spike Protein from the SARS-CoV-2 Virus (673 Amino Acids in Length SQCVNLTTRTQLPPAYTNSFTRGVYYPDKVFRSSVLHSTQDLFLPFFSNV
TWFHAIHVSGTNGTKRFDNPVLPFNDGVYFASTEKSNIIRGWIFGTTLDS -continued KTQSLLIVNNATNVVIKVCEFQFCNDPFLGVYYHKNNKSWMESEFRVYSS
ANNCTFEYVSQPFLMDLEGKQGNFKNLREFVFKNIDGYFKIYSKHTPINL
VRDLPQGFSALEPLVDLPIGINITRFQTLLALHRSYLTPGDSSSGWTAGA
AAYYVGYLQPRTFLLKYNENGTITDAVDCALDPLSETKCTLKSFTVEKGI
YQTSNFRVQPTESIVRFPNITNLCPFGEVFNATRFASVYAWNRKRISNCV
ADYSVLYNSASFSTFKCYGVSPTKLNDLCFTNVYADSFVIRGDEVRQIAP
GQTGKIADYNYKLPDDFTGCVIAWNSNNLDSKVGGNYNYLYRLFRKSNLK
PFERDISTEIYQAGSTPCNGVEGFNCYFPLQSYGFQPTNGVGYQPYRVVV
LSFELLHAPATVCGPKKSTNLVKNKCVNFNFNGLTGTGVLTESNKKFLPF
QQFGRDIADTTDAVRDPQTLEILDITPCSFGGVSVITPGTNTSNQVAVLY
QDVNCTEVPVAIHADQLTPTWRVYSTGSNVFQTRAGCLIGAEHVNNSYEC
DIPIGAGICASYQTQTNSPRRAR SEQ ID NO: 18 CtxB, Cholera Toxin B (103 Amino Acids in Length)

TPQNITDLCAEYHNTQIHTLNDKIFSYTESLAGKREMAIITFKNGATFQV
EVPGSQHIDSQKKAIERMKDTLRIAYLTEAKVEKLCVWNNKTPHAIAAIS
MAN

ILLUSTRATIVE EXPRESSION CONSTRUCT SEQUENCES

1. *cpc_us . . . optIFN-cmR . . . cpcA* construct (see, FIG. 1, panel B)
CTCGAG - XhoI DNA restriction site
AGATCT - BglII DNA restriction site
*GGATCC* - BamHI DNA restriction site
*Lower case* - *cpc* upstream
5' RECOMBINATION
UPPER CASE - Codon-optimized human interferon (501 nt)
lower case - intergenic sequence in construct
lower case bold - *cmR*
<u>lower case underlined</u> - Transcription terminator
3' RECOMBINATION
*lower case italics* - *cpcB-cpcA* intergenic sequence
lower case bold - *cpcA* (partial)

**SEQ ID NO: 5 *cpc_us...optIFN-cmR...cpcA* (2336 nt) nucleic acid sequence**
CTCGAG*taggctgtggttccctaggcaacagtcttccctaccccactggaaactaaaaaaacgagaaaagttcgcaccgaa*
*catcaattgcataattttagccctaaaacataagctgaacgaaactgg+tgtcttcccttcccaatccaggacaatctgagaatcccc*
*tgcaacattacttaacaaaaaagcaggaataaaattaacaagatgtaacagacataagtcccatcaccgttgtataaagttaact*
*gtgggattgcaaaagcattcaagcctaggcgctgagctgtttgagcatcccggtggcccttgtcgctgcctccgtgtttctccctggat*
*ttatttaggtaatatctctcataaatccccgggtagttaacgaaagttaatggagatcagtaacaataactctagggtcattactttgg*
*actccctcagtttatccgggggaattgtgtttaagaaaatcccaactcataaagtcaagtaggagattaattca*AAGTGTGA
CTTGCCTCAGACGCATTCTTTGGGAAGCCGACGCACACTGATGCTGCTCGCCCAA
ATGCGCCGGATCTCCTTATTCTCCTGTCTCAAGGATCGGCATGACTTCGGCTTCCC
TCAGGAGGAGTTTGGAAATCAGTTCCAAAAGGCCGAAACCATTCCGGTCCTCCAT
GAAATGATTCAACAGATCTTTAACTTATTCAGTACCAAAGACAGCAGTGCGGCCT
GGGACGAAACATTACTCGATAAATTCTACACGGAATTATACCAACAGTTGAACG
ACTTAGAAGCCTGTGTAATCCAAGGTGTTGGTGTCACTGAGACTCCATTAATGAA
AGAAGACTCTATTCTGGCCGTCCGCAAGTATTTCCAGCGAATCACACTGTATTTG
AAAGAGAAAAAGTATTCTCCGTGTGCGTGGGAGGTAGTACGGGCTGAAATCATG
CGGTCCTTCTCTTTAAGCACAAACCTCCAGGAATCTCTGCGCTCCAAAGAATGAA
GATCTgcggccgcgttgatcggcacgtaagaggttccaactttcaccataatgaaataagatcactaccgggcgtatttttgagtta
tcgagattttcaggagctaaggaagctaaaatggagaaaaaaatcactggatataccaccgttgatatatcccaatggcatcgta
aagaacattttgaggcatttcagtcagttgctcaatgtacctataaccagaccgttcagctggatattacggcctttttaaagacc
gtaaagaaaaataagcacaagttttatocggcctttattcacattcttgcccgcctgatgaatgctcatccggaattccgtatgg
caatgaaagacggtgagctggtgatatgggatagtgttcacccttgttacaccgttttccatgagcaaactgaaacgttttcatc
gctctggagtgaataccacgacgatttccggcagtttctacacatatattcgcaagatgtggcgtgttacggtgaaaacctggc
ctatttccctaaagggtttattgagaatatgtttttcgtctcagccaatccctgggtgagtttcaccagttttgatttaaacgtggcc
aatatggacaacttcttcgcccccgttttcaccatgggcaaatattatacgcaaggcgacaaggtgctgatgccgctggcgatt
caggttcatcatgccgtctgtgatggcttccatgtcggcagaatgcttaatgaattacaacagtactgcgatgagtggcagggc

-continued ggggcgtaatttttttaaggcagttattggtgcccttaaacgcctgg*GGATCCtctggttattttaaaaaccaactttactcaggttcc*
*atacccgagaaaatccagcttaaagctgacatatctaggaaaattttcacattctaacgggagataccagaaca*atgaaaacc
ctttaactgaagccgtttccaccgctgactctcaaggtcgctttctgagcagcaccgaattgcaaattgctttcggtcgtctacgt
caagctaatgctggtttgcaagccgctaaagctctgaccgacaatgcccagagcttggtaaatggtgctgcccaagccgtttat
aacaaattcccctacaccacccaaacccaaggcaacaactttgctgcggatcaacggggtaaagacaagtgtgcccgggac
atcggctactacctccgcatcgttacctactgcttagttgctggtggtaccggtcctttggatgagtacttgatcgccggtattgat
gaaatcaaccgcacctttgacctctcccccagctggtatgttCTCGAG 2. *cpcB . . . optIFN-cmR . . . cpcA* construct (see, FIG. 1, panel C):

CTCGAG - XhoI DNA restriction site
AGATCT - BglII DNA restriction site
*GGATCC* - BamHI DNA restriction site
Lower case - partial *cpcB*
UPPER CASE - intergenic sequence *cpcB-cpcA*
5' RECOMBINATION
UPPER CASE - Codon-optimized human interferon (501 nt)
lower case - intergenic sequence
lower case bold - *cmR*
lower case underlined - Transcription terminator
3' RECOMBINATION
*lower case italics* - *cpcB-cpcA* intergenic sequence
lower case bold - *cpcA* (partial)

SEQ ID NO: 6 cpcB . . . optIFN-cmR . . . cpcA (2340 nt) nucleic acid sequence

CTCGAGccgcatcaccggtaatgcttccgctatcgtttccaacgctgctcgtgctttgttcgccgaacagccccaattaatccaacc
cggtggaaacgcctacaccagccgtcgtatggctgcttgtttgcgtgacatggaaatcatcctccgctatgttacctacgcaaccttcac
cggcgacgcttccgttctagaagatcgttgcttgaacggtctccgtgaaacctacgttgccctgggtgttcccggtgcttccgtagctgct
ggcgttcaaaaaatgaaagaagctgccctggacatcgttaacgatcccaatggcatcacccgtggtgattgcagtgctatcgttgctga
aatcgctggttacttcgaccgcgccgctgctgccgtagcctagTCTGGTTATTTTAAAAACCAACTTTAC
TCAGGTTCCATACCCGAGAAAATCCAGCTTAAAGCTGACATATCTAGGAAAA
TTTTCACATTCTAACGGGAGATACCAGAACAATGTGTGACTTGCCTCAGACGC
ATTCTTTGGGAAGCCGACGCACACTGATGCTGCTCGCCCAAATGCGCCGGATCTC
CTTATTCTCCTGTCTCAAGGATCGGCATGACTTCGGCTTCCCTCAGGAGGAGTTTG
GAAATCAGTTCCAAAAGGCCGAAACCATTCCGGTCCTCCATGAAATGATTCAAC
AGATCTTTAACTTATTCAGTACCAAAGACAGCAGTGCGGCCTGGGACGAAACATT
ACTCGATAAATTCTACACGGAATTATACCAACAGTTGAACGACTTAGAAGCCTGT
GTAATCCAAGGTGTTGGTGTCACTGAGACTCCATTAATGAAAGAAGACTCTATTC
TGGCCGTCCGCAAGTATTTCCAGCGAATCACACTGTATTTGAAAGAGAAAAAGT
ATTCTCCGTGTGCGTGGGAGGTAGTACGGGCTGAAATCATGCGGTCCTTCTCTTT
AAGCACAAACCTCCAGGAATCTCTGCGCTCCAAAGAATGAAGATCTgcggccgcgttga
tcggcacgtaagaggttccaactttcaccataatgaaataagatcactaccgggcgtatttttttgagttatcgagattttcaggagctaagg
aagctaaaatggagaaaaaaatcactggatataccaccgttgatatatcccaatggcatcgtaaagaacattttgaggcatttc
agtcagttgctcaatgtacctataaccagaccgttcagctggatattacggcctttttaaagaccgtaaagaaaaataagcaca
agttttatccggcctttattcacattcttgcccgcctgatgaatgctcatccggaattccgtatggcaatgaaagacggtgagctg
gtgatatgggatagtgttcacccttgttacaccgttttccatgagcaaactgaaacgttttcatcgctctggagtgaataccacga
cgatttccggcagtttctacacatatattcgcaagatgtggcgtgttacggtgaaaacctggcctatttccctaaagggtttattg
agaatatgtttttcgtctcagccaatccctgggtgagtttcaccagttttgatttaaacgtggccaatatggacaacttcttcgccc
ccgttttcaccatgggcaaatattatacgcaaggcgacaaggtgctgatgccgctggcgattcaggttcatcatgccgtctgtg
atggcttccatgtcggcagaatgcttaatgaattacaacagtactgcgatgagtggcagggcgggcgtaatttttttaaggcagt
tattggtgcccttaaacgcctgg*GGATCCtctggttattttaaaaaccaactttactcaggttccatacccgagaaaatccagctta*
*aagctgacatatctaggaaaattttcacattctaacgggagataccagaaca*atgaaaacccctttaactgaagccgtttccacc
gctgactctcaaggtcgctttctgagcagcaccgaattgcaaattgctttcggtcgtctacgtcaagctaatgctggtttgcaagc
cgctaaagctctgaccgacaatgcccagagcttggtaaatggtgctgcccaagccgtttataacaaattcccctacaccaccca
aacccaaggcaacaactttgctgcggatcaacggggtaaagacaagtgtgcccgggacatcggctactacctccgcatcgtt
acctactgcttagttgctggtggtaccggtcctttggatgagtacttgatcgccggtattgatgaaatcaaccgcacctttgacct
ctcccccagctggtatgttCTCGAG 3. *cpc us . . . cpcB*Xa*IFN-cmR . . . cpcA* construct (see, FIG. 1, panel D):

CTCGAG - XhoI DNA restriction site
AGATCT - BglII DNA restriction site
*GGATCC* - BamHI DNA restriction site
Lower case - *cpcB*
5' RECOMBINATION
UPPER CASE - Factor Xa cleavage site (IEGR)
UPPER CASE - codon-optimized human interferon
lower case - intergenic sequence
lower case bold - cmR
lower case underline - Transcription terminator
3' RECOMBINATION
*lower case italics* - *cpcB-cpcA* intergenic sequence
lower case bold - *cpcA* (partial)

SEQ ID NO: 7 ***cpc us...cpcB*Xa*IFN-cmR...cpcA* (2361 nt) nucleic aic squence**

CTCGAGatgttcgacgtattcactcgggttgtttcccaagctgatgctcgcggcgagtacctctctggttctcagttagatgctttgag
cgctaccgttgctgaaggcaacaaacggattgattctgttaaccgcatcaccggtaatgcttccgctatcgtttccaacgctgctcgtgct
ttgttcgccgaacagccccaattaatccaacccggtggaaacgcctacaccagccgtcgtatggctgcttgtttgcgtgacatggaaat
catcctccgctatgttacctacgcaaccttcaccggcgacgcttccgttctagaagatcgttgcttgaacggtctccgtgaaacctacgtt
gccctgggtgttcccggtgcttccgtagctgctggcgttcaaaaaatgaaagaagctgccctggacatcgttaacgatcccaatggcat
cacccgtggtgattgcagtgctatcgttgctgaaatcgctggttacttcgaccgcgccgctgctgccgtagccATCGAAGGGC
GATGTGACTTGCCTCAGACGCATTCTTTGGGAAGCCGACGCACACTGATGCTGCT
CGCCCAAATGCGCCGGATCTCCTTATTCTCCTGTCTCAAGGATCGGCATGACTTC
GGCTTCCCTCAGGAGGAGTTTGGAAATCAGTTCCAAAAGGCCGAAACCATTCCG
GTCCTCCATGAAATGATTCAACAGATCTTTAACTTATTCAGTACCAAAGACAGCA -continued GTGCGGCCTGGGACGAAACATTACTCGATAAATTCTACACGGAATTATACCAAC
AGTTGAACGACTTAGAAGCCTGTGTAATCCAAGGTGTTGGTGTCACTGAGACTCC
ATT AATGAAAGAAGACTCTATTCTGGCCGTCCGCAAGTATTTCCAGCGAATCACA
CTGTATTTGAAAGAGAAAAAGTATTCTCCGTGTGCGTGGGAGGTAGTACGGGCT
GAAATCATGCGGTCCTTCTCTTTAAGCACAAACCTCCAGGAATCTCTGCGCTCCA
AAGAATGAAGATCTgcggccgcgttgatcggcacgtaagaggttccaactttcaccataatgaaataagatcactaccgg
gcgtatttttttgagttatcgagattttcaggagctaaggaagctaaaatggagaaaaaaatcactggatataccaccgttgatatatc
ccaatggcatcgtaaagaacattttgaggcatttcagtcagttgctcaatgtacctataaccagaccgttcagctggatattacg
gcctttttaaagaccgtaaagaaaaataagcacaagttttatccggcctttattcacattcttgcccgcctgatgaatgctcatcc
ggaattccgtatggcaatgaaagacggtgagctggtgatatgggatagtgttcacccttgttacaccgttttccatgagcaaact
gaaacgttttcatcgctctggagtgaataccacgacgatttccggcagtttctacacatatattcgcaagatgtggcgtgttacg
gtgaaaacctggcctatttccctaaagggtttattgagaatatgtttttcgtctcagccaatccctgggtgagtttcaccagttttg
atttaaacgtggccaatatggacaacttcttcgcccccgttttcaccatgggcaaatattatacgcaaggcgacaaggtgctga
tgccgctggcgattcaggttcatcatgccgtctgtgatggcttccatgtcggcagaatgcttaatgaattacaacagtactgcga
tgagtggcagggcggggcgtaatttttttaaggcagttattggtgcccttaaacgcctgg*GGATCCtctggttattttaaaaacca*
*actttactcaggttccatacccgagaaaatccagcttaaagctgacatatctaggaaaattttcacattctaacgggagataccaga*
*aca*atgaaaacccctttaactgaagccgtttccaccgctgactctcaaggtcgctttctgagcagcaccgaattgcaaattgctt
tcggtcgtctacgtcaagctaatgctggtttgcaagccgctaaagctctgaccgacaatgcccagagcttggtaaatggtgctg
cccaagccgtttataacaaattcccctacaccacccaaacccaaggcaacaactttgctgcggatcaacggggtaaagacaa
gtgtgcccgggacatcggctactacctccgcatcgttacctactgcttagttgctggtggtaccggtcctttggatgagtacttga
tcgccggtattgatgaaatcaaccgcacctttgacctctcccccagctggtatgttCTCGAG 4. *cpc us . . . cpcB*Xa*IFN'-cmR . . . cpcA* construct (see, FIG. 5):
CTCGAG - XhoI DNA restriction site
AGATCT - BglII DNA restriction site
*GGATCC* - BamHI DNA restriction site
Lower case - *cpcB*
5' RECOMBINATION
UPPER CASE - Factor Xa cleavage site (IEGR)
UPPER CASE - Native human interferon
lower case - intergenic sequence in Cinzia's construct
lower case bold - *cmR*
lower case underlined - Transcription terminator
3' RECOMBINATION
*lower case italics* - *cpcB-cpcA* intergenic sequence
lower case bold - *cpcA* (partial)
SEQ ID NO: 8 ***cpc us...cpcB*Xa*IFN-cmR...cpcA* (2361 nt) nucleic acid sequence**
CTCGAGatgttcgacgtattcactcgggttgtttcccaagctgatgctcgcggcgagtacctctctggttctcagttagatgctttgag
cgctaccgttgctgaaggcaacaaacggattgattctgttaaccgcatcaccggtaatgcttccgctatcgtttccaacgctgctcgtgct
ttgttcgccgaacagccccaattaatccaacccggtggaaacgcctacaccagccgtcgtatggctgcttgtttgcgtgacatggaaat
catcctccgctatgttacctacgcaaccttcaccggcgacgcttccgttctagaagatcgttgcttgaacggtctccgtgaaacctacgtt
gccctgggtgttcccggtgcttccgtagctgctggcgttcaaaaaatgaaagaagctgccctggacatcgttaacgatcccaatggcat
cacccgtggtgattgcagtgctatcgttgctgaaatcgctggttacttcgaccgcgccgctgctgccgtagccATCGAAGGGC
GATGTGATCTGCCTCAAACCCACAGCCTGGGTAGCAGGAGGACCTTGATGCTCCT
GGCACAGATGAGGAGAATCTCTCTTTTCTCCTGCTTGAAGGACAGACATGACTTT
GGATTTCCCCAGGAGGAGTTTGGCAACCAGTTCCAAAAGGCTGAAACCATCCCT
GTCCTCCATGAGATGATCCAGCAGATCTTCAATCTCTTCAGCACAAAGGACTCAT
CTGCTGCTTGGGATGAGACCCTCCTAGACAAATTCTACACTGAACTCTACCAGCA
GCTGAATGACCTGGAAGCCTGTGTGATACAGGGGGTGGGGGTGACAGAGACTCC
CCTGATGAAGGAGGACTCCATTCTGGCTGTGAGGAAATACTTCCAAAGAATCACT
CTCTATCTGAAAGAGAAGAAATACAGCCCTTGTGCCTGGGAGGTTGTCAGAGCA
GAAATCATGAGATCTTTTTCTTTGTAACAAACTTGCAAGAAAGTTTAAGAAGTA
AGGAATGAAGATCTgcggccgcgttgatcggcacgtaagaggttccaactttcaccataatgaaataagatcactaccgg
gcgtatttttttgagttatcgagattttcaggagctaaggaagctaaaatggagaaaaaaatcactggatataccaccgttgatatatc
ccaatggcatcgtaaagaacattttgaggcatttcagtcagttgctcaatgtacctataaccagaccgttcagctggatattacg
gcctttttaaagaccgtaaagaaaaataagcacaagttttatccggcctttattcacattcttgcccgcctgatgaatgctcatcc
ggaattccgtatggcaatgaaagacggtgagctggtgatatgggatagtgttcacccttgttacaccgttttccatgagcaaact
gaaacgttttcatcgctctggagtgaataccacgacgatttccggcagtttctacacatatattcgcaagatgtggcgtgttacg
gtgaaaacctggcctatttccctaaagggtttattgagaatatgtttttcgtctcagccaatccctgggtgagtttcaccagttttg
atttaaacgtggccaatatggacaacttcttcgcccccgttttcaccatgggcaaatattatacgcaaggcgacaaggtgctga
tgccgctggcgattcaggttcatcatgccgtctgtgatggcttccatgtcggcagaatgcttaatgaattacaacagtactgcga
tgagtggcagggcggggcgtaatttttttaaggcagttattggtgcccttaaacgcctgg*GGATCCtctggttattttaaaaacca*
*actttactcaggttccatacccgagaaaatccagcttaaagctgacatatctaggaaaattttcacattctaacgggagataccaga*
*aca*atgaaaacccctttaactgaagccgtttccaccgctgactctcaaggtcgctttctgagcagcaccgaattgcaaattgctt
tcggtcgtctacgtcaagctaatgctggtttgcaagccgctaaagctctgaccgacaatgcccagagcttggtaaatggtgctg
cccaagccgtttataacaaattcccctacaccacccaaacccaaggcaacaactttgctgcggatcaacggggtaaagacaa
gtgtgcccgggacatcggctactacctccgcatcgttacctactgcttagttgctggtggtaccggtcctttggatgagtacttga
tcgccggtattgatgaaatcaaccgcacctttgacctctcccccagctggtatgttCTCGAG 5. *cpc us . . . cpcB*HisTag*Xa*IFN-cmR . . . cpcA* construct (see, FIG. 6):
CTCGAG - XhoI DNA restriction site
AGATCT - BglII DNA restriction site
*GGATCC* - BamHI DNA restriction site
Lower case - *cpcB*
5' RECOMBINATION
UPPER CASE - Histag 6x
UPPER CASE - Factor Xa cleavage site (IEGR)
UPPER CASE - synechocystis-optimized human interferon
lower case - intergenic sequence in Cinzia's construct
lower case bold - cmR
lower case underlined - Transcription terminator -continued

3' RECOMBINATION
*lower case italics* - *cpcB-cpcA* intergenic sequence
lower case bold - *cpcA* (partial)
SEQ ID NO: 9 *cpc us . . . cpcB*HisTag*Xa*IFN-cmR . . . cpcA* (2379 nt) nucleic acid sequence CTCGAGatgttcgacgtattcactcgggttgtttcccaagctgatgctcgcggcgagtacctctctggttctcagttagatgctttgag
cgctaccgttgctgaaggcaacaaacggattgattctgttaaccgcatcaccggtaatgcttccgctatcgtttccaacgctgctcgtgct
ttgttcgccgaacagccccaattaatccaacccggtggaaacgcctacaccagccgtcgtatggctgcttgtttgcgtgacatggaaat
catcctccgctatgttacctacgcaaccttcaccggcgacgcttccgttctagaagatcgttgcttgaacggtctccgtgaaacctacgtt
gccctgggtgttcccggtgcttccgtagctgctggcgttcaaaaaatgaaagaagctgccctggacatcgttaacgatcccaatggcat
cacccgtggtgattgcagtgctatcgttgctgaaatcgctggttacttcgaccgcgccgctgctgccgtagccCACCATCACC
ATCACCATATCGAAGGGCGATGTGACTTGCCTCAGACGCATTCTTTGGGAAGCCG
ACGCACACTGATGCTGCTCGCCCAAATGCGCCGGATCTCCTTATTCTCCTGTCTCA
AGGATCGGCATGACTTCGGCTTCCCTCAGGAGGAGTTTGGAAATCAGTTCCAAAA
GGCCGAAACCATTCCGGTCCTCCATGAAATGATTCAACAGATCTTTAACTTATTC
AGTACCAAAGACAGCAGTGCGGCCTGGGACGAAACATTACTCGATAAATTCTAC
ACGGAATTATACCAACAGTTGAACGACTTAGAAGCCTGTGTAATCCAAGGTGTTG
GTGTCACTGAGACTCCATTAATGAAAGAAGACTCTATTCTGGCCGTCCGCAAGTA
TTTCCAGCGAATCACACTGTATTTGAAAGAGAAAAAGTATTCTCCGTGTGCGTGG
GAGGTAGTACGGGCTGAAATCATGCGGTCCTTCTCTTTAAGCACAAACCTCCAGG
AATCTCTGCGCTCCAAAGAATGAAGATCTgcggccgcgttgatcggcacgtaagaggttccaactttcacc
ataatgaaataagatcactaccgggcgtatttttgagttatcgagattttcaggagctaaggaagctaaaatggagaaaaaaatcact
ggatataccaccgttgatatatcccaatggcatcgtaaagaacattttgaggcatttcagtcagttgctcaatgtacctataacc
agaccgttcagctggatattacggcctttttaaagaccgtaaagaaaaataagcacaagttttatccggcctttattcacattctt
gcccgcctgatgaatgctcatccggaattccgtatggcaatgaaagacggtgagctggtgatatgggatagtgttcacccttgt
tacaccgttttccatgagcaaactgaaacgttttcatcgctctggagtgaataccacgacgatttccggcagtttctacacatata
ttcgcaagatgtggcgtgttacggtgaaaacctggcctatttccctaaagggtttattgagaatatgtttttcgtctcagccaatc
cctgggtgagtttcaccagttttgatttaaacgtggccaatatggacaacttcttcgcccccgttttcaccatgggcaaatattat
acgcaaggcgacaaggtgctgatgccgctggcgattcaggttcatcatgccgtctgtgatggcttccatgtcggcagaatgctt
aatgaattacaacagtactgcgatgagtggcagggcggggcgtaatttttttaaggcagttattggtgcccttaaacgcctgg*GG*
*ATCCtctggttattttaaaaaccaactttactcaggttccatacccgagaaaatccagcttaaagctgacatatctaggaaaatttt*
*cacattctaacgggagataccagaaca*atgaaaacccctttaactgaagccgtttccaccgctgactctcaaggtcgctttctga
gcagcaccgaattgcaaattgctttcggtcgtctacgtcaagctaatgctggtttgcaagccgctaaagctctgaccgacaatg
cccagagcttggtaaatggtgctgcccaagccgtttataacaaattcccctacaccacccaaacccaaggcaacaactttgctg
cggatcaacggggtaaagacaagtgtgcccgggacatcggctactacctccgcatcgttacctactgcttagttgctggtggta
ccggtcctttggatgagtacttgatcgccggtattgatgaaatcaaccgcacctttgacctctcccccagctggtatgttCTCG
AG 6. *cpc-US . . . nptI*IFN . . . cpcA + cpc genes-DS* construct (see. FIG. 13):
UPPER CASE - upstream *cpc* operon FLANKING SITE (506 nt)
*nptI**($His_{6x}$*Xa)**IFN* (acts also as the resistance cassette) (1,341 nt)
lower case underlined - Transcription terminator
UPPER CASE - *cpcB-cpcA* intergenic sequence
UPPER CASE - ***cpcA* gene** FLANKING SITE (517 nt including UPPER CASE intergenic sequence)
CTCGAG - XhoI restriction site
AGATCT - BglII restriction site
GGATCC - BamHI restriction site
**SEQ ID NO: 10 *cpc-US...nptI*IFN...cpcA+cpc genes-DS* (2420 nt) nucleic acid sequence**

CTCGAGGGAAAGTAGGCTGTGGTTCCCTAGGCAACAGTCTTCCCTACCCCACTGG
AAACTAAAAAAACGAGAAAAGTTCGCACCGAACATCAATTGCATAATTTTAGCC
CTAAAACATAAGCTGAACGAAACTGGTTGTCTTCCCTTCCCAATCCAGGACAATC
TGAGAATCCCCTGCAACATTACTTAACAAAAAAGCAGGAATAAAATTAACAAGA
TGTAACAGACATAAGTCCCATCACCGTTGTATAAAGTTAACTGTGGGATTGCAAA
AGCATTCAAGCCTAGGCGCTGAGCTGTTTGAGCATCCCGGTGGCCCTTGTCGCTG
CCTCCGTGTTTCTCCCTGGATTTATTTAGGTAATATCTCTCATAAATCCCCGGGTA
GTTAACGAAAGTTAATGGAGATCAGTAACAATAACTCTAGGGTCATTACTTTGGA
CTCCCTCAGTTTATCCGGGGGAATTGTGTTTAAGAAAATCCCAACTCATAAAGTC
AAGTAGGAGATTAATTCA*atgagtcacatccagagagaaactagttgttcccgacctcgtttgaatagcaatatgg*
*atgcagatctgtacggatataaatgggcgcgagataacgtaggccaatctggggccactatttatcggttatatggcaaaccagat*
*gctcccgaactgtttctcaaacatggcaaagggtctgtggccaatgatgttaccgatgaaatggtgcggttgaactggttgacaga*
*atttatgcccctcccgaccatcaaacattttatcaggactccagacgatgcatggctattaactacggccattcctgggaaaactgcc*
*tttcaggtgttggaagaatatcccgattctggtgagaatatcgtcgatgcgttagcggtttttctaagacgtctacatagcattcccgttt*
*gcaattgtccctttaattcggaccgggtgttccgcttggcgcaggctcagtcccggatgaataacggtttggtagatgcctcggacttt*
*gatgatgaacggaacggctggcccgttgaacaggtttggaaagagatgcataagctgctgcccttctcccccgacagcgttgttac*
*tcatggagatttttctctcgataatctgattttcgacgaaggcaagctaattggctgtatcgatgtgggacgggtagggattgcggac*
*cggtatcaagacctagcaattttgtggaactgcctaggtgaatttcccccagcctacaaaaacggctgtttcaaaaatacggaatc*
*gataatcccgacatgaacaaattacaatttcatctgatgctagatgagttctttcaccatcaccatcaccat*atcgaagggcgatgtg
acttgcctcagacgcattctttgggaagccgacgcacactgatgctgctcgcccaaatgcgccggatctccttattctcctgtctc
aaggatcggcatgacttcggcttccctcaggaggagtttggaaatcagttccaaaaggccgaaaccattccggtcctccatga
aatgattcaacagatctttaacttattcagtaccaaagacagcagtgcggcctgggacgaaacattactcgataaattctacac
ggaattataccaacagttgaacgacttagaagcctgtgtaatccaaggtgttggtgtcactgagactccattaatgaaagaag
actctattctggccgtccgcaagtatttccagcgaatcacactgtatttgaaagagaaaaagtattctccgtgtgcgtgggaggt
agtacgggctgaaatcatgcggtccttctctttaagcacaaacctccaggaatctctgcgctccaaagaatgatttttttaaggca
gttattggtgcccttaaacgcctgggGATCCTCTGGTTATTTTAAAAACCAACTTTACTCAGGTTC
CATACCCGAGAAAATCCAGCTTAAAGCTGACATATCTAGGAAAATTTTCACATTC
TAACGGGAGATACCAGAACAATGAAAACCCCTTTAACTGAAGCCGTTTCCACC
GCTGACTCTCAAGGTCGCTTTCTGAGCAGCACCGAATTGCAAATTGCTTTCG
GTCGTCTACGTCAAGCTAATGCTGGTTTGCAAGCCGCTAAAGCTCTGACCGA
CAATGCCCAGAGCTTGGTAAATGGTGCTGCCCAAGCCGTTTATAACAAATTC

-continued

CCCTACACCACCCAAACCCAAGGCAACAACTTTGCTGCGGATCAACGGGGT
AAAGACAAGTGTGCCCGGGACATCGGCTACTACCTCCGCATCGTTACCTACT
GCTTAGTTGCTGGTGGTACCGGTCCTTTGGATGAGTACTTGATCGCCGGTAT
TGATGAAATCAACCGCACCTTTGACCTCTCCCCCAGCTGGTATGTTGAAGCT
CTGAAATACATCTCGAG

7. *glgA1-US . . . $P_{TRC}$-nptI*IFN . . . glgA1-DS* construct: (see, FIG. 19, panel A)
UPSTREAM *glgA1* FLANKING SITE (540 nt)
UPPER CASE lower case combination $P_{TRC}$ (101 nt)
*nptI*(HiS6x*Xa)*IFN* (acts also as the resistance cassette) (1,341 nt)
**UPPER CASE T*psbA2* (terminator *psbA2*)** (193)
DOWNSTREAM *glgA1* FLANKING SITE (512)
CTCGAG - XhoI restriction site
GGATCC - BamHI restriction site
**SEQ ID NO: 11 *glgA1-US...PTRC-nptI*IFN...glgA1-DS* (2705 nt) nucleic acid sequence**
CTCGAGGCCATGTCCCAAATTCTTGATCCCATCCCCAACAACCAGCCATCAGCCT
TATTCTGTTGCTACGTCAATGCCACCAATCAAATCCAAGTGGCCCGCATTACCAA
TGTCCCTAATTGGTATTTTGAAAGAGTTGTGTTCCCTGGTCAACGGTTAGTATTTG
AGGCAGTGCCCAGCGCTCAGTTAGAAATTCATACTGGCATGATGGCCAGCTCGAT
TATTTCGGACACCATTCCCTGCGAACAACTGAGTATTGATCCCGACGGATTAGCA
GCGGGCGGTTTCATCTCTCCAGAAAAAGAACACGAGTCCGAGGATATGACTTCC
CAATCCTTAGTGGCTTAGCAATGAATTAATGAATTGGAATACTTAGGCCATGCCA
CCGGCCGGCAATGGATAGTCCACGGACAAAGCACTAAGAAAAAGGTATAGGGAT
GGAAAGCAGAAACTGTTAATTACTCTCTCCGATGGGTAACCACCACCGTCATATA
ATTGAGCGGAAAGTATGGCAACCAGGCCCTGAACTCAATTAGTGGAATAACGCG
GTCCTGCAGGATTCTGAAATGAGCTGTTGACAATTAATCATCCGGCTCGTAT
AAtgtgtggaAATTGTGAGCGGATAACAATTAGGAGGTTAATTAACA*atgagtcacatcc*
*agagagaaactagttgttcccgacctcgtttgaatagcaatatggatgcagatctgtacggatataaatgggcgcgagataacgta*
*ggccaatctggggccactatttatcggttatatggcaaaccagatgctcccgaactgtttctcaaacatggcaaagggtctgtggcc*
*aatgatgttaccgatgaaatggtgcggttgaactggttgacagaatttatgcccctcccgaccatcaaacattttatcaggactccag*
*acgatgcatggctattaactacggccattcctgggaaaactgcctttcaggtgttggaagaatatcccgattctggtgagaatatcgt*
*cgatgcgttagcggtttttctaagacgtctacatagcattcccgtttgcaattgtccctttaattcggaccgggtgttccgcttggcgcag*
*gctcagtcccggatgaataacggtttggtagatgcctcggactttgatgatgaacggaacggctggcccgttgaacaggtttggaa*
*agagatgcataagctgctgcccttctcccccgacagcgttgttactcatggagatttttctctcgataatctgattttcgacgaaggca*
*agctaattggctgtatcgatgtgggacgggtagggattgcggaccggtatcaagacctagcaattttgtggaactgcctaggtgaat*
*tttcccccagcctacaaaaacggctgtttcaaaaatacggaatcgataatcccgacatgaacaaattacaatttcatctgatgctag*
*atgagttctttcaccatcaccatcaccatatcgaagggcgatgtgacttgcctcagacgcattctttgggaagccgacgcacactgat*
*gctgctcgcccaaatgcgccggatctccttattctcctgtctcaaggatcggcatgacttcggcttccctcaggaggagtttggaaat*
*cagttccaaaaggccgaaaccattccggtcctccatgaaatgattcaacagatctttaacttattcagtaccaaagacagcagtgc*
*ggcctgggacgaaacattactcgataaattctacacggaattataccaacagttgaacgacttagaagcctgtgtaatccaaggtg*
*ttggtgtcactgagactccattaatgaaagaagactctattctggccgtccgcaagtatttccagcgaatcacactgtatttgaaaga*
*gaaaaagtattctccgtgtgcgtgggaggtagtacgggctgaaatcatgcggtccttctctttaagcacaaacctccaggaatctct*
*gcgctccaaagaaga*GGATCCTCCTTGGTGTAATGCCAACTGAATAATCTGCAAATT
GCACTCTCCTTCAATGGGGGGTGCTTTTTGCTTGACTGAGTAATCTTCTGAT
TGCTGATCTTGATTGCCATCGATCGCCGGGGAGTCCGGGGCAGTTACCATT
AGAGAGTCTAGAGAATTAATCCATCTTCGATAGAGGAATTATGGGGGAAGA
ACCCTAGGCAATTGATGGCCATGCGTTATGGCTGTATCCCCATTGTGCGGCGGAC
AGGGGGTTTGGTGGATACGGTATCCTTCTACGATCCTATCAATGAAGCCGGCACC
GGCTATTGCTTTGACCGTTATGAACCCCTGGATTGCTTTACGGCCATGGTGCGGG
CCTGGGAGGGTTTCCGTTTCAAGGCAGATTGGCAAAAATTACAGCAACGGGCCA
TGCGGGCAGACTTTAGTTGGTACCGTTCCGCCGGGGAATATATCAAAGTTTATAA
GGGCGTGGTGGGGAAACCGGAGGAATTAAGCCCCATGGAAGAGGAAAAAATCG
CTGAGTTAACTGCTTCCTATCGCTAACAATCTCCCGGCAGTGAAGTAAAATCCTG
AACCCTAATCCCGCTCCACTGCCGACCCCAATTCTCCTTGCCTAGGCAAATTTGA
AAATTTTTTCTGATCAATGCTTGTGGTGAAGCAAAAGCTATGTTAACGTTATAAA
TCGTGCCAATGAAGCACAACGGGCTCGAG 8. cpc us . . . cpcB*HisTag*Xa*optK2S-cmR . . . cpcA construct (see. FIG. 15)
5' RECOMBINATION
CTCGAG - XhoI DNA restriction site
Lower case - CpcB
UPPER CASE - Histag 6x
UPPER CASE - Factor Xa cleavage site (IEGR)
UPPER CASE - *Synechtxystis*-optimized K2S (without first methionine, plus stop codon)
AGATCT - BglII DNA restriction site
*GGATCC* - BamHI DNA restriction site
lower case - intergenic sequence in Cinzia's construct
Lower case bold - cmR
lower case underlined - Transcription terminator
*GGATCC* - BamHI DNA restriction site
*lower case italics* - CpcB-CpcA intergenic sequence
lower case bold - CpcA (partial)
CTCGAG - XhoI DNA restriction site
3' RECOMBINATION
SEQ ID NO: 12 *cpc us . . . cpcB*HisTag*Xa*optK2S-cmR . . . cpcA* (2949 nt) nucleic acid sequence
CTCGAGatgttcgacgtattcactcgggttgtttcccaagctgatgctcgcggcgagtacctctctggttctcagttagatgctttgag
cgctaccgttgctgaaggcaacaaacggattgattctgttaaccgcatcaccggtaatgcttccgctatcgtttccaacgctgctcgtgct
ttgttcgccgaacagccccaattaatccaacccggtggaaacgcctacaccagccgtcgtatggctgcttgtttgcgtgacatggaaat
catcctccgctatgttacctacgcaaccttcaccggcgacgcttccgttctagaagatcgttgcttgaacggtctccgtgaaacctacgtt -continued gccctgggtgttcccggtgcttccgtagctgctggcgttcaaaaaatgaaagaagctgccctggacatcgttaacgatcccaatggcat
cacccgtggtgattgcagtgctatcgttgctgaaatcgctggttacttcgaccgcgccgctgctgccgtagccCACCATCACC
ATCACCATATCGAAGGGCGATCCTATCAAGGCAATTCCGATTGTTATTTTGGCAA
TGGCTCCGCCTATCGGGGCACCCATTCCTTGACCGAATCCGGCGCCTCCTGTTTG
CCCTGGAATTCCATGATTTTGATTGGCAAAGTGTATACCGCCCAAAATCCCTCCG
CCCAAGCCTTGGGCTTGGGCAAACATAATTATTGTCGGAATCCCGATGGCGATGC
CAAACCCTGGTGTCATGTGTTGAAGAATCGGCGGTTGACCTGGGAATATTGTGAT
GTGCCCTCCTGTTCCACCTGTGGCTTGCGGCAATATTCCCAACCCCAATTTCGGAT
TAAAGGCGGCTTGTTTGCCGATATTGCCTCCCATCCCTOGCAAGCCGCCATCTTT
GCCAAACATCGGCGGTCTCCCGGCGAACGGTTCTTGTGTGGCGGCATTTTGATTT
CCTCCTGTTGGATTTTGTCCGCCGCCCATTGTTTTCAAGAACGGTTTCCTCCCCAT
CATTTGACCGTGATTTTGGGCCGGACCTATCGGGTGGTGCCCGGCGAAGAAGAA
CAGAAATTTGAAGTGGAGAAATATATTGTGCATAAAGAATTTGATGATGATACCT
ATGATAATGATATTGCCTTGTTGCAATTGAAATCCGATTCCTCCCGGTGTGCCCA
AGAATCCTCCGTGGTGCGGACCGTGTGTTTGCCTCCCGCCGATTTGCAATTGCCC
GATTGGACCGAATGTGAATTGTCCGGCTATGGCAAACATGAAGCCTTGTCTCCCT
TTTATTCCGAACGGTTGAAAGAAGCCCATGTGCGGTTGTATCCCTCCTCCCGGTG
TACCTCCCAACATTTGTTGAATCGGACCGTGACCGATAATATGTTGTGTGCCGGC
GATACCCGGTCCGGCGGCCCCCAAGCCAATTTGCATGATGCCTGTCAAGGCGATT
CCGGCGGCCCCTTGGTGTGTTTGAATGATGGCCGGATGACCTTGGTGGGCATTAT
TTCCTGGGGCTTGGGCTGTGGCCAGAAAGATGTGCCCGGCGTGTATACCAAAGTG
ACCAATTATTTGGATTGGATTCGGGATAATATGCGGCCCTAAAGATCTgcggccgcgtt
gatcggcacgtaagaggttccaactttcaccataatgaaataagatcactaccgggcgtattttttgagttatcgagattttcaggagctaa
ggaagctaaaatggagaaaaaaatcactggatataccaccgttgatatatcccaatggcatcgtaaagaacattttgaggcatt
tcagtcagttgctcaatgtacctataaccagaccgttcagctggatattacggcctttttaaagaccgtaaagaaaaataagca
caagttttatccggcctttattcacattcttgcccgcctgatgaatgctcatccggaattccgtatggcaatgaaagacggtgagc
tggtgatatgggatagtgttcacccttgttacaccgttttccatgagcaaactgaaacgttttcatcgctctggagtgaataccac
gacgatttccggcagtttctacacatatattcgcaagatgtggcgtgttacggtgaaaacctggcctatttccctaaagggtttat
tgagaatatgtttttcgtctcagccaatccctgggtgagtttcaccagttttgatttaaacgtggccaatatggacaacttcttcgc
ccccgttttcaccatgggcaaatattatacgcaaggcgacaaggtgctgatgccgctggcgattcaggttcatcatgccgtctgt
gatggcttccatgtcggcagaatgcttaatgaattacaacagtactgcgatgagtggcagggcggggcgtaatttttttaaggca
gttattggtgcccttaaacgcctgg*GGATCCtctggttattttaaaaaccaactttactcaggttccatacccgagaaaatccagct*
*taaagctgacatatctaggaaaattttcacattctaacgggagataccagaaca*atgaaaacccctttaactgaagccgtttcca
ccgctgactctcaaggtcgctttctgagcagcaccgaattgcaaattgctttcggtcgtctacgtcaagctaatgctggtttgcaa
gccgctaaagctctgaccgacaatgcccagagcttggtaaatggtgctgcccaagccgtttataacaaattcccctacaccacc
caaacccaaggcaacaactttgctgcggatcaacggggtaaagacaagtgtgcccgggacatcggctactacctccgcatcg
ttacctactgcttagttgctggtggtaccggtcctttggatgagtacttgatcgccggtattgatgaaatcaaccgcacctttgac
ctctcccccagctggtatgttCTCGAG 9. *cpc-US . . . nptI*HisTag*Xa*K2S . . . cpcA + cpc genes-DS* construct: (see, FIG. 19, panel B)
UPPER CASE - upstream *cpc* operon FLANKING SITE (506 nt)
*nptI**($His_{6x}$*Xa)**K2S* (acts also as the resistance cassette) (2,478 nt)
lower case underlined - Transcription terminator
UPPER CASE - *cpcB-cpcA* intergenic sequence **plus *cpcA* gene** FLANKING SITE (517 nt)
CTCGAG - XhoI restriction site
AGATCT - BglII restriction site
GGATCC - BamHI restriction site

**SEQ ID NO: 13 *cpc-US...nptI*HisTag*Xa*K2S...cpcA+cpc genes-DS* (2990 nt) nucleic acid sequence**

CTCGAGGGAAAGTAGGCTGTGGTTCCCTAGGCAACAGTCTTCCCTACCCCACTGG
AAACTAAAAAAACGAGAAAAGTTCGCACCGAACATCAATTGCATAATTTTAGCC
CTAAAACATAAGCTGAACGAAACTGGTTGTCTTCCCTTCCCAATCCAGGACAATC
TGAGAATCCCCTGCAACATTACTTAACAAAAAAGCAGGAATAAAATTAACAAGA
TGTAACAGACATAAGTCCCATCACCGTTGTATAAAGTTAACTGTGGGATTGCAAA
AGCATTCAAGCCTAGGCGCTGAGCTGTTTGAGCATCCCGGTGGCCCTTGTCGCTG
CCTCCGTGTTTCTCCCTGGATTTATTTAGGTAATATCTCTCATAAATCCCCGGGTA
GTTAACGAAAGTTAATGGAGATCAGTAACAATAACTCTAGGGTCATTACTTTGGA
CTCCCTCAGTTTATCCGGGGGAATTGTGTTTAAGAAAATCCCAACTCATAAAGTC
AAGTAGGAGXTTAATTCA*atgagtcacatccagagagaaactagttgttcccgacctcgtttgaatagcaatatgg*
*atgcagatctgtacggatataaatgggcgcgagataacgtaggccaatctggggccactatttatcggttatatggcaaaccagat*
*gctcccgaactgtttctcaaacatggcaaagggtctgtggccaatgatgttaccgatgaaatggtgcggttgaactggttgacaga*
*atttatgcccctcccgaccatcaaacattttatcaggactccagacgatgcatggctattaactacggccattcctgggaaaactgcc*
*tttcaggtgttggaagaatatcccgattctggtgagaatatcgtcgatgcgttagcggtttttctaagacgtctacatagcattcccgttt*
*gcaattgtccctttaattcggaccgggtgttccgcttggcgcaggctcagtcccggatgaataacggtttggtagatgcctcggacttt*
*gatgatgaacggaacggctggcccgttgaacaggtttggaaagagatgcataagctgctgcccttctcccccgacagcgttgttac*
*tcatggagatttttctctcgataatctgattttcgacgaaggcaagctaattggctgtatcgatgtgggacgggtagggattgcggac*
*cggtatcaagacctagcaattttgtggaactgcctaggtgaatttcccccagcctacaaaaacggctgtttcaaaaatacggaatc*
*gataatcccgacatgaacaaattacaatttcatctgatgctagatgagttctttcaccatcaccatcaccat*atcgaagggcga*TCC*
*TATCAAGGCAATTCCGATTGTTATTTTGGCAATGGCTCCGCCTATCGGGGCACCCATTCCTTGACCGAATC*
*CGGCGCCTCCTGTTTGCCCTGGAATTCCATGATTTTGATTGGCAAAGTGTATACCGCCCAAAATCCCTCC*
*GCCCAAGCCTTGGGCTTGGGCAAACATAATTATTGTCGGAATCCCGATGGCGATGCCAAACCCTGGTGTC*
*ATGTGTTGAAGAATCGGCGGTTGACCTGGGAATATTGTGATGTGCCCTCCTGTTCCACCTGTGGCTTGCG*
*GCAATATTCCCAAGCCCAATTTCGGATTAAAGGCGGCTTGTTTGCCGATATTGCCTCCCATCCCTGGCAAG*
*CCGCCATCTTTGCCAAACATCGGCGGTCTCCCGGCGAACGGTTCTTGTGTGGCGGCATTTTGATTTCCTC*
*CTGTTGGATTTTGTCCGCCGCCCATTGTTTTCAAGAACGGTTTCCTCCCCATCATTTGACCGTGATTTTGG*
*GCCGGACCTATCGGGTGGTGCCCGGCGAAGAAGAACAGAAATTTGAAGTGGAGAAATATATTGTGCATAA*
*AGAATTTGATGATGATACCTATGATAATGATATTGCCTTGTTGCAATTGAAATCCGATTCCTCCCGGTGTGC*
*CCAAGAATCCTCCGTGGTGCGGACCGTGTGTTTGCCTCCCGCCGATTTGCAATTGCCCGATTGGACCGA*
*ATGTGAATTGTCCGGCTATGGCAAACATGAAGCCTTGTCTCCCTTTTATTCCGAACGGTTGAAAGAAGCCC*
*ATGTGCGGTTGTATCCCTCCTCCCGGTGTACCTCCCAACATTTGTTGAATCGGACCGTGACCGATAATATG*

-continued

*TTGTGTGCCGGCGATACCCGGTCCGGCGGCCCCCAAGCCAATTTGCATGATGCCTGTCAAGGCGATTCC*
*GGCGGCCCCTTGGTGTGTTTGAATGATGGCCGGATGACCTTGGTGGGCATTATTTCCTGGGGCTTGGGC*
*TGTGGCCAGAAAGATGTGCCCGGCGTGTATACCAAAGTGACCAATTATTTGGATTGGATTCGGGATAATAT*
*GCGGCCCTAA*tttttttaaggcagttattcgtgcccttaaacgcctgggGATCCTCTGGTTATTTTAAAAACC
AACTTTACTCAGGTTCCATACCCGAGAAAATCCAGCTTAAAGCTGACATATCTAG
GAAAATTTTCACATTCTAACGGGAGATACCAGAACAATGAAAACCCCTTTAACT
GAAGCCGTTTCCACCGCTGACTCTCAAGGTCGCTTTCTGAGCAGCACCGAAT
TGCAAATTGCTTTCGGTCGTCTACGTCAAGCTAATGCTGGTTTGCAAGCCGC
TAAAGCTCTGACCGACAATGCCCAGAGCTTGGTAAATGGTGCTGCCCAAGC
CGTTTATAACAAATTCCCCTACACCACCCAAACCCAAGGCAACAACTTTGCT
GCGGATCAACGGGGTAAAGACAAGTGTGCCCGGGACATCGGCTACTACCTC
CGCATCGTTACCTACTGCTTAGTTGCTGGTGGTACCGGTCCTTTGGATGAGT
ACTTGATCGCCGGTATTGATGAAATCAACCGCACCTTTGACCTCTCCCCCAG
CTGGTATGTTGAAGCTCTGAAATACATCTCGAG 10. *cpc us . . . cpcB*INS - cmR + cpc genes . . . cpc ds* construct (see, FIG. 16):
CTCGAG - XhoI DNA restriction site
AGATCT - BglII DNA restriction site
*GGATCC* - BamHI DNA restriction site
Lower case - cpcB
5' RECOMBINATION
UPPER CASE - Factor Xa cleavage site (IEGR)
lower case - Human proinsulin, codon-optimized for expression in *Synechocystis* PCC.6803
lower case - intergenic sequence in Cinzia's construct
lower case - cmR
lower case underlined - Transcription terminator
3' RECOMBINATION
*lower case italics* - *cpcB-cpcA* intergenic sequence
lower case bold - *cpcA* (partial)
**SEQ ID NO: 14 *cpc us ... cpcB*INS-cmR + cpc genes ... cpc ds* (2112 nt) nucleic acid sequence**
atgttcgacgtattcactcgggttgtttcccaagctgatgctcgcggcgagtacctctctggttctcagttagatgctttgagcgctaccgtt
gctgaaggcaacaaacggattgattctgttaaccgcatcaccggtaatgcttccgctatcgtttccaacgctgctcgtgctttgttcgccg
aacagccccaattaatccaacccggtggaaacgcctacaccagccgtcgtatggctgcttgtttgcgtgacatggaaatcatcctccgc
tatgttacctacgcaaccttcaccggcgacgcttccgttctagaagatcgttgcttgaacggtctccgtgaaacctacgttgccctgggtg
ttcccggtgcttccgtagctgctggcgttcaaaaaatgaaagaagctgccctggacatcgttaacgatcccaatggcatcacccgtggt
gattgcagtgctatcgttgctgaaatcgctggttacttcgaccgcgccgctgctgccgtagccATCGAAGGGCGAttcgtga
accagcacttgtgcggtagtcacttagtcgaagcgctctatctagtctgtggtgaacgaggtttcttctatactccctaagactcgacgtga
ggctgaggacctccaagtaggacaggtagaactaggaggcggaccaggagccgggtctttgcagccgttggcactagaagggagc
ctccagaagcgagggatcgtggagcagtgctgcacatccatctgtagcttataccaattagagaattactgcaattagAGATCTgc
ggccgcgttgatcggcacgtaagaggttccaactttcaccataatgaaataagatcactaccgggcgtatttttttgagttatcgagatttc
aggagctaaggaagctaaaatggagaaaaaaatcactggatataccaccgttgatatatcccaatggcatcgtaaagaacattt
tgaggcatttcagtcagttgctcaatgtacctataaccagaccgttcagctggatattacggcctttttaaagaccgtaaagaaa
aataagcacaagttttatccggcctttattcacattcttgcccgcctgatgaatgctcatccggaattccgtatggcaatgaaag
acggtgagctggtgatatgggatagtgttcacccttgttacaccgttttccatgagcaaactgaaacgttttcatcgctctggagt
gaataccacgacgatttccggcagtttctacacatatattcgcaagatgtggcgtgttacggtgaaaacctggcctatttccct a
aagggtttattgagaatatgtttttcgtctcagccaatccctgggtgagtttcaccagttttgatttaaacgtggccaatatggac
aacttcttcgcccccgttttcaccatgggcaaatattatacgcaaggcgacaaggtgctgatgccgctggcgattcaggttcatc
atgccgtctgtgatggcttccatgtcggcagaatgcttaatgaattacaacagtactgcgatgagtggcagggcggggcgtaat
tttttaaggcagttattggtgcccttaaacgcctgg*GGATCCtctggttatttaaaaaccaactttactcaggttccatacccgaga*
*aaatccagcttaaagctgacatatctaggaaaattttcacattctaacgggagataccagaaca*atgaaaacccctttaactgaa
gccgtttccaccgctgactctcaaggtcgctttctgagcagcaccgaattgcaaattgctttcggtcgtctacgtcaagctaatgc
tggtttgcaagccgctaaagctctgaccgacaatgcccagagcttggtaaatggtgctgcccaagccgtttataacaaattccc
ctacaccacccaaacccaaggcaacaactttgctgcggatcaacggggtaaagacaagtgtgcccgggacatcggctactac
ctccgcatcgttacctactgcttagttgctggtggtaccggtcctttggatgagtacttgatcgccggtattgatgaaatcaaccg
cacctttgacctctcccccagctggtatgtt

11. *cpcB*L7*His*TTFC-smR + cpc* (3243 nt) (see FIG. 17, panel A)
TTFC: Tetanus Toxin Fragment C
UPPER CASE, *cpcB* gene + L7 linker (underlined) for homologous recombination (537 nt)
Lower case <caccatcaccatcaccatgataatttgtatttacaaggc>: His-tag + TEV cleavage site (39 nt)
UPPER CASE BOLD, Tetanus Toxin Fragment C (TTFC) + STOP CODON (1356 nt)
Lower case bold RBS (18 nt)
*UPPER CASE ITALICS, smR* gene for antibiotic selection (792 nt)
*Lower case italics*, transcription terminator + intergenic seq + partial *cpcA* gene for homologous recombination (501 nt)
ATGTTCGACGTATTCACTCGGGTTGTTTCCCAAGCTGATGCTCGCGGCGAGTACCTCTCTG
GTTCTCAGTTAGATGCTTTGAGCGCTACCGTTGCTGAAGGCAACAAACGGATTGATTCTG
TTAACCGCATCACCGGTAATGCTTCCGCTATCGTTTCCAACGCTGCTCGTGCTTTGTTCGC
CGAACAGCCCCAATTAATCCAACCCGGTGGAAACGCCTACACCAGCCGTCGTATGGCTG
CTTGTTTGCGTGACATGGAAATCATCCTCCGCTATGTTACCTACGCAACCTTCACCGGCG
ACGCTTCCGTTCTAGAAGATCGTTGCTTGAACGGTCTCCGTGAAACCTACGTTGCCCTGG
GTGTTCCCGGTGCTTCCGTAGCTGCTGGCGTTCAAAAAATGAAAGAAGCTGCCCTGGACA
TCGTTAACGATCCCAATGGCATCACCCGTGGTGATTGCAGTGCTATCGTTGCTGAAATCG
CTGGTTACTTCGACCGCGCCGCTGCTGCCGTAGCCCCCATGCCTTGGCGCGTGATTcaccatc
accatcaccatgataatttgtatttacaaggcAAGAACTTAGACTGTTGGGTCGATAATGAGGAGGATAT
CGATGTCATTCTAAAGAAGTCTACCATCCTAAATCTGGACATTAACAATGATATCAT
TAGTGATATTTCTGGTTTTAATTCTTCTGTTATCACATACCCCGACGCCCAATTAGTT
CCAGGAATTAATGGGAAGGCTATTCATCTAGTAAATAATGAGAGCAGCGAAGTGAT
CGTCCACAAGGCGATGGACATTGAGTATAATGATATGTTCAACAACTTTACTGTGTC

-continued

CTTTTGGTTGCGCGTCCCCAAAGTGTCTGCCAGTCACCTGGAACAATACGACACGA
ATGAATATAGTATCATTAGCAGTATGAAAAAGTATAGTTTAAGTATTGGGTCTGGGT
GGTCCGTCTCTCTCAAAGGAAACAACCTCATCTGGACCCTCAAGGATTCTGCAGGC
GAAGTGCGTCAAATTACATTCCGCGACTTGTCCGATAAATTCAATGCGTACCTCGCT
AACAAATGGGTTTTCATCACCATCACGAACGACCGGCTGAGTAGCGCTAACCTCTA
CATTAATGGCGTGTTGATGGGGAGTGCGGAGATCACCGGCCTGGGGGCAATTCGC
GAGGACAACAACATCACACTCAAGTTGGACCGTTGCAATAACAACAACCAATATGT
CTCTATCGACAAATTTCGTATTTTCTGTAAGGCGCTAAACCCAAAGGAGATCGAAAA
GTTATATACTAGTTATTTGAGCATCACGTTTTTACGCGATTTTTGGGGCAACCCACT
GCGTTATGACACTGAATATTATCTCATTCCCGTTGCGTACAGCAGTAAAGACGTCCA
ATTAAAGAATATCACGGATTATATGTATCTGACTAATGCTCCCAGTTACACGAACGG
GAAATTAAACATTTACTACCGCCGTCTGTACTCTGGTCTGAAGTTTATTATCAAACG
CTACACCCCCAACAATGAAATCGACTCTTTTGTTCGGTCTGGTGACTTTATTAAACT
GTACGTAAGTTACAACAACAATGAACACATCGTGGGATACCCTAAAGACGGGAATG
CGTTCAATAACTTAGATCGGATCCTCCGAGTAGGGTATAATGCACCCGGTATTCCTC
TGTATAAGAAGATGGAAGCGGTAAAGCTCCGTGACCTCAAAACTTATAGCGTGCAA
CTCAAACTGTACGACGACAAAGATGCGTCTCTAGGGTTGGTGGGTACCCACAACGG
ACAAATCGGGAATGACCCTAACCGCGATATTCTAATCGCTTCTAATTGGTATTTTAA
CCACTTAAAAGATAAGACCCTCACCTGCGACTGGTATTTCGTCCCAACCGACGAGG
GATGGACTAATGATTGAggaattaggaggtaatatATGAGGGAAGCGGTGATCGCCGAAGTATCGA
CTCAACTATCAGAGGTAGTTGGCGTCATCGAGCGCCATCTCGAACCGACGTTGCTGGCCGTAC
ATTTGTACGGCTCCGCAGTGGATGGCGGCCTGAAGCCACACAGTGATATTGATTTGCTGGTTAC
GGTGACCGTAAGGCTTGATGAAACAACGCGGCGAGCTTTGATCAACGACCTTTTGGAAACTTC
GGCTTCCCCTGGAGAGAGCGAGATTCTCCGCGCTGTAGAAGTCACCATTGTTGTGCACGACGA
CATCATTCCGTGGCGTTATCCAGCTAAGCGCGAACTGCAATTTGGAGAATGGCAGCGCAATGA
CATTCTTGCAGGTATCTTCGAGCCAGCCACGATCGACATTGATCTGGCTATCTTGCTGACAAAA
GCAAGAGAACATAGCGTTGCCTrGGTAGGTCCAGCGGCGGAGGAACTCTTTGATCCGGTTCCr
GAACAGGATCTATTTGAGGCGCTAAATGAAACCTTAACGCTATGGAACTCGCCGCCCGACTGG
GCTGGCGATGAGCGAAATGTAGTGCTTACGTTGTCCCGCATTTGGTACAGCGCAGTAACCGGC
AAAATCGCGCCGAAGGATGTCGCTGCCGACTGGGCAATGGAGCGCCTGCCGGCCCAGTATCA
GCCCGTCATACTTGAAGCTAGACAGGCTTATCTTGGACAAGAAGAAGATCGCTTGGCCTCGCG
CGCAGATCAGrrGGAAGAAnTGTCCACTACGTGAAAGGCGAGATCACCAAGGTAGTCGGCAA
ATAAtttttttaaggcagttattggtgcccttaaacgcctgggGATCCtctggttattttaaaaaccaactttactcaggttccatacccgagaa
aatccagcttaaagctgacatatctaggaaaattttcacattctaacgggagataccagaacaatgaaaacccctttaactgaagccgtttcca
ccgctgactctcaaggtcgctttctgagcagcaccgaattgcaaattgctttcggtcgtctacgtcaagctaatgctggtttgcaagccgctaaag
ctctgaccgacaatgcccagagcttggtaaatggtgctgcccaagccgtttataacaaattccctacaccacccaaacccaaggcaacaact
ttgctgcggatcaacggggtaaagacaagtgtgcccgggacatcggctactacctccgcatcgttacctactgcttagttgctggtggtaccggt
cctttggatgagtacttgatcgccggtattga 12. cpcB*L7*His*TEV*$RBD_{S1}$-smR + cpc (2559 nt) (see, FIG. 18, panel A)
$RBD_{S1}$ of S protein from SARS-CoV-2,
website http covid-19.uniprot.org/uniprotkb/P0DTC2
UPPER CASE, cpcB gene + L7 linker (underlined) for homologous recombination (537 nt)
Lower case <caccatcaccatcaccatgataatttgtatttacaaggc>: His-tag + TEV cleavage site (39 nt)
UPPER CASE BOLD, Receptor Binding Domain (RBD) of the S1-protein from SARS-CoV-2 + STOP CODON (672 nt)
Lower case bold RBS (ggaattaggaggtaatat), (18 nt)
*UPPER CASE ITALICS*, smR gene for antibiotic selection (792 nt)
*Lower case italics*, transcription terminator + intergenic seq + partial cpcA gene for homologous recombination (501 nt)

ATGTTCGACGTATTCACTCGGGTTGTTTCCCAAGCTGATGCTCGCGGCGAGTACCTCTCTG
GTTCTCAGTTAGATGCTTTGAGCGCTACCGTTGCTGAAGGCAACAAACGGATTGATTCTG
TTAACCGCATCACCGGTAATGCTTCCGCTATCGTTTCCAACGCTGCTCGTGCTTTGTTCGC
CGAACAGCCCCAATTAATCCAACCCGGTGGAAACGCCTACACCAGCCGTCGTATGGCTG
CTTGTTTGCGTGACATGGAAATCATCCTCCGCTATGTTACCTACGCAACCTTCACCGGCG
ACGCTTCCGTTCTAGAAGATCGTTGCTTGAACGGTCTCCGTGAAACCTACGTTGCCCTGG
GTGTTCCCGGTGCTTCCGTAGCTGCTGGCGTTCAAAAAATGAAAGAAGCTGCCCTGGACA
TCGTTAACGATCCCAATGGCATCACCCGTGGTGATTGCAGTGCTATCGTTGCTGAAATCG
CTGGTTACTTCGACCGCGCCGCTGCTGCCGTAGCCCCCATGCCTTGGCGCGTGATTcaccatc
accatcaccatcataatttgtatttacaaggcCGGGTGCAACCCACCGAATCCATTGTGCGGTTTCCCAAT
ATTACCAATTTGTGTCCCTTTGGCGAAGTGTTTAATGCCACCCGGTTTGCCTCCGTG
TATGCCTGGAATCGGAAACGGATTTCCAATTGTGTGGCCGATTATTCCGTGTTGTAT
AATTCCGCCTCCTTTTCCACCTTTAAATGTTATGGCGTGTCCCCCACCAAATTGAAT
GATTTGTGTTTTACCAATGTGTATGCCGATTCCTTTGTGATTCGGGGCGATGAAGTG
CGGCAAATTGCCCCCGGCCAAACCGGCAAAATTGCCGATTATAATTATAAATTGCC
CGATGATTTTACCGGCTGTGTGATTGCCTGGAATTCCAATAATTTGGATTCCAAAGT
GGGCGGCAATTATAATTATTTGTATCGGTTGTTTCGGAAATCCAATTTGAAACCCTT
TGAACGGGATATTTCCACCGAAATTTATCAAGCCGGCTCCACCCCCTGTAATGGCG
TGGAAGGCTTTAATTGTTATTTTCCCTTGCAATCCTATGGCTTTCAACCCACCAATG
GCGTGGGCTATCAACCCTATCGGGTGGTGGTGTTGTCCTTTGAATTGTTGCATGCC
CCCGCCACCGTGTGTGGCCCCAAAAAATCCACCAATTTGGTGAAAAATAAATGTGT
GAATTTTTGAggaattaggaggtaatatATGAGGGAAGCGGTGATCGCCGAAGTATCGACTCAACTAT
CAGAGGTAGTTGGCGTCATCGAGCGCCATCTCGAACCGACGTTGCTGGCCGTACATTTGTATG
GCTCCGCAGTGGATGGCGGCCTGAAGCCACACAGTGATATTGATTTGCTGGTTACGGTGACCG
TAAGGCTTGATGAAACAACGCGGCGAGCTTTGATCAACGACCTTTTGGAAACTTCGGCTTCCCC
TGGAGAGAGCGAGATTCTCCGCGCTGTAGAAGTCACCATTGTTGTGCACGACGACATCATTCC
GTGGCGTTATCCAGCTAAGCGCGAACTGCAATTTGGAGAATGGCAGCGCAATGACATTCTTGC
AGGTATCTTCGAGCCAGCCACGATCGACATTGATCTGGCTATCTTGCTGACAAAAGCAAGAGAA
CATAGCGTTGCCTTGGTAGGTCCAGCGGCGGAGGAACTCTTTGATCCGGTTCCTGAACAGGAT
CTATTTGAGGCGCTAAATGAAACCTTAACGCTATGGAACTCGCCGCCCGACTGGGCTGGCGAT
GAGCGAAATGTAGTGCTTACGTTGTCCCGCATTTGGTACAGCGCAGTAACCGGCAAAATCGCG -continued

*CCGAAGGATGTCGCTGCCGACTGGGCAATGGAGCGCCTGCCGGCCCAGTATCAGCCCGTCAT*
*ACTTGAAGCTAGACAGGCTTATCTTGGACAAGAAGAAGATCGCCTTGGCCTCGCGCGCAGATCA*
*GTTGGAAGAATTTGTCCACTACGTGAAAGGCGAGATCACCAAGGTAGTCGGCAAATAAtttttttaag*
*gcagttattggtgcccttaaacgcctgggCTATCCtctggttattttaaaaaccaactttactcagttccatacccgagaaaatccagcttaaa*
*gctgacatatctaggaaaattttcacattctaacgggagataccagaacaatgaaaacccctttaactgaagccgtttccaccgctgactctcaa*
*ggtcgctttctgagcagcaccgaattg*
*caaattgctttcggtcgtctacgtcaagctaatgctggtttgcaagccgctaaagctctgaccgacaat*
*gcccagagcttggtaaatggtgctgcccaagccgtttataacaaattcccctacaccacccaaacccaaggcaacaactttgctgcggatcaa*
*cggggtaaagacaagtgtgcccgggacatcggctactacctccgcatcgttacctactgcttagttgctggtggtaccggtcctttggatgagta*
*cttgatcgccggtattga*

13. *cpcB*L7*His*TEV*S1-smR + cpc (3909 nts*) (see, FIG. 19, panel C)
S1 domain of S protein from SARS-CoV-2
website http covid-19.uniprot.org/uniprotkb/P0DTC2
UPPER CASE, *cpcB* gene + L7 linker (underlined) for homologous recombination (537 nt)
Lower case <caccatcaccatcaccatgataatttgtatttacaaggc>: His-tag + TEV cleavage site (39 nt)
UPPER CASE BOLD, S1 domain of spike S-protein from SARS-CoV-2 virus + STOP CODON (2022 nt)
Lower case bold RBS (ggaattaggaggtaatat) (18 nt)
*UPPER CASE ITALICS*, *smR* gene for antibiotic selection (792 nt)
*Lower case italics*, transcription terminator + intergenic seq + partial *cpcA* gene for homologous recombination (501 nt)

ATGTTCGACGTATTCACTCGGGTTGTTTCCCAAGCTGATGCTCGCGGCGAGTACCTCTCTG
GTTCTCAGTTAGATGCTTTGAGCGCTACCGTTGCTGAAGGCAACAAACGGATTGATTCTG
TTAACCGCATCACCGGTAATGCTTCCGCTATCGTTTCCAACGCTGCTCGTGCTTTGTTCGC
CGAACAGCCCCAATTAATCCAACCCGGTGGAAACGCCTACACCAGCCGTCGTATGGCTG
CTTGTTTGCGTGACATGGAAATCATCCTCCGCTATGTTACCTACGCAACCTTCACCGGCG
ACGCTTCCGTTCTAGAAGATCGTTGCTTGAACGGTCTCCGTGAAACCTACGTTGCCCTGG
GTGTTCCCGGTGCTTCCGTAGCTGCTGGCGTTCAAAAAATGAAAGAAGCTGCCCTGGACA
TCGTTAACGATCCCAATGGCATCACCCGTGGTGATTGCAGTGCTATCGTTGCTGAAATCG
CTGGTTACTTCGACCGCGCCGCTGCTGCCGTAGCCCCCATGCCTTGGCGCGTGATTcaccatc
accatcaccatcataatttgtatttacaaggTCCCAATGTGTGAATTTGACCACCCGGACCCAATTGCCC
CCCGCCTATACCAATTCCTTTACCCGGGGCGTGTATTATCCCGATAAAGTGTTTCGG
TCCTCCGTGTTGCATTCCACCCAAGATTTGTTTTTGCCCTTTTTTTCCAATGTGACCT
GGTTTCATGCCATTCATGTGTCCGGCACCAATGGCACCAAACGGTTTGATAATCCC
GTGTTGCCCTTTAATGATGGCGTGTATTTTGCCTCCACCGAAAAATCCAATATTATT
CGGGGCTGGATTTTTGGCACCACCTTGGATTCCAAAACCCAATCCTTGTTGATTGTG
AATAATGCCACCAATGTGGTGATTAAAGTGTGTGAATTTCAATTTTGTAATGATCCC
TTTTTGGGCGTGTATTATCATAAAAATAATAAATCCTGGATGGAATCCGAATTTCGG
GTGTATTCCTCCGCCAATAATTGTACCTTTGAATATGTGTCCCAACCCTTTTTGATG
GATTTGGAAGGCAAACAAGGCAATTTTAAAAATTTGCGGGAATTTGTGTTTAAAAAT
ATTGATGGCTATTTTAAAATTTATTCCAAACATACCCCCATTAATTTGGTGCGGGAT
TTGCCCCAAGGCTTTTCCGCCTTGGAACCCTTGGTGGATTTGCCCATTGGCATTAAT
ATTACCCGGTTTCAAACCTTGTTGGCCTTGCATCGGTCCTATTTGACCCCCGGCGAT
TCCTCCTCCGGCTGGACCGCCGGCGCCGCCGCCTATTATGTGGGCTATTTGCAACC
CCGGACCTTTTTGTTGAAATATAATGAAAATGGCACCATTACCGATGCCGTGGATTG
TGCCTTGGATCCCTTGTCCGAAACCAAATGTACCTTGAAATCCTTTACCGTGGAAAA
AGGCATTTATCAAACCTCCAATTTTCGGGTGCAACCCACCGAATCCATTGTGCGGTT
TCCCAATATTACCAATTTGTGTCCCTTTGGCGAAGTGTTTAATGCCACCCGGTTTGC
CTCCGTGTATGCCTGGAATCGGAAACGGATTTCCAATTGTGTGGCCGATTATTCCGT
GTTGTATAATTCCGCCTCCTTTTCCACCTTTAAATGTTATGGCGTGTCCCCCACCAA
ATTGAATGATTTGTGTTTTACCAATGTGTATGCCGATTCCTTTGTGATTCGGGGCGA
TGAAGTGCGGCAAATTGCCCCCGGCCAAACCGGCAAAATTGCCGATTATAATTATA
AATTGCCCGATGATTTTACCGGCTGTGTGATTGCCTGGAATTCCAATAATTTGGATT
CCAAAGTGGGCGGCAATTATAATTATTTGTATCGGTTGTTTCGGAAATCCAATTTGA
AACCCTTTGAACGGGATATTTCCACCGAAATTTATCAAGCCGGCTCCACCCCCTGTA
ATGGCGTGGAAGGCTTTAATTGTTATTTTCCCTTGCAATCCTATGGCTTTCAACCCA
CCAATGGCGTGGGCTATCAACCCTATCGGGTGGTGGTGTTGTCCTTTGAATTGTTG
CATGCCCCCGCCACCGTGTGTGGCCCCAAAAAATCCACCAATTTGGTGAAAAATAA
ATGTGTGAATTTTAATTTTAATGGCTTGACCGGCACCGGCGTGTTGACCGAATCCAA
TAAAAAATTTTTGCCCTTTCAACAATTTGGCCGGGATATTGCCGATACCACCGATGC
CGTGCGGGATCCCCAAACCTTGGAAATTTTGGATATTACCCCCTGTTCCTTTGGCGG
CGTGTCCGTGATTACCCCCGGCACCAATACCTCCAATCAAGTGGCCGTGTTGTATC
AAGATGTGAATTGTACCGAAGTGCCCGTGGCCATTCATGCCGATCAATTGACCCCC
ACCTGGCGGGTGTATTCCACCGGCTCCAATGTGTTTCAAACCCGGGCCGGCTGTTT
GATTGGCGCCGAACATGTGAATAATTCCTATGAATGTGATATTCCCATTGGCGCCG
GCATTTGTGCCTCCTATCAAACCCAAACCAATTCCCCCCGGCGGGCCCGGTGAggaatt
aggaggtaatat*ATGAGGGAAGCGGTGATCGCCGAAGTATCGACTCAACTATCAGAGGTAGTTGGC*
*GTCATCGAGCGCCATCTCGAACCGACGTTGCTGGCCGTACAATTGTACGGCTCCGCAGTGGAA*
*GGCGGCCTGAAGCCACACAGTGATATTGATTTGCTGGTTACGGTGACCGTAAGGCTTGATGAA*
*ACAACGCGGCGAGCTTTGATCAACGACCTTTTGGAAACTTCGGCTTCCCCTGGAGAGAGCGAG*
*ATTCTCCGCGCTGTAGAAGTCACCATTGTTGTGCACGACGACATCATTCCGTGGCGTTATCCAG*
*CTAAGCGCGAACTGCAATTTGGAGAATGGCAGCGCAATGACATTCTTGCAGGTATCTTCGAGCC*
*AGCCACGATCGACATTGATCTGGCTATCTTGCTGACAAAAGCAAGAGAACATAGCGTTGCCTTG*
*GTAGGTCCAGCGGCGGAGGAACTCTTTGATCCGGTTCCTGAACAGGATCTATTTGAGGCGCTA*
*AATGAAACCTTAACGCTATGGAACTCGCCGCCCGACTGGGCTGGCGAIGAGCGAAATGTAGTG*
*CTTACGTTGTCCCGCATTTGGTACAGCGCAGTAACCGGCAAAATCGCGCCGAAGGATGTCGCT*
*GCCGACTGGGCAATGGAGCGCCTGCCGGCCCAGTATCAGCCCGTCATACTTGAAGCTAGACA*
*GGCTTATCTTGGACAAGAAGAAGATCGCTTGGCCTCGCGCGCAGATCAGTTGGAAGAATTTGT*
*CCACTACGTGAAAGGCGAGATCACCAAGGTAGTCGGCAAATAAtttttttaaggcagttattggtgcccttaaacg*
*cctgggGATCCtctggttattttaaaaaccaactttactcaggttccatacccgagaaaatccagcttaaagctgacatatctaggaaaatttt*

-continued

*cacattctaacgggagataccagaaca**atgaaaacccctttaactgaagccgtttccaccgctgactctcaaggtcgctttctgagcagcaccg*
*aattgcaaattgctttcggtcgtctacgtcaagctaatgctggtttgcaagccgctaaagctctgaccgacaatgcccagagcttggtaaatggtg*
*ctgcccaagccgtttataacaaattcccctacaccacccaaacccaaggcaacaactttgctgcggatcaacggggtaaagacaagtgtgcc*
*cggacatcggctactacctccgcatcgttacctactgcttagttgctggtggtaccggtcctttggatgagtacttgatcgccggtattga*

14. *cpcB*L7*His*TEV*ctxB-smR + cpc* (2199 nt) (see, FIG. 19, panel D)
ctxB from *Vibrio cholerae*, website http www.uniprot.org/uniprot/Q57193
UPPER CASE, *cpcB* gene + L7 linker (underlined) for homologous recombination (537 nt)
Lower case <caccatcaccatcaccatgataatttgtatttacaaggc>: His-tag + TEV cleavage site (39 nt)
UPPER CASE BOLD, *ctxB* gene + STOP CODON (312 nt)
Lower case bold RBS (ggaattaggaggtaatat) (18 nt)
*UPPER CASE ITALICS*, *smR* gene for antibiotic selection (792 nt)
*Lower case italics*, transcription terminator + intergenic seq + partial *cpcA* gene for homologous recombination (501 nt)

ATGTTCGACGTATTCACTCGGGTTGTTTCCCAAGCTGATGCTCGCGGCGAGTACCTCTCTG
GTTCTCAGTTAGATGCTTTGAGCGCTACCGTTGCTGAAGGCAACAAACGGATTGATTCTG
TTAACCGCATCACCGGTAATGCTTCCGCTATCGTTTCCAACGCTGCTCGTGCTTTGTTCGC
CGAACAGCCCCAATTAATCCAACCCGGTGGAAACGCCTACACCAGCCGTCGTATGGCTG
CTTGTTTGCGTGACATGGAAATCATCCTCCGCTATGTTACCTACGCAACCTTCACCGGCG
ACGCTTCCGTTCTAGAAGATCGTTGCTTGAACGGTCTCCGTGAAACCTACGTTGCCCTGG
GTGTTCCCGGTGCTTCCGTAGCTGCTGGCGTTCAAAAAATGAAAGAAGCTGCCCTGGACA
TCGTTAACGATCCCAATGGCATCACCCGTGGTGATTGCAGTGCTATCGTTGCTGAAATCG
CTGGTTACTTCGACCGCGCCGCTGCTGCCGTAGCCCCCATGCCTTGGCGCGTGATTcaccatc
accatcaccatgataatttgtatttacaaggcACCCCCCAAAATATTACCGATTTGTGTGCCGAATATCAT
AATACCCAAATTCATACCTTGAATGATAAAATTTTTTCCTATACCGAATCCTTGGCC
GGCAAACGGGAAATGGCCATTATTACCTTTAAAAATGGCGGCACCTTTCAAGTGGA
AGTGCCCGGCTCCCAACATATTGATTCCCAAAAAAAAGCCATTGAACGGATGAAAG
ATACCTTGCGGATTGCCTATTTGACCGAAGCCAAAGTGGAAAAATTGTGTGTGTGG
AATAATAAAACCCCCCATGCCATTGCCGCCATTTCCATGGCCAATTGAggaattaggaggta
atat*ATGAGGGAAGCGGTGATCGCCGAAGTATTCGACTCAACTATCAGAGGTAGTTGGCGTCATC*
*GAGCGCCATCTCGAACCGACGTTGCTGGCCGTACATTTGTACGGCTCCGCAGTGGATGGCGG*
*CCTGAAGCCACACAGTGATATrGATTTGCTGGTTACGGTGACCGTAAGGCTTGATGAAACAACG*
*CGGCGAGCTTTGATCAACGACCTTTTGGAAACTTCGGCTTCCCCTGGAGAGAGCGAGATTCTC*
*CGCGCTGTAGAAGTCACCATrGTrGTGCACGACGACATCATTCCGTGGCGTTATCCAGCTAAGC*
*GCGAACTGCAATTTGGAGAATGGCAGCATCAATGACATTCTTGCAGGTATCTTCGAGCCAGCCA*
*CGATCGACATTGATCTGGCTATCTTGCTGACAAAAGCAAGAGAACATAGCGTTGCCTTGGTAGG*
*TCCAGCGGCGGAGGAACTCTTTGATCCGGTTCCTGAACAGGATCTATTTGAGGCGCTAAATGAA*
*ACCTTAACGCTATGGAACTCGCCGCCCGACTGGGCTGGCGATGAGCGAAATGTAGTGCTTACG*
*TTGTCCCGCATTTGGTACAGCGCAGTAACCGGCAAAATCGCGCCGAAGGATGTCGCTGCCGAC*
*TGGGCAATGGAGCGCCTGCCGGCCCAGTATCAGCCCGTCATACTTGAAGCTAGACAGGCTTAT*
*CTTGGACAAGAAGAAGATCGCTTGGCCTCGCGCGCAGATCAGTTGGAAGAATTTGTCCACTAC*
*GTGAAAGGCGAGATCACCAAGGTAGTCGGCAAATAAtttttttaaggcagttattggtgcccttaaacscctgggGAT*
*CCtctggttattttaaaaaccaactttactcaggttccatacccgagaaaatccagcttaaagctgacatatctaggaaaattttcacattctaac*
*gggagataccagaaca**atgaaaacccctttaactgaagccgtttccaccgctgactctcaaggtcgctttctgagcagcaccgaattgcaaatt*
*gctttcggtcgtctacgtcaagctaatgctggtttgcaagccgctaaagctctgaccgacaatgcccagagcttggtaaatggtgctgcccaagc*
*cgtttataacaaattcccctacaccacccaaacccaaggcaacaactttgctgcggatcaacggggtaaagacaagtgtgcccggacatcg*
*gctactacctccgcatcgttacctactgcttagttgctggtggtaccggtcctttggcttagttgctggtggtaccggtcctttgg*

---

What is claimed is:

1. A cyanobacterial host cell comprising an expression unit comprising:

(i) a nucleic acid sequence comprising a transgene that encodes a biopharmaceutical protein, wherein the transgene is fused to the 3' end of a nucleic acid sequence that encodes a cyanobacteria β-subunit of phycocyanin (cpcB) polypeptide to produce a fusion polypeptide that comprises cpcB and the biopharmaceutical protein, and wherein the biopharmaceutical protein comprises:

an interferon polypeptide having at least 95% identity to SEQ ID NO: 1, a tPA polypeptide having at least 95% identity to the region of SEQ ID NO: 2 that lacks the signal peptide or having at least 95% identity to SEQ ID NO: 3, a TTFC polypeptide having at least 95% identity to SEQ ID NO: 15, a Cholera Toxin Fragment B polypeptide having at least 95% identity to SEQ ID NO: 18;

an insulin polypeptide having at least 95% identity to SEQ ID NO: 4, or a SARS-CoV2 polypeptide having at least 95% identity to SEQ ID NO: 16 or 17;

(ii) a nucleic acid sequence encoding a cyanobacteria α-subunit of phycocyanin (cpcA) polypeptide; and (iii) a nucleic acid sequence encoding a cyanobacterial cpcC1, cpcC2 and cpcD polypeptide.

2. The cyanobacterial host cell of claim 1, wherein the expression unit is operably linked to an endogenous cyanobacteria cpc promoter.

3. The cyanobacterial host cell of claim 1, wherein the fusion polypeptide comprises a protease cleavage site between cpcB and the biopharmaceutical protein encoded by the transgene.

4. The cyanobacterial host cell of claim 3, wherein the protease cleavage site is a Factor Xa cleavage site or Tobacco Etch Virus (TEV) cysteine protease cleavage site.

5. The cyanobacterial host cell of claim 1, wherein the expression unit comprises an antibiotic resistance gene between the transgene and cpcA.

6. The cyanobacterial host cell of claim 1, wherein the cyanobacteria are single-celled cyanobacteria.

7. The cyanobacterial host cell of claim 6, where the cyanobacteria are *Synechococcus* sp., *Thermosynechococcus elongatus, Synechocystis* sp., or *Cyanothece* sp.

8. The cyanobacterial host cell of claim 1, wherein the cyanobacteria are micro-colonial cyanobacteria.

9. The cyanobacterial host cell of claim 8, wherein the cyanobacteria are *Gloeocapsa magma, Gloeocapsa phylum, Gloeocapsa alpicola, Gloeocpasa atrata, Chroococcus* spp., or *Aphanothece* sp.

10. The cyanobacterial host cell of claim 1, wherein the cyanobacteria are filamentous cyanobacteria.

11. The cyanobacterial host cell of claim 10, wherein the cyanobacteria are *Oscillatoria* spp., *Nostoc* sp., *Anabaena* sp., or *Arthrospira* sp.

12. A cyanobacterial host cell culture comprising cyanobacteria of claim 1.

13. A method of producing a biopharmaceutical protein, the method comprising culturing the cyanobacterial host cell culture of claim 12 to express the protein.

14. A nucleic acid encoding a fusion polypeptide that comprises cpcB and a biopharmaceutical protein, and wherein the biopharmaceutical protein comprises:

an interferon polypeptide having at least 95% identity to SEQ ID NO: 1, a tPA polypeptide having at least 95% identity to the region of SEQ ID NO: 2 that lacks the signal peptide or having at least 95% identity to SEQ ID NO: 3, a TTFC polypeptide having at least 95% identity to SEQ ID NO: 15, a Cholera Toxin Fragment B polypeptide having at least 95% identity to SEQ ID NO: 18;

an insulin polypeptide having at least 95% identity to SEQ ID NO: 4, or a SARS-CoV2 polypeptide having at least 95% identity to SEQ ID NO: 16 or 17.

* * * * *

SEQUENCE LISTING

<160> NUMBER OF SEQ ID NOS: 25

<210> SEQ ID NO 1
<211> LENGTH: 165
<212> TYPE: PRT
<213> ORGANISM: Homo sapiens

<400> SEQUENCE: 1

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95
```

-continued

```
Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 2
<211> LENGTH: 562
<212> TYPE: PRT
<213> ORGANISM: Homo sapiens

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300
```

```
Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro


<210> SEQ ID NO 3
<211> LENGTH: 355
<212> TYPE: PRT
<213> ORGANISM: Homo sapiens

<400> SEQUENCE: 3

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
    50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
            100                 105                 110
```

```
Ala Ser His Pro Trp Gln Ala Ala Ile Phe Ala Lys His Arg Arg Ser
        115                 120                 125

Pro Gly Glu Arg Phe Leu Cys Gly Gly Ile Leu Ile Ser Ser Cys Trp
    130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
            180                 185                 190

Asp Asp Thr Tyr Asp Asn Asp Ile Ala Leu Leu Gln Leu Lys Ser Asp
        195                 200                 205

Ser Ser Arg Cys Ala Gln Glu Ser Ser Val Val Arg Thr Val Cys Leu
    210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
            260                 265                 270

His Leu Leu Asn Arg Thr Val Thr Asp Asn Met Leu Cys Ala Gly Asp
        275                 280                 285

Thr Arg Ser Gly Gly Pro Gln Ala Asn Leu His Asp Ala Cys Gln Gly
    290                 295                 300

Asp Ser Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
                325                 330                 335

Gly Val Tyr Thr Lys Val Thr Asn Tyr Leu Asp Trp Ile Arg Asp Asn
            340                 345                 350

Met Arg Pro
        355
```

<210> SEQ ID NO 4
<211> LENGTH: 86
<212> TYPE: PRT
<213> ORGANISM: Homo sapiens

<400> SEQUENCE: 4

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 5
<211> LENGTH: 2336
<212> TYPE: DNA

-continued

<213> ORGANISM: Artificial Sequence
<220> FEATURE:
<223> OTHER INFORMATION: Description of Artificial Sequence: Synthetic
polynucleotide

<400> SEQUENCE: 5
ctcgagtagg ctgtggttcc ctaggcaaca gtcttcccta ccccactgga aactaaaaaa 60
acgagaaaag ttcgcaccga acatcaattg cataatttta gccctaaaac ataagctgaa 120
cgaaactggt tgtcttccct tcccaatcca ggacaatctg agaatcccct gcaacattac 180
ttaacaaaaa agcaggaata aaattaacaa gatgtaacag acataagtcc catcaccgtt 240
gtataaagtt aactgtggga ttgcaaaagc attcaagcct aggcgctgag ctgtttgagc 300
atcccggtgg cccttgtcgc tgcctccgtg tttctccctg gatttattta ggtaatatct 360
ctcataaatc cccgggtagt taacgaaagt taatggagat cagtaacaat aactctaggg 420
tcattacttt ggactccctc agtttatccg gggaattgt gtttaagaaa atcccaactc 480
ataaagtcaa gtaggagatt aattcaatgt gtgacttgcc tcagacgcat tctttgggaa 540
gccgacgcac actgatgctg ctcgcccaaa tgcgccggat ctccttattc tcctgtctca 600
aggatcggca tgacttcggc ttccctcagg aggagtttgg aaatcagttc caaaaggccg 660
aaaccattcc ggtcctccat gaaatgattc aacagatctt taacttattc agtaccaaag 720
acagcagtgc ggcctgggac gaaacattac tcgataaatt ctacacggaa ttataccaac 780
agttgaacga cttagaagcc tgtgtaatcc aaggtgttgg tgtcactgag actccattaa 840
tgaaagaaga ctctattctg gccgtccgca agtatttcca gcgaatcaca ctgtatttga 900
aagagaaaaa gtattctccg tgtgcgtggg aggtagtacg ggctgaaatc atgcggtcct 960
tctctttaag cacaaacctc caggaatctc tgcgctccaa agaatgaaga tctgcggccg 1020
cgttgatcgg cacgtaagag gttccaactt tcaccataat gaaataagat cactaccggg 1080
cgtatttttt gagttatcga gattttcagg agctaaggaa gctaaaatgg agaaaaaaat 1140
cactggatat accaccgttg atatatccca atggcatcgt aaagaacatt ttgaggcatt 1200
tcagtcagtt gctcaatgta cctataacca gaccgttcag ctggatatta cggccttttt 1260
aaagaccgta aagaaaaata agcacaagtt ttatccggcc tttattcaca ttcttgcccg 1320
cctgatgaat gctcatccgg aattccgtat ggcaatgaaa gacggtgagc tggtgatatg 1380
ggatagtgtt cacccttgtt acaccgtttt ccatgagcaa actgaaacgt tttcatcgct 1440
ctggagtgaa taccacgacg atttccggca gtttctacac atatattcgc aagatgtggc 1500
gtgttacggt gaaaacctgg cctatttccc taaagggttt attgagaata tgtttttcgt 1560
ctcagccaat ccctgggtga gtttcaccag ttttgattta aacgtggcca atatggacaa 1620
cttcttcgcc cccgttttca ccatgggcaa atattatacg caaggcgaca aggtgctgat 1680
gccgctggcg attcaggttc atcatgccgt ctgtgatggc ttccatgtcg gcagaatgct 1740
taatgaatta caacagtact gcgatgagtg gcagggcggg gcgtaatttt tttaaggcag 1800
ttattggtgc ccttaaacgc ctggggatcc tctggttatt ttaaaaacca actttactca 1860
ggttccatac ccgagaaaat ccagcttaaa gctgacatat ctaggaaaat tttcacattc 1920
taacgggaga taccagaaca atgaaaaccc ctttaactga agccgtttcc accgctgact 1980
ctcaaggtcg ctttctgagc agcaccgaat tgcaaattgc tttcggtcgt ctacgtcaag 2040
ctaatgctgg tttgcaagcc gctaaagctc tgaccgacaa tgcccagagc ttggtaaatg 2100
gtgctgccca agccgtttat aacaaattcc cctacaccac ccaaacccaa ggcaacaact 2160

-continued

```
ttgctgcgga tcaacggggt aaagacaagt gtgcccggga catcggctac tacctccgca   2220

tcgttaccta ctgcttagtt gctggtggta ccggtccttt ggatgagtac ttgatcgccg   2280

gtattgatga aatcaaccgc acctttgacc tctcccccag ctggtatgtt ctcgag       2336
```

```
<210> SEQ ID NO 6
<211> LENGTH: 2340
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

ctcgagccgc atcaccggta atgcttccgc tatcgtttcc aacgctgctc gtgctttgtt     60

cgccgaacag ccccaattaa tccaacccgg tggaaacgcc tacaccagcc gtcgtatggc    120

tgcttgtttg cgtgacatgg aaatcatcct ccgctatgtt acctacgcaa ccttcaccgg    180

cgacgcttcc gttctagaag atcgttgctt gaacggtctc cgtgaaacct acgttgccct    240

gggtgttccc ggtgcttccg tagctgctgg cgttcaaaaa atgaaagaag ctgccctgga    300

catcgttaac gatcccaatg gcatcacccg tggtgattgc agtgctatcg ttgctgaaat    360

cgctggttac ttcgaccgcg ccgctgctgc cgtagcctag tctggttatt ttaaaaacca    420

actttactca ggttccatac ccgagaaaat ccagcttaaa gctgacatat ctaggaaaat    480

tttcacattc taacgggaga taccagaaca atgtgtgact tgcctcagac gcattctttg    540

ggaagccgac gcacactgat gctgctcgcc caaatgcgcc ggatctcctt attctcctgt    600

ctcaaggatc ggcatgactt cggcttccct caggaggagt ttggaaatca gttccaaaag    660

gccgaaacca ttccggtcct ccatgaaatg attcaacaga tctttaactt attcagtacc    720

aaagacagca gtgcggcctg ggacgaaaca ttactcgata aattctacac ggaattatac    780

caacagttga acgacttaga agcctgtgta atccaaggtg ttggtgtcac tgagactcca    840

ttaatgaaag aagactctat tctggccgtc cgcaagtatt tccagcgaat cacactgtat    900

ttgaaagaga aaaagtattc tccgtgtgcg tgggaggtag tacgggctga aatcatgcgg    960

tccttctctt taagcacaaa cctccaggaa tctctgcgct ccaaagaatg aagatctgcg   1020

gccgcgttga tcggcacgta agaggttcca actttcacca taatgaaata agatcactac   1080

cgggcgtatt ttttgagtta tcgagatttt caggagctaa ggaagctaaa atggagaaaa   1140

aaatcactgg atataccacc gttgatatat cccaatggca tcgtaaagaa cattttgagg   1200

catttcagtc agttgctcaa tgtacctata accagaccgt tcagctggat attacggcct   1260

ttttaaagac cgtaaagaaa aataagcaca agttttatcc ggcctttatt cacattcttg   1320

cccgcctgat gaatgctcat ccggaattcc gtatggcaat gaaagacggt gagctggtga   1380

tatgggatag tgttcaccct tgttacaccg ttttccatga gcaaactgaa acgttttcat   1440

cgctctggag tgaataccac gacgatttcc ggcagtttct acacatatat tcgcaagatg   1500

tggcgtgtta cggtgaaaac ctggcctatt tccctaaagg gtttattgag aatatgtttt   1560

tcgtctcagc caatccctgg gtgagtttca ccagttttga tttaaacgtg gccaatatgg   1620

acaacttctt cgcccccgtt ttcaccatgg gcaaatatta tacgcaaggc gacaaggtgc   1680

tgatgccgct ggcgattcag gttcatcatg ccgtctgtga tggcttccat gtcggcagaa   1740

tgcttaatga attacaacag tactgcgatg agtggcaggg cggggcgtaa ttttttttaag   1800

gcagttattg gtgcccttaa acgcctgggg atcctctggt tattttaaaa accaacttta   1860
```

-continued

```
ctcaggttcc atacccgaga aaatccagct taaagctgac atatctagga aaattttcac      1920

attctaacgg gagataccag aacaatgaaa acccctttaa ctgaagccgt ttccaccgct      1980

gactctcaag gtcgctttct gagcagcacc gaattgcaaa ttgctttcgg tcgtctacgt      2040

caagctaatg ctggtttgca agccgctaaa gctctgaccg acaatgccca gagcttggta      2100

aatggtgctg cccaagccgt ttataacaaa ttcccctaca ccacccaaac ccaaggcaac      2160

aactttgctg cggatcaacg gggtaaagac aagtgtgccc gggacatcgg ctactacctc      2220

cgcatcgtta cctactgctt agttgctggt ggtaccggtc ctttggatga gtacttgatc      2280

gccggtattg atgaaatcaa ccgcaccttt gacctctccc ccagctggta tgttctcgag      2340
```

<210> SEQ ID NO 7
<211> LENGTH: 2361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ctcgagatgt tcgacgtatt cactcgggtt gtttcccaag ctgatgctcg cggcgagtac        60

ctctctggtt ctcagttaga tgctttgagc gctaccgttg ctgaaggcaa caaacggatt       120

gattctgtta accgcatcac cggtaatgct tccgctatcg tttccaacgc tgctcgtgct       180

ttgttcgccg aacagcccca attaatccaa cccggtggaa acgcctacac cagccgtcgt       240

atggctgctt gtttgcgtga catggaaatc atcctccgct atgttaccta cgcaaccttc       300

accggcgacg cttccgttct agaagatcgt tgcttgaacg gtctccgtga aacctacgtt       360

gccctgggtg ttcccggtgc ttccgtagct gctggcgttc aaaaaatgaa agaagctgcc       420

ctggacatcg ttaacgatcc caatggcatc acccgtggtg attgcagtgc tatcgttgct       480

gaaatcgctg gttacttcga ccgcgccgct gctgccgtag ccatcgaagg gcgatgtgac       540

ttgcctcaga cgcattcttt gggaagccga cgcacactga tgctgctcgc ccaaatgcgc       600

cggatctcct tattctcctg tctcaaggat cggcatgact tcggcttccc tcaggaggag       660

tttggaaatc agttccaaaa ggccgaaacc attccggtcc tccatgaaat gattcaacag       720

atctttaact tattcagtac caaagacagc agtgcggcct gggacgaaac attactcgat       780

aaattctaca cggaattata ccaacagttg aacgacttag aagcctgtgt aatccaaggt       840

gttggtgtca ctgagactcc attaatgaaa gaagactcta ttctggccgt ccgcaagtat       900

ttccagcgaa tcacactgta tttgaaagag aaaaagtatt ctccgtgtgc gtgggaggta       960

gtacgggctg aaatcatgcg gtccttctct ttaagcacaa acctccagga atctctgcgc      1020

tccaaagaat gaagatctgc ggccgcgttg atcggcacgt aagaggttcc aactttcacc      1080

ataatgaaat aagatcacta ccgggcgtat tttttgagtt atcgagattt tcaggagcta      1140

aggaagctaa aatggagaaa aaaatcactg gatataccac cgttgatata tcccaatggc      1200

atcgtaaaga acattttgag gcatttcagt cagttgctca atgtacctat aaccagaccg      1260

ttcagctgga tattacggcc tttttaaaga ccgtaaagaa aaataagcac aagttttatc      1320

cggcctttat tcacattctt gcccgcctga tgaatgctca tccggaattc cgtatggcaa      1380

tgaaagacgg tgagctggtg atatgggata gtgttcaccc ttgttacacc gttttccatg      1440

agcaaactga aacgttttca tcgctctgga gtgaatacca cgacgatttc cggcagtttc      1500

tacacatata ttcgcaagat gtggcgtgtt acggtgaaaa cctggcctat ttccctaaag      1560
```

-continued

```
ggtttattga gaatatgttt ttcgtctcag ccaatccctg ggtgagtttc accagttttg   1620

atttaaacgt ggccaatatg gacaacttct tcgcccccgt tttcaccatg ggcaaatatt   1680

atacgcaagg cgacaaggtg ctgatgccgc tggcgattca ggttcatcat gccgtctgtg   1740

atggcttcca tgtcggcaga atgcttaatg aattacaaca gtactgcgat gagtggcagg   1800

gcggggcgta attttttaa ggcagttatt ggtgccctta aacgcctggg gatcctctgg   1860

ttattttaaa aaccaacttt actcaggttc catacccgag aaaatccagc ttaaagctga   1920

catatctagg aaaattttca cattctaacg ggagatacca gaacaatgaa aaccccttta   1980

actgaagccg tttccaccgc tgactctcaa ggtcgctttc tgagcagcac cgaattgcaa   2040

attgctttcg gtcgtctacg tcaagctaat gctggtttgc aagccgctaa agctctgacc   2100

gacaatgccc agagcttggt aaatggtgct gcccaagccg tttataacaa attcccctac   2160

accacccaaa cccaaggcaa caactttgct gcggatcaac ggggtaaaga caagtgtgcc   2220

cgggacatcg gctactacct ccgcatcgtt acctactgct tagttgctgg tggtaccggt   2280

cctttggatg agtacttgat cgccggtatt gatgaaatca accgcacctt tgacctctcc   2340

cccagctggt atgttctcga g                                             2361
```

```
<210> SEQ ID NO 8
<211> LENGTH: 2361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

```
ctcgagatgt tcgacgtatt cactcgggtt gtttcccaag ctgatgctcg cggcgagtac     60

ctctctggtt ctcagttaga tgctttgagc gctaccgttg ctgaaggcaa caaacggatt    120

gattctgtta accgcatcac cggtaatgct tccgctatcg tttccaacgc tgctcgtgct    180

ttgttcgccg aacagcccca attaatccaa cccggtggaa acgcctacac cagccgtcgt    240

atggctgctt gtttgcgtga catggaaatc atcctccgct atgttaccta cgcaaccttc    300

accggcgacg cttccgttct agaagatcgt tgcttgaacg gtctccgtga aacctacgtt    360

gccctgggtg ttcccggtgc ttccgtagct gctggcgttc aaaaaatgaa agaagctgcc    420

ctggacatcg ttaacgatcc caatggcatc acccgtggtg attgcagtgc tatcgttgct    480

gaaatcgctg gttacttcga ccgcgccgct gctgccgtag ccatcgaagg gcgatgtgat    540

ctgcctcaaa cccacagcct gggtagcagg aggaccttga tgctcctggc acagatgagg    600

agaatctctc ttttctcctg cttgaaggac agacatgact ttggatttcc ccaggaggag    660

tttggcaacc agttccaaaa ggctgaaacc atccctgtcc tccatgagat gatccagcag    720

atcttcaatc tcttcagcac aaaggactca tctgctgctt gggatgagac cctcctagac    780

aaattctaca ctgaactcta ccagcagctg aatgacctgg aagcctgtgt gatacagggg    840

gtgggggtga cagagactcc cctgatgaag gaggactcca ttctggctgt gaggaaatac    900

ttccaaagaa tcactctcta tctgaaagag aagaaataca gcccttgtgc ctgggaggtt    960

gtcagagcag aaatcatgag atctttttct ttgtcaacaa acttgcaaga aagtttaaga   1020

agtaaggaat gaagatctgc ggccgcgttg atcggcacgt aagaggttcc aactttcacc   1080

ataatgaaat aagatcacta ccgggcgtat tttttgagtt atcgagattt tcaggagcta   1140

aggaagctaa aatggagaaa aaaatcactg gatataccac cgttgatata tcccaatggc   1200
```

-continued

```
atcgtaaaga acattttgag gcatttcagt cagttgctca atgtacctat aaccagaccg   1260

ttcagctgga tattacggcc tttttaaaga ccgtaaagaa aaataagcac aagttttatc   1320

cggcctttat tcacattctt gcccgcctga tgaatgctca tccggaattc cgtatggcaa   1380

tgaaagacgg tgagctggtg atatgggata gtgttcaccc ttgttacacc gttttccatg   1440

agcaaactga aacgttttca tcgctctgga gtgaatacca cgacgatttc cggcagtttc   1500

tacacatata ttcgcaagat gtggcgtgtt acggtgaaaa cctggcctat ttccctaaag   1560

ggtttattga gaatatgttt ttcgtctcag ccaatccctg ggtgagtttc accagttttg   1620

atttaaacgt ggccaatatg gacaacttct tcgcccccgt tttcaccatg ggcaaatatt   1680

atacgcaagg cgacaaggtg ctgatgccgc tggcgattca ggttcatcat gccgtctgtg   1740

atggcttcca tgtcggcaga atgcttaatg aattacaaca gtactgcgat gagtggcagg   1800

gcggggcgta attttttaa ggcagttatt ggtgccctta aacgcctggg gatcctctgg   1860

ttattttaaa aaccaacttt actcaggttc catacccgag aaaatccagc ttaaagctga   1920

catatctagg aaaatttca cattctaacg ggagatacca gaacaatgaa aacccctta   1980

actgaagccg tttccaccgc tgactctcaa ggtcgctttc tgagcagcac cgaattgcaa   2040

attgctttcg gtcgtctacg tcaagctaat gctggtttgc aagccgctaa agctctgacc   2100

gacaatgccc agagcttggt aaatggtgct gcccaagccg tttataacaa attcccctac   2160

accacccaaa cccaaggcaa caactttgct gcggatcaac ggggtaaaga caagtgtgcc   2220

cgggacatcg gctactacct ccgcatcgtt acctactgct tagttgctgg tggtaccggt   2280

cctttggatg agtacttgat cgccggtatt gatgaaatca accgcacctt tgacctctcc   2340

cccagctggt atgttctcga g                                             2361
```

<210> SEQ ID NO 9
<211> LENGTH: 2379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
ctcgagatgt tcgacgtatt cactcgggtt gtttcccaag ctgatgctcg cggcgagtac     60

ctctctggtt ctcagttaga tgctttgagc gctaccgttg ctgaaggcaa caaacggatt    120

gattctgtta accgcatcac cggtaatgct tccgctatcg tttccaacgc tgctcgtgct    180

ttgttcgccg aacagcccca attaatccaa cccggtggaa acgcctacac cagccgtcgt    240

atggctgctt gtttgcgtga catggaaatc atcctccgct atgttaccta cgcaaccttc    300

accggcgacg cttccgttct agaagatcgt tgcttgaacg gtctccgtga aacctacgtt    360

gccctgggtg ttcccggtgc ttccgtagct gctggcgttc aaaaaatgaa agaagctgcc    420

ctggacatcg ttaacgatcc caatggcatc acccgtggtg attgcagtgc tatcgttgct    480

gaaatcgctg gttacttcga ccgcgccgct gctgccgtag cccaccatca ccatcaccat    540

atcgaagggc gatgtgactt gcctcagacg cattctttgg gaagccgacg cacactgatg    600

ctgctcgccc aaatgcgccg gatctcctta ttctcctgtc tcaaggatcg gcatgacttc    660

ggcttccctc aggaggagtt tggaaatcag ttccaaaagg ccgaaaccat tccggtcctc    720

catgaaatga ttcaacagat ctttaactta ttcagtacca aagacagcag tgcggcctgg    780

gacgaaacat tactcgataa attctacacg gaattatacc aacagttgaa cgacttagaa    840
```

-continued gcctgtgtaa tccaaggtgt tggtgtcact gagactccat taatgaaaga agactctatt 900
ctggccgtcc gcaagtattt ccagcgaatc acactgtatt tgaaagagaa aaagtattct 960
ccgtgtgcgt gggaggtagt acgggctgaa atcatgcggt ccttctcttt aagcacaaac 1020
ctccaggaat ctctgcgctc caaagaatga agatctgcgg ccgcgttgat cggcacgtaa 1080
gaggttccaa ctttcaccat aatgaaataa gatcactacc gggcgtattt tttgagttat 1140
cgagattttc aggagctaag gaagctaaaa tggagaaaaa aatcactgga tataccaccg 1200
ttgatatatc ccaatggcat cgtaaagaac attttgaggc atttcagtca gttgctcaat 1260
gtacctataa ccagaccgtt cagctggata ttacggcctt tttaaagacc gtaaagaaaa 1320
ataagcacaa gttttatccg gcctttattc acattcttgc ccgcctgatg aatgctcatc 1380
cggaattccg tatggcaatg aaagacggtg agctggtgat atgggatagt gttcaccctt 1440
gttacaccgt tttccatgag caaactgaaa cgttttcatc gctctggagt gaataccacg 1500
acgatttccg gcagtttcta cacatatatt cgcaagatgt ggcgtgttac ggtgaaaacc 1560
tggcctattt ccctaaaggg tttattgaga atatgttttt cgtctcagcc aatccctggg 1620
tgagtttcac cagttttgat ttaaacgtgg ccaatatgga caacttcttc gcccccgttt 1680
tcaccatggg caaatattat acgcaaggcg acaaggtgct gatgccgctg gcgattcagg 1740
ttcatcatgc cgtctgtgat ggcttccatg tcggcagaat gcttaatgaa ttacaacagt 1800
actgcgatga gtggcagggc ggggcgtaat ttttttaagg cagttattgg tgcccttaaa 1860
cgcctgggga tcctctggtt attttaaaaa ccaactttac tcaggttcca tacccgagaa 1920
aatccagctt aaagctgaca tatctaggaa aattttcaca ttctaacggg agataccaga 1980
acaatgaaaa cccctttaac tgaagccgtt tccaccgctg actctcaagg tcgctttctg 2040
agcagcaccg aattgcaaat tgctttcggt cgtctacgtc aagctaatgc tggtttgcaa 2100
gccgctaaag ctctgaccga caatgcccag agcttggtaa atggtgctgc ccaagccgtt 2160
tataacaaat tcccctacac cacccaaacc caaggcaaca actttgctgc ggatcaacgg 2220
ggtaaagaca agtgtgcccg ggacatcggc tactacctcc gcatcgttac ctactgctta 2280
gttgctggtg gtaccggtcc tttggatgag tacttgatcg ccggtattga tgaaatcaac 2340
cgcacctttg acctctcccc cagctggtat gttctcgag 2379

<210> SEQ ID NO 10
<211> LENGTH: 2420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
ctcgagggaa agtaggctgt ggttccctag gcaacagtct tccctacccc actggaaact 60
aaaaaaacga gaaaagttcg caccgaacat caattgcata attttagccc taaaacataa 120
gctgaacgaa actggttgtc ttcccttccc aatccaggac aatctgagaa tcccctgcaa 180
cattacttaa caaaaaagca ggaataaaat taacaagatg taacagacat aagtcccatc 240
accgttgtat aaagttaact gtgggattgc aaaagcattc aagcctaggc gctgagctgt 300
ttgagcatcc cggtggccct tgtcgctgcc tccgtgtttc tccctggatt tatttaggta 360
atatctctca taaatccccg ggtagttaac gaaagttaat ggagatcagt aacaataact 420
ctagggtcat tactttggac tccctcagtt tatccggggg aattgtgttt aagaaaatcc 480

```
caactcataa agtcaagtag gagattaatt caatgagtca catccagaga gaaactagtt    540

gttcccgacc tcgtttgaat agcaatatgg atgcagatct gtacggatat aaatgggcgc    600

gagataacgt aggccaatct ggggccacta tttatcggtt atatggcaaa ccagatgctc    660

ccgaactgtt tctcaaacat ggcaaagggt ctgtggccaa tgatgttacc gatgaaatgg    720

tgcggttgaa ctggttgaca gaatttatgc ccctcccgac catcaaacat tttatcagga    780

ctccagacga tgcatggcta ttaactacgg ccattcctgg gaaaactgcc tttcaggtgt    840

tggaagaata tcccgattct ggtgagaata tcgtcgatgc gttagcggtt tttctaagac    900

gtctacatag cattcccgtt tgcaattgtc cctttaattc ggaccgggtg ttccgcttgg    960

cgcaggctca gtcccggatg aataacggtt tggtagatgc ctcggacttt gatgatgaac   1020

ggaacggctg gcccgttgaa caggtttgga aagagatgca taagctgctg cccttctccc   1080

ccgacagcgt tgttactcat ggagattttt ctctcgataa tctgattttc gacgaaggca   1140

agctaattgg ctgtatcgat gtgggacggg tagggattgc ggaccggtat caagacctag   1200

caattttgtg gaactgccta ggtgaatttt ccccagcct acaaaaacgg ctgtttcaaa    1260

aatacggaat cgataatccc gacatgaaca aattacaatt tcatctgatg ctagatgagt   1320

tctttcacca tcaccatcac catatcgaag ggcgatgtga cttgcctcag acgcattctt   1380

tgggaagccg acgcacactg atgctgctcg cccaaatgcg ccggatctcc ttattctcct   1440

gtctcaagga tcggcatgac ttcggcttcc ctcaggagga gtttggaaat cagttccaaa   1500

aggccgaaac cattccggtc ctccatgaaa tgattcaaca gatctttaac ttattcagta   1560

ccaaagacag cagtgcggcc tgggacgaaa cattactcga taaattctac acggaattat   1620

accaacagtt gaacgactta gaagcctgtg taatccaagg tgttggtgtc actgagactc   1680

cattaatgaa agaagactct attctggccg tccgcaagta tttccagcga atcacactgt   1740

atttgaaaga gaaaaagtat tctccgtgtg cgtgggaggt agtacgggct gaaatcatgc   1800

ggtccttctc tttaagcaca aacctccagg aatctctgcg ctccaaagaa tgattttttt   1860

aaggcagtta ttggtgccct taaacgcctg gggatcctct ggttatttta aaaaccaact   1920

ttactcaggt tccatacccg agaaaatcca gcttaaagct gacatatcta ggaaaatttt   1980

cacattctaa cgggagatac cagaacaatg aaaacccctt taactgaagc cgtttccacc   2040

gctgactctc aaggtcgctt tctgagcagc accgaattgc aaattgcttt cggtcgtcta   2100

cgtcaagcta atgctggttt gcaagccgct aaagctctga ccgacaatgc ccagagcttg   2160

gtaaatggtg ctgcccaagc cgtttataac aaattcccct acaccaccca aacccaaggc   2220

aacaactttg ctgcggatca acggggtaaa gacaagtgtg cccgggacat cggctactac   2280

ctccgcatcg ttacctactg cttagttgct ggtggtaccg gtcctttgga tgagtacttg   2340

atcgccggta ttgatgaaat caaccgcacc tttgacctct cccccagctg gtatgttgaa   2400

gctctgaaat acatctcgag                                             2420
```

```
<210> SEQ ID NO 11
<211> LENGTH: 2705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
```

```
ctcgaggcca tgtcccaaat tcttgatccc atccccaaca accagccatc agccttattc     60
```

-continued

```
tgttgctacg tcaatgccac caatcaaatc caagtggccc gcattaccaa tgtccctaat    120
tggtattttg aaagagttgt gttccctggt caacggttag tatttgaggc agtgcccagc    180
gctcagttag aaattcatac tggcatgatg gccagctcga ttatttcgga caccattccc    240
tgcgaacaac tgagtattga tcccgacgga ttagcagcgg gcggtttcat ctctccagaa    300
aaagaacacg agtccgagga tatgacttcc caatccttag tggcttagca atgaattaat    360
gaattggaat acttaggcca tgccaccggc cggcaatgga tagtccacgg acaaagcact    420
aagaaaaagg tatagggatg gaaagcagaa actgttaatt actctctccg atgggtaacc    480
accaccgtca tataattgag cggaaagtat ggcaaccagg ccctgaactc aattagtgga    540
ataacgcggt cctgcaggat tctgaaatga gctgttgaca attaatcatc cggctcgtat    600
aatgtgtgga aattgtgagc ggataacaat taggaggtta attaacaatg agtcacatcc    660
agagagaaac tagttgttcc cgacctcgtt tgaatagcaa tatggatgca gatctgtacg    720
gatataaatg ggcgcgagat aacgtaggcc aatctggggc cactatttat cggttatatg    780
gcaaaccaga tgctcccgaa ctgtttctca aacatggcaa agggtctgtg gccaatgatg    840
ttaccgatga aatggtgcgg ttgaactggt tgacagaatt tatgcccctc ccgaccatca    900
aacattttat caggactcca gacgatgcat ggctattaac tacggccatt cctgggaaaa    960
ctgcctttca ggtgttggaa gaatatcccg attctggtga gaatatcgtc gatgcgttag   1020
cggtttttct aagacgtcta catagcattc ccgtttgcaa ttgtcccttt aattcggacc   1080
gggtgttccg cttggcgcag gctcagtccc ggatgaataa cggtttggta gatgcctcgg   1140
actttgatga tgaacggaac ggctggcccg ttgaacaggt ttggaaagag atgcataagc   1200
tgctgccctt ctcccccgac agcgttgtta ctcatggaga tttttctctc gataatctga   1260
ttttcgacga aggcaagcta attggctgta tcgatgtggg acgggtaggg attgcggacc   1320
ggtatcaaga cctagcaatt ttgtggaact gcctaggtga attttccccc agcctacaaa   1380
aacggctgtt tcaaaaatac ggaatcgata atcccgacat gaacaaatta caatttcatc   1440
tgatgctaga tgagttcttt caccatcacc atcaccatat cgaagggcga tgtgacttgc   1500
ctcagacgca ttctttggga agccgacgca cactgatgct gctcgcccaa atgcgccgga   1560
tctccttatt ctcctgtctc aaggatcggc atgacttcgg cttccctcag gaggagtttg   1620
gaaatcagtt ccaaaaggcc gaaaccattc cggtcctcca tgaaatgatt caacagatct   1680
ttaacttatt cagtaccaaa gacagcagtg cggcctggga cgaaacatta ctcgataaat   1740
tctacacgga attataccaa cagttgaacg acttagaagc ctgtgtaatc caaggtgttg   1800
gtgtcactga gactccatta atgaaagaag actctattct ggccgtccgc aagtatttcc   1860
agcgaatcac actgtatttg aaagagaaaa agtattctcc gtgtgcgtgg gaggtagtac   1920
gggctgaaat catgcggtcc ttctctttaa gcacaaacct ccaggaatct ctgcgctcca   1980
aagaatgagg atcctccttg gtgtaatgcc aactgaataa tctgcaaatt gcactctcct   2040
tcaatggggg gtgcttttg cttgactgag taatcttctg attgctgatc ttgattgcca   2100
tcgatcgccg gggagtccgg ggcagttacc attagagagt ctagagaatt aatccatctt   2160
cgatagagga attatggggg aagaacccta ggcaattgat ggccatgcgt tatggctgta   2220
tccccattgt gcggcggaca gggggtttgg tggatacggt atccttctac gatcctatca   2280
atgaagccgg caccggctat tgctttgacc gttatgaacc cctggattgc tttacggcca   2340
tggtgcgggc ctgggagggt ttccgtttca aggcagattg gcaaaaatta cagcaacggg   2400
ccatgcgggc agactttagt tggtaccgtt ccgccgggga atatatcaaa gtttataagg   2460
```

-continued

```
gcgtggtggg gaaaccggag gaattaagcc ccatggaaga ggaaaaaatc gctgagttaa   2520

ctgcttccta tcgctaacaa tctcccggca gtgaagtaaa atcctgaacc ctaatcccgc   2580

tccactgccg accccaattc tccttgccta ggcaaatttg aaaatttttt ctgatcaatg   2640

cttgtggtga agcaaaagct atgttaacgt tataaatcgt gccaatgaag cacaacgggc   2700

tcgag                                                               2705
```

<210> SEQ ID NO 12
<211> LENGTH: 2949
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
ctcgagatgt tcgacgtatt cactcgggtt gtttcccaag ctgatgctcg cggcgagtac     60

ctctctggtt ctcagttaga tgctttgagc gctaccgttg ctgaaggcaa caaacggatt    120

gattctgtta accgcatcac cggtaatgct tccgctatcg tttccaacgc tgctcgtgct    180

ttgttcgccg aacagcccca attaatccaa cccggtggaa acgcctacac cagccgtcgt    240

atggctgctt gtttgcgtga catggaaatc atcctccgct atgttaccta cgcaaccttc    300

accggcgacg cttccgttct agaagatcgt tgcttgaacg gtctccgtga aacctacgtt    360

gccctgggtg ttcccggtgc ttccgtagct gctggcgttc aaaaaatgaa agaagctgcc    420

ctggacatcg ttaacgatcc caatggcatc acccgtggtg attgcagtgc tatcgttgct    480

gaaatcgctg gttacttcga ccgcgccgct gctgccgtag cccaccatca ccatcaccat    540

atcgaagggc gatcctatca aggcaattcc gattgttatt ttggcaatgg ctccgcctat    600

cggggcaccc attccttgac cgaatccggc gcctcctgtt tgccctggaa ttccatgatt    660

ttgattggca aagtgtatac cgcccaaaat ccctccgccc aagccttggg cttgggcaaa    720

cataattatt gtcggaatcc cgatggcgat gccaaaccct ggtgtcatgt gttgaagaat    780

cggcggttga cctgggaata ttgtgatgtg ccctcctgtt ccacctgtgg cttgcggcaa    840

tattcccaac cccaatttcg gattaaaggc ggcttgtttg ccgatattgc ctcccatccc    900

tggcaagccg ccatctttgc caaacatcgg cggtctcccg gcgaacggtt cttgtgtggc    960

ggcattttga tttcctcctg ttggattttg tccgccgccc attgttttca agaacggttt   1020

cctccccatc atttgaccgt gattttgggc cggacctatc gggtggtgcc cggcgaagaa   1080

gaacagaaat ttgaagtgga gaaatatatt gtgcataaag aatttgatga tgatacctat   1140

gataatgata ttgccttgtt gcaattgaaa tccgattcct cccggtgtgc ccaagaatcc   1200

tccgtggtgc ggaccgtgtg tttgcctccc gccgatttgc aattgcccga ttggaccgaa   1260

tgtgaattgt ccggctatgg caaacatgaa gccttgtctc ccttttattc cgaacggttg   1320

aaagaagccc atgtgcggtt gtatccctcc tcccggtgta cctcccaaca tttgttgaat   1380

cggaccgtga ccgataatat gttgtgtgcc ggcgataccc ggtccggcgg cccccaagcc   1440

aatttgcatg atgcctgtca aggcgattcc ggcggcccct tggtgtgttt gaatgatggc   1500

cggatgacct tggtgggcat tatttcctgg ggcttgggct gtggccagaa agatgtgccc   1560

ggcgtgtata ccaaagtgac caattatttg gattggattc gggataatat gcggccctaa   1620

agatctgcgg ccgcgttgat cggcacgtaa gaggttccaa ctttcaccat aatgaaataa   1680

gatcactacc gggcgtattt tttgagttat cgagattttc aggagctaag gaagctaaaa   1740
```

-continued tggagaaaaa aatcactgga tataccaccg ttgatatatc ccaatggcat cgtaaagaac 1800
attttgaggc atttcagtca gttgctcaat gtacctataa ccagaccgtt cagctggata 1860
ttacggcctt tttaaagacc gtaaagaaaa ataagcacaa gttttatccg gcctttattc 1920
acattcttgc ccgcctgatg aatgctcatc cggaattccg tatggcaatg aaagacggtg 1980
agctggtgat atgggatagt gttcaccctt gttacaccgt tttccatgag caaactgaaa 2040
cgttttcatc gctctggagt gaataccacg acgatttccg gcagtttcta cacatatatt 2100
cgcaagatgt ggcgtgttac ggtgaaaacc tggcctattt ccctaaaggg tttattgaga 2160
atatgttttt cgtctcagcc aatccctggg tgagtttcac cagttttgat ttaaacgtgg 2220
ccaatatgga caacttcttc gcccccgttt tcaccatggg caaatattat acgcaaggcg 2280
acaaggtgct gatgccgctg gcgattcagg ttcatcatgc cgtctgtgat ggcttccatg 2340
tcggcagaat gcttaatgaa ttacaacagt actgcgatga gtggcagggc ggggcgtaat 2400 tttttaagg cagttattgg tgcccttaaa cgcctgggga tcctctggtt attttaaaaa 2460
ccaactttac tcaggttcca tacccgagaa aatccagctt aaagctgaca tatctaggaa 2520
aattttcaca ttctaacggg agataccaga acaatgaaaa cccctttaac tgaagccgtt 2580
tccaccgctg actctcaagg tcgctttctg agcagcaccg aattgcaaat tgctttcggt 2640
cgtctacgtc aagctaatgc tggtttgcaa gccgctaaag ctctgaccga caatgcccag 2700
agcttggtaa atggtgctgc ccaagccgtt tataacaaat tcccctacac cacccaaacc 2760
caaggcaaca actttgctgc ggatcaacgg ggtaaagaca agtgtgcccg ggacatcggc 2820
tactacctcc gcatcgttac ctactgctta gttgctggtg gtaccggtcc tttggatgag 2880
tacttgatcg ccggtattga tgaaatcaac cgcacctttg acctctcccc cagctggtat 2940
gttctcgag 2949

<210> SEQ ID NO 13
<211> LENGTH: 2990
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
ctcgagggaa agtaggctgt ggttccctag gcaacagtct tccctacccc actggaaact 60
aaaaaaacga gaaaagttcg caccgaacat caattgcata attttagccc taaaacataa 120
gctgaacgaa actggttgtc ttcccttccc aatccaggac aatctgagaa tcccctgcaa 180
cattacttaa caaaaaagca ggaataaaat taacaagatg taacagacat aagtcccatc 240
accgttgtat aaagttaact gtgggattgc aaaagcattc aagcctaggc gctgagctgt 300
ttgagcatcc cggtggccct tgtcgctgcc tccgtgtttc tccctggatt tatttaggta 360
atatctctca taaatccccg ggtagttaac gaaagttaat ggagatcagt aacaataact 420
ctagggtcat tactttggac tccctcagtt tatccggggg aattgtgttt aagaaaatcc 480
caactcataa agtcaagtag gagattaatt caatgagtca catccagaga gaaactagtt 540
gttcccgacc tcgtttgaat agcaatatgg atgcagatct gtacggatat aaatgggcgc 600
gagataacgt aggccaatct ggggccacta tttatcggtt atatggcaaa ccagatgctc 660
ccgaactgtt tctcaaacat ggcaaagggt ctgtggccaa tgatgttacc gatgaaatgg 720
tgcggttgaa ctggttgaca gaatttatgc ccctcccgac catcaaacat tttatcagga 780

-continued

```
ctccagacga tgcatggcta ttaactacgg ccattcctgg gaaaactgcc tttcaggtgt    840
tggaagaata tcccgattct ggtgagaata tcgtcgatgc gttagcggtt tttctaagac    900
gtctacatag cattcccgtt tgcaattgtc cctttaattc ggaccgggtg ttccgcttgg    960
cgcaggctca gtcccggatg aataacggtt tggtagatgc ctcggacttt gatgatgaac   1020
ggaacggctg gcccgttgaa caggtttgga aagagatgca taagctgctg cccttctccc   1080
ccgacagcgt tgttactcat ggagattttt ctctcgataa tctgattttc gacgaaggca   1140
agctaattgg ctgtatcgat gtgggacggg tagggattgc ggaccggtat caagacctag   1200
caattttgtg gaactgccta ggtgaatttt cccccagcct acaaaaacgg ctgtttcaaa   1260
aatacggaat cgataatccc gacatgaaca aattacaatt tcatctgatg ctagatgagt   1320
tctttcacca tcaccatcac catatcgaag ggcgatccta tcaaggcaat tccgattgtt   1380
attttggcaa tggctccgcc tatcggggca cccattcctt gaccgaatcc ggcgcctcct   1440
gtttgccctg gaattccatg attttgattg gcaaagtgta taccgcccaa aatccctccg   1500
cccaagcctt gggcttgggc aaacataatt attgtcggaa tcccgatggc gatgccaaac   1560
cctggtgtca tgtgttgaag aatcggcggt tgacctggga atattgtgat gtgccctcct   1620
gttccacctg tggcttgcgg caatattccc aaccccaatt tcggattaaa ggcggcttgt   1680
ttgccgatat tgcctcccat ccctggcaag ccgccatctt tgccaaacat cggcggtctc   1740
ccggcgaacg gttcttgtgt ggcggcattt tgatttcctc ctgttggatt ttgtccgccg   1800
cccattgttt tcaagaacgg tttcctcccc atcatttgac cgtgattttg ggccggacct   1860
atcgggtggt gcccggcgaa gaagaacaga aatttgaagt ggagaaatat attgtgcata   1920
aagaatttga tgatgatacc tatgataatg atattgcctt gttgcaattg aaatccgatt   1980
cctcccggtg tgcccaagaa tcctccgtgg tgcggaccgt gtgtttgcct cccgccgatt   2040
tgcaattgcc cgattggacc gaatgtgaat tgtccggcta tggcaaacat gaagccttgt   2100
ctccctttta ttccgaacgg ttgaaagaag cccatgtgcg gttgtatccc tcctcccggt   2160
gtacctccca acatttgttg aatcggaccg tgaccgataa tatgttgtgt gccggcgata   2220
cccggtccgg cggcccccaa gccaatttgc atgatgcctg tcaaggcgat tccggcggcc   2280
ccttggtgtg tttgaatgat ggccggatga ccttggtggg cattatttcc tggggcttgg   2340
gctgtggcca gaaagatgtg cccggcgtgt ataccaaagt gaccaattat ttggattgga   2400
ttcgggataa tatgcggccc taattttttt aaggcagtta ttggtgccct taaacgcctg   2460
gggatcctct ggttatttta aaaaccaact ttactcaggt tccatacccg agaaaatcca   2520
gcttaaagct gacatatcta ggaaaatttt cacattctaa cgggagatac cagaacaatg   2580
aaaacccctt taactgaagc cgtttccacc gctgactctc aaggtcgctt tctgagcagc   2640
accgaattgc aaattgcttt cggtcgtcta cgtcaagcta atgctggttt gcaagccgct   2700
aaagctctga ccgacaatgc ccagagcttg gtaaatggtg ctgcccaagc cgtttataac   2760
aaattcccct acaccaccca aacccaaggc aacaactttg ctgcggatca acggggtaaa   2820
gacaagtgtg cccgggacat cggctactac ctccgcatcg ttacctactg cttagttgct   2880
ggtggtaccg gtcctttgga tgagtacttg atcgccggta ttgatgaaat caaccgcacc   2940
tttgacctct cccccagctg gtatgttgaa gctctgaaat acatctcgag              2990
```

<210> SEQ ID NO 14
<211> LENGTH: 2112
<212> TYPE: DNA

-continued

<213> ORGANISM: Artificial Sequence
<220> FEATURE:
<223> OTHER INFORMATION: Description of Artificial Sequence: Synthetic
      polynucleotide

<400> SEQUENCE: 14
atgttcgacg tattcactcg ggttgtttcc caagctgatg ctcgcggcga gtacctctct 60
ggttctcagt tagatgcttt gagcgctacc gttgctgaag gcaacaaacg gattgattct 120
gttaaccgca tcaccggtaa tgcttccgct atcgtttcca acgctgctcg tgctttgttc 180
gccgaacagc cccaattaat ccaacccggt ggaaacgcct acaccagccg tcgtatggct 240
gcttgtttgc gtgacatgga aatcatcctc cgctatgtta cctacgcaac cttcaccggc 300
gacgcttccg ttctagaaga tcgttgcttg aacggtctcc gtgaaaccta cgttgccctg 360
ggtgttcccg gtgcttccgt agctgctggc gttcaaaaaa tgaaagaagc tgccctggac 420
atcgttaacg atcccaatgg catcacccgt ggtgattgca gtgctatcgt tgctgaaatc 480
gctggttact tcgaccgcgc cgctgctgcc gtagccatcg aagggcgatt cgtgaaccag 540
cacttgtgcg gtagtcactt agtcgaagcg ctctatctag tctgtggtga acgaggtttc 600
ttctatactc ctaagactcg acgtgaggct gaggacctcc aagtaggaca ggtagaacta 660
ggaggcggac caggagccgg gtctttgcag ccgttggcac tagaagggag cctccagaag 720
cgagggatcg tggagcagtg ctgcacatcc atctgtagct tataccaatt agagaattac 780
tgcaattaga gatctgcggc cgcgttgatc ggcacgtaag aggttccaac tttcaccata 840
atgaaataag atcactaccg ggcgtatttt ttgagttatc gagattttca ggagctaagg 900
aagctaaaat ggagaaaaaa atcactggat ataccaccgt tgatatatcc caatggcatc 960
gtaaagaaca ttttgaggca tttcagtcag ttgctcaatg tacctataac cagaccgttc 1020
agctggatat tacggccttt ttaaagaccg taaagaaaaa taagcacaag ttttatccgg 1080
cctttattca cattcttgcc cgcctgatga atgctcatcc ggaattccgt atggcaatga 1140
aagacggtga gctggtgata tgggatagtg ttcacccttg ttacaccgtt ttccatgagc 1200
aaactgaaac gttttcatcg ctctggagtg aataccacga cgatttccgg cagtttctac 1260
acatatattc gcaagatgtg gcgtgttacg gtgaaaacct ggcctatttc cctaaagggt 1320
ttattgagaa tatgtttttc gtctcagcca atccctgggt gagtttcacc agttttgatt 1380
taaacgtggc caatatggac aacttcttcg cccccgtttt caccatgggc aaatattata 1440
cgcaaggcga caaggtgctg atgccgctgg cgattcaggt tcatcatgcc gtctgtgatg 1500
gcttccatgt cggcagaatg cttaatgaat tacaacagta ctgcgatgag tggcagggcg 1560
gggcgtaatt tttttaaggc agttattggt gcccttaaac gcctggggat cctctggtta 1620
ttttaaaaac caactttact caggttccat acccgagaaa atccagctta aagctgacat 1680
atctaggaaa attttcacat tctaacggga gataccagaa caatgaaaac ccctttaact 1740
gaagccgttt ccaccgctga ctctcaaggt cgctttctga gcagcaccga attgcaaatt 1800
gctttcggtc gtctacgtca agctaatgct ggtttgcaag ccgctaaagc tctgaccgac 1860
aatgcccaga gcttggtaaa tggtgctgcc caagccgttt ataacaaatt cccctacacc 1920
acccaaaccc aaggcaacaa ctttgctgcg gatcaacggg gtaaagacaa gtgtgcccgg 1980
gacatcggct actacctccg catcgttacc tactgcttag ttgctggtgg taccggtcct 2040
ttggatgagt acttgatcgc cggtattgat gaaatcaacc gcacctttga cctctccccc 2100
agctggtatg tt 2112

```
<210> SEQ ID NO 15
<211> LENGTH: 451
<212> TYPE: PRT
<213> ORGANISM: Clostridium tetani

<400> SEQUENCE: 15

Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Asp Thr Asn Glu Tyr Ser Ile
            100                 105                 110

Ile Ser Ser Met Lys Lys Tyr Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Ser Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
    210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Tyr Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
    290                 295                 300

Leu Tyr Ser Gly Leu Lys Phe Ile Ile Lys Arg Tyr Thr Pro Asn Asn
305                 310                 315                 320

Glu Ile Asp Ser Phe Val Arg Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Arg Val Gly Tyr Asn Ala Pro
        355                 360                 365

Gly Ile Pro Leu Tyr Lys Lys Met Glu Ala Val Lys Leu Arg Asp Leu
    370                 375                 380
```

```
Lys Thr Tyr Ser Val Gln Leu Lys Leu Tyr Asp Asp Lys Asp Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430

Lys Thr Leu Thr Cys Asp Trp Tyr Phe Val Pro Thr Asp Glu Gly Trp
        435                 440                 445

Thr Asn Asp
    450


<210> SEQ ID NO 16
<211> LENGTH: 223
<212> TYPE: PRT
<213> ORGANISM: Severe acute respiratory syndrome coronavirus 2

<400> SEQUENCE: 16

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 17
<211> LENGTH: 673
<212> TYPE: PRT
<213> ORGANISM: Severe acute respiratory syndrome coronavirus 2

<400> SEQUENCE: 17

Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30
```

-continued

```
Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Asp Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
                85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Asp Pro Phe
        115                 120                 125

Leu Gly Val Tyr Tyr His Lys Asn Asn Lys Ser Trp Met Glu Ser Glu
    130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
                165                 170                 175

Leu Arg Glu Phe Val Phe Lys Asn Ile Asp Gly Tyr Phe Lys Ile Tyr
            180                 185                 190

Ser Lys His Thr Pro Ile Asn Leu Val Arg Asp Leu Pro Gln Gly Phe
        195                 200                 205

Ser Ala Leu Glu Pro Leu Val Asp Leu Pro Ile Gly Ile Asn Ile Thr
    210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Ala Tyr Tyr Val Gly
                245                 250                 255

Tyr Leu Gln Pro Arg Thr Phe Leu Leu Lys Tyr Asn Glu Asn Gly Thr
            260                 265                 270

Ile Thr Asp Ala Val Asp Cys Ala Leu Asp Pro Leu Ser Glu Thr Lys
        275                 280                 285

Cys Thr Leu Lys Ser Phe Thr Val Glu Lys Gly Ile Tyr Gln Thr Ser
    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
        355                 360                 365

Gly Val Ser Pro Thr Lys Leu Asn Asp Leu Cys Phe Thr Asn Val Tyr
    370                 375                 380

Ala Asp Ser Phe Val Ile Arg Gly Asp Glu Val Arg Gln Ile Ala Pro
385                 390                 395                 400

Gly Gln Thr Gly Lys Ile Ala Asp Tyr Asn Tyr Lys Leu Pro Asp Asp
                405                 410                 415

Phe Thr Gly Cys Val Ile Ala Trp Asn Ser Asn Asn Leu Asp Ser Lys
            420                 425                 430

Val Gly Gly Asn Tyr Asn Tyr Leu Tyr Arg Leu Phe Arg Lys Ser Asn
        435                 440                 445
```

-continued

```
Leu Lys Pro Phe Glu Arg Asp Ile Ser Thr Glu Ile Tyr Gln Ala Gly
    450                 455                 460

Ser Thr Pro Cys Asn Gly Val Glu Gly Phe Asn Cys Tyr Phe Pro Leu
465                 470                 475                 480

Gln Ser Tyr Gly Phe Gln Pro Thr Asn Gly Val Gly Tyr Gln Pro Tyr
                485                 490                 495

Arg Val Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
        515                 520                 525

Phe Asn Phe Asn Gly Leu Thr Gly Thr Gly Val Leu Thr Glu Ser Asn
    530                 535                 540

Lys Lys Phe Leu Pro Phe Gln Gln Phe Gly Arg Asp Ile Ala Asp Thr
545                 550                 555                 560

Thr Asp Ala Val Arg Asp Pro Gln Thr Leu Glu Ile Leu Asp Ile Thr
                565                 570                 575

Pro Cys Ser Phe Gly Gly Val Ser Val Ile Thr Pro Gly Thr Asn Thr
            580                 585                 590

Ser Asn Gln Val Ala Val Leu Tyr Gln Asp Val Asn Cys Thr Glu Val
        595                 600                 605

Pro Val Ala Ile His Ala Asp Gln Leu Thr Pro Thr Trp Arg Val Tyr
    610                 615                 620

Ser Thr Gly Ser Asn Val Phe Gln Thr Arg Ala Gly Cys Leu Ile Gly
625                 630                 635                 640

Ala Glu His Val Asn Asn Ser Tyr Glu Cys Asp Ile Pro Ile Gly Ala
                645                 650                 655

Gly Ile Cys Ala Ser Tyr Gln Thr Gln Thr Asn Ser Pro Arg Arg Ala
            660                 665                 670

Arg
```

<210> SEQ ID NO 18
<211> LENGTH: 103
<212> TYPE: PRT
<213> ORGANISM: Vibrio cholerae

<400> SEQUENCE: 18

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

<210> SEQ ID NO 19
<211> LENGTH: 2199
<212> TYPE: DNA
<213> ORGANISM: Artificial Sequence
<220> FEATURE:

-continued

<223> OTHER INFORMATION: Description of Artificial Sequence: Synthetic polynucleotide

<400> SEQUENCE: 19

```
atgttcgacg tattcactcg ggttgtttcc caagctgatg ctcgcggcga gtacctctct     60
ggttctcagt tagatgcttt gagcgctacc gttgctgaag gcaacaaacg gattgattct    120
gttaaccgca tcaccggtaa tgcttccgct atcgtttcca acgctgctcg tgctttgttc    180
gccgaacagc cccaattaat ccaacccggt ggaaacgcct acaccagccg tcgtatggct    240
gcttgtttgc gtgacatgga aatcatcctc cgctatgtta cctacgcaac cttcaccggc    300
gacgcttccg ttctagaaga tcgttgcttg aacggtctcc gtgaaaccta cgttgccctg    360
ggtgttcccg gtgcttccgt agctgctggc gttcaaaaaa tgaaagaagc tgccctggac    420
atcgttaacg atcccaatgg catcacccgt ggtgattgca gtgctatcgt tgctgaaatc    480
gctggttact tcgaccgcgc cgctgctgcc gtagccccca tgccttggcg cgtgattcac    540
catcaccatc accatgataa tttgtattta caaggcaccc cccaaaatat taccgatttg    600
tgtgccgaat atcataatac ccaaattcat accttgaatg ataaaatttt ttcctatacc    660
gaatccttgg ccggcaaacg ggaaatggcc attattacct ttaaaaatgg cgccaccttt    720
caagtggaag tgcccggctc ccaacatatt gattcccaaa aaaaagccat tgaacggatg    780
aaagatacct tgcggattgc ctatttgacc gaagccaaag tggaaaaatt gtgtgtgtgg    840
aataataaaa ccccccatgc cattgccgcc atttccatgg ccaattgagg aattaggagg    900
taatatatga gggaagcggt gatcgccgaa gtatcgactc aactatcaga ggtagttggc    960
gtcatcgagc gccatctcga accgacgttg ctggccgtac atttgtacgg ctccgcagtg   1020
gatggcggcc tgaagccaca cagtgatatt gatttgctgg ttacggtgac cgtaaggctt   1080
gatgaaacaa cgcggcgagc tttgatcaac gaccttttgg aaacttcggc ttcccctgga   1140
gagagcgaga ttctccgcgc tgtagaagtc accattgttg tgcacgacga catcattccg   1200
tggcgttatc cagctaagcg cgaactgcaa tttggagaat ggcagcgcaa tgacattctt   1260
gcaggtatct tcgagccagc cacgatcgac attgatctgg ctatcttgct gacaaaagca   1320
agagaacata gcgttgcctt ggtaggtcca gcggcggagg aactctttga tccggttcct   1380
gaacaggatc tatttgaggc gctaaatgaa accttaacgc tatggaactc gccgcccgac   1440
tgggctggcg atgagcgaaa tgtagtgctt acgttgtccc gcatttggta cagcgcagta   1500
accggcaaaa tcgcgccgaa ggatgtcgct gccgactggg caatggagcg cctgccggcc   1560
cagtatcagc ccgtcatact tgaagctaga caggcttatc ttggacaaga agaagatcgc   1620
ttggcctcgc gcgcagatca gttggaagaa tttgtccact acgtgaaagg cgagatcacc   1680
aaggtagtcg gcaaataatt tttttaaggc agttattggt gcccttaaac gcctggggat   1740
cctctggtta ttttaaaaac caactttact caggttccat acccgagaaa atccagctta   1800
aagctgacat atctaggaaa attttcacat tctaacggga gataccagaa caatgaaaac   1860
ccctttaact gaagccgttt ccaccgctga ctctcaaggt cgctttctga gcagcaccga   1920
attgcaaatt gctttcggtc gtctacgtca agctaatgct ggtttgcaag ccgctaaagc   1980
tctgaccgac aatgcccaga gcttggtaaa tggtgctgcc caagccgttt ataacaaatt   2040
cccctacacc acccaaaccc aaggcaacaa ctttgctgcg gatcaacggg gtaaagacaa   2100
gtgtgcccgg gacatcggct actacctccg catcgttacc tactgcttag ttgctggtgg   2160
taccggtcct ttggatgagt acttgatcgc cggtattga                          2199
```

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 20

His His His His His His
1 5

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
caccatcacc atcaccatga taatttgtat ttacaaggc 39

<210> SEQ ID NO 22
<211> LENGTH: 3243
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
atgttcgacg tattcactcg ggttgtttcc caagctgatg ctcgcggcga gtacctctct 60
ggttctcagt tagatgcttt gagcgctacc gttgctgaag gcaacaaacg gattgattct 120
gttaaccgca tcaccggtaa tgcttccgct atcgtttcca acgctgctcg tgctttgttc 180
gccgaacagc cccaattaat ccaacccggt ggaaacgcct acaccagccg tcgtatggct 240
gcttgtttgc gtgacatgga aatcatcctc cgctatgtta cctacgcaac cttcaccggc 300
gacgcttccg ttctagaaga tcgttgcttg aacggtctcc gtgaaaccta cgttgccctg 360
ggtgttcccg gtgcttccgt agctgctggc gttcaaaaaa tgaaagaagc tgccctggac 420
atcgttaacg atcccaatgg catcacccgt ggtgattgca gtgctatcgt tgctgaaatc 480
gctggttact tcgaccgcgc cgctgctgcc gtagccccca tgccttggcg cgtgattcac 540
catcaccatc accatgataa tttgtattta caaggcaaga acttagactg ttgggtcgat 600
aatgaggagg atatcgatgt cattctaaag aagtctacca tcctaaatct ggacattaac 660
aatgatatca ttagtgatat ttctggtttt aattcttctg ttatcacata ccccgacgcc 720
caattagttc caggaattaa tgggaaggct attcatctag taaataatga gagcagcgaa 780
gtgatcgtcc acaaggcgat ggacattgag tataatgata tgttcaacaa ctttactgtg 840 tcctttttggt tgcgcgtccc caaagtgtct gccagtcacc tggaacaata cgacacgaat 900
gaatatagta tcattagcag tatgaaaaag tatagtttaa gtattgggtc tgggtggtcc 960
gtctctctca aaggaaacaa cctcatctgg accctcaagg attctgcagg cgaagtgcgt 1020
caaattacat tccgcgactt gtccgataaa ttcaatgcgt acctcgctaa caaatgggtt 1080
ttcatcacca tcacgaacga ccggctgagt agcgctaacc tctacattaa tggcgtgttg 1140
atggggagtg cggagatcac cggcctgggg gcaattcgcg aggacaacaa catcacactc 1200
aagttggacc gttgcaataa caacaaccaa tatgtctcta tcgacaaatt tcgtattttc 1260

-continued

```
tgtaaggcgc taaacccaaa ggagatcgaa aagttatata ctagttattt gagcatcacg   1320

tttttacgcg atttttgggg caacccactg cgttatgaca ctgaatatta tctcattccc   1380

gttgcgtaca gcagtaaaga cgtccaatta aagaatatca cggattatat gtatctgact   1440

aatgctccca gttacacgaa cgggaaatta aacatttact accgccgtct gtactctggt   1500

ctgaagttta ttatcaaacg ctacaccccc aacaatgaaa tcgactcttt tgttcggtct   1560

ggtgacttta ttaaactgta cgtaagttac aacaacaatg aacacatcgt gggataccct   1620

aaagacggga atgcgttcaa taacttagat cggatcctcc gagtagggta taatgcaccc   1680

ggtattcctc tgtataagaa gatggaagcg gtaaagctcc gtgacctcaa aacttatagc   1740

gtgcaactca aactgtacga cgacaaagat gcgtctctag ggttggtggg tacccacaac   1800

ggacaaatcg ggaatgaccc taaccgcgat attctaatcg cttctaattg gtattttaac   1860

cacttaaaag ataagaccct cacctgcgac tggtatttcg tcccaaccga cgagggatgg   1920

actaatgatt gaggaattag gaggtaatat atgagggaag cggtgatcgc cgaagtatcg   1980

actcaactat cagaggtagt tggcgtcatc gagcgccatc tcgaaccgac gttgctggcc   2040

gtacatttgt acggctccgc agtggatggc ggcctgaagc cacacagtga tattgatttg   2100

ctggttacgg tgaccgtaag gcttgatgaa acaacgcggc gagctttgat caacgacctt   2160

ttggaaactt cggcttcccc tggagagagc gagattctcc gcgctgtaga agtcaccatt   2220

gttgtgcacg acgacatcat tccgtggcgt tatccagcta agcgcgaact gcaatttgga   2280

gaatggcagc gcaatgacat tcttgcaggt atcttcgagc cagccacgat cgacattgat   2340

ctggctatct tgctgacaaa agcaagagaa catagcgttg ccttggtagg tccagcggcg   2400

gaggaactct ttgatccggt tcctgaacag gatctatttg aggcgctaaa tgaaacctta   2460

acgctatgga actcgccgcc cgactgggct ggcgatgagc gaaatgtagt gcttacgttg   2520

tcccgcattt ggtacagcgc agtaaccggc aaaatcgcgc cgaaggatgt cgctgccgac   2580

tgggcaatgg agcgcctgcc ggcccagtat cagcccgtca tacttgaagc tagacaggct   2640

tatcttggac aagaagaaga tcgcttggcc tcgcgcgcag atcagttgga agaatttgtc   2700

cactacgtga aaggcgagat caccaaggta gtcggcaaat aatttttta aggcagttat   2760

tggtgccctt aaacgcctgg ggatcctctg gttattttaa aaaccaactt tactcaggtt   2820

ccatacccga gaaaatccag cttaaagctg acatatctag gaaaattttc acattctaac   2880

gggagatacc agaacaatga aaaccccttt aactgaagcc gtttccaccg ctgactctca   2940

aggtcgcttt ctgagcagca ccgaattgca aattgctttc ggtcgtctac gtcaagctaa   3000

tgctggtttg caagccgcta aagctctgac cgacaatgcc cagagcttgg taaatggtgc   3060

tgcccaagcc gtttataaca aattccccta caccacccaa acccaaggca acaactttgc   3120

tgcggatcaa cggggtaaag acaagtgtgc ccgggacatc ggctactacc tccgcatcgt   3180

tacctactgc ttagttgctg gtggtaccgg tcctttggat gagtacttga tcgccggtat   3240

tga                                                                  3243
```

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
ggaattagga ggtaatat                                               18


<210> SEQ ID NO 24
<211> LENGTH: 2559
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

atgttcgacg tattcactcg ggttgtttcc caagctgatg ctcgcggcga gtacctctct     60

ggttctcagt tagatgcttt gagcgctacc gttgctgaag gcaacaaacg gattgattct    120

gttaaccgca tcaccggtaa tgcttccgct atcgtttcca acgctgctcg tgctttgttc    180

gccgaacagc cccaattaat ccaacccggt ggaaacgcct acaccagccg tcgtatggct    240

gcttgtttgc gtgacatgga aatcatcctc cgctatgtta cctacgcaac cttcaccggc    300

gacgcttccg ttctagaaga tcgttgcttg aacggtctcc gtgaaaccta cgttgccctg    360

ggtgttcccg gtgcttccgt agctgctggc gttcaaaaaa tgaaagaagc tgccctggac    420

atcgttaacg atcccaatgg catcacccgt ggtgattgca gtgctatcgt tgctgaaatc    480

gctggttact tcgaccgcgc cgctgctgcc gtagccccca tgccttggcg cgtgattcac    540

catcaccatc accatgataa tttgtattta caaggccggg tgcaacccac cgaatccatt    600

gtgcggtttc ccaatattac caatttgtgt ccctttggcg aagtgtttaa tgccacccgg    660

tttgcctccg tgtatgcctg gaatcggaaa cggatttcca attgtgtggc cgattattcc    720

gtgttgtata attccgcctc cttttccacc tttaaatgtt atggcgtgtc ccccaccaaa    780

ttgaatgatt tgtgttttac caatgtgtat gccgattcct ttgtgattcg gggcgatgaa    840

gtgcggcaaa ttgcccccgg ccaaaccggc aaaattgccg attataatta taaattgccc    900

gatgatttta ccggctgtgt gattgcctgg aattccaata atttggattc caaagtgggc    960

ggcaattata attatttgta tcggttgttt cggaaatcca atttgaaacc ctttgaacgg   1020

gatatttcca ccgaaattta tcaagccggc tccacccccct gtaatggcgt ggaaggcttt   1080

aattgttatt ttcccttgca atcctatggc tttcaaccca ccaatggcgt gggctatcaa   1140

ccctatcggg tggtggtgtt gtcctttgaa ttgttgcatg cccccgccac cgtgtgtggc   1200

cccaaaaaat ccaccaattt ggtgaaaaat aaatgtgtga atttttgagg aattaggagg   1260

taatatatga gggaagcggt gatcgccgaa gtatcgactc aactatcaga ggtagttggc   1320

gtcatcgagc gccatctcga accgacgttg ctggccgtac atttgtacgg ctccgcagtg   1380

gatggcggcc tgaagccaca cagtgatatt gatttgctgg ttacggtgac cgtaaggctt   1440

gatgaaacaa cgcggcgagc tttgatcaac gaccttttgg aaacttcggc ttcccctgga   1500

gagagcgaga ttctccgcgc tgtagaagtc accattgttg tgcacgacga catcattccg   1560

tggcgttatc cagctaagcg cgaactgcaa tttggagaat ggcagcgcaa tgacattctt   1620

gcaggtatct tcgagccagc cacgatcgac attgatctgg ctatcttgct gacaaaagca   1680

agagaacata gcgttgcctt ggtaggtcca gcggcggagg aactctttga tccggttcct   1740

gaacaggatc tatttgaggc gctaaatgaa accttaacgc tatggaactc gccgcccgac   1800

tgggctggcg atgagcgaaa tgtagtgctt acgttgtccc gcatttggta cagcgcagta   1860

accggcaaaa tcgcgccgaa ggatgtcgct gccgactggg caatggagcg cctgccggcc   1920

cagtatcagc ccgtcatact tgaagctaga caggcttatc ttggacaaga agaagatcgc   1980
```

-continued ttggcctcgc gcgcagatca gttggaagaa tttgtccact acgtgaaagg cgagatcacc 2040
aaggtagtcg gcaaataatt tttttaaggc agttattggt gcccttaaac gcctggggat 2100
cctctggtta ttttaaaaac caactttact caggttccat acccgagaaa atccagctta 2160
aagctgacat atctaggaaa attttcacat tctaacggga gataccagaa caatgaaaac 2220
ccctttaact gaagccgttt ccaccgctga ctctcaaggt cgctttctga gcagcaccga 2280
attgcaaatt gctttcggtc gtctacgtca agctaatgct ggtttgcaag ccgctaaagc 2340
tctgaccgac aatgcccaga gcttggtaaa tggtgctgcc caagccgttt ataacaaatt 2400
cccctacacc acccaaaccc aaggcaacaa ctttgctgcg gatcaacggg gtaaagacaa 2460
gtgtgcccgg gacatcggct actacctccg catcgttacc tactgcttag ttgctggtgg 2520
taccggtcct ttggatgagt acttgatcgc cggtattga 2559

<210> SEQ ID NO 25
<211> LENGTH: 3909
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25
atgttcgacg tattcactcg ggttgtttcc caagctgatg ctcgcggcga gtacctctct 60
ggttctcagt tagatgcttt gagcgctacc gttgctgaag gcaacaaacg gattgattct 120
gttaaccgca tcaccggtaa tgcttccgct atcgtttcca acgctgctcg tgctttgttc 180
gccgaacagc cccaattaat ccaacccggt ggaaacgcct acaccagccg tcgtatggct 240
gcttgtttgc gtgacatgga aatcatcctc cgctatgtta cctacgcaac cttcaccggc 300
gacgcttccg ttctagaaga tcgttgcttg aacggtctcc gtgaaaccta cgttgccctg 360
ggtgttcccg gtgcttccgt agctgctggc gttcaaaaaa tgaaagaagc tgccctggac 420
atcgttaacg atcccaatgg catcacccgt ggtgattgca gtgctatcgt tgctgaaatc 480
gctggttact tcgaccgcgc cgctgctgcc gtagccccca tgccttggcg cgtgattcac 540
catcaccatc accatgataa tttgtattta caaggctccc aatgtgtgaa tttgaccacc 600
cggacccaat tgccccccgc ctataccaat tcctttaccc ggggcgtgta ttatcccgat 660
aaagtgtttc ggtcctccgt gttgcattcc acccaagatt tgtttttgcc ctttttttcc 720
aatgtgacct ggtttcatgc cattcatgtg tccggcacca atggcaccaa acggtttgat 780
aatcccgtgt tgccctttaa tgatggcgtg tattttgcct ccaccgaaaa atccaatatt 840
attcggggct ggatttttgg caccaccttg gattccaaaa cccaatcctt gttgattgtg 900
aataatgcca ccaatgtggt gattaaagtg tgtgaatttc aattttgtaa tgatcccttt 960
ttgggcgtgt attatcataa aaataataaa tcctggatgg aatccgaatt tcgggtgtat 1020
tcctccgcca ataattgtac ctttgaatat gtgtcccaac cctttttgat ggatttggaa 1080
ggcaaacaag gcaattttaa aaatttgcgg gaatttgtgt ttaaaaatat tgatggctat 1140
tttaaaattt attccaaaca tacccccatt aatttggtgc gggatttgcc ccaaggcttt 1200
tccgccttgg aacccttggt ggatttgccc attggcatta atattacccg gtttcaaacc 1260
ttgttggcct tgcatcggtc ctatttgacc cccggcgatt cctcctccgg ctggaccgcc 1320
ggcgccgccg cctattatgt gggctatttg caaccccgga cctttttgtt gaaatataat 1380
gaaaatggca ccattaccga tgccgtggat tgtgccttgg atcccttgtc cgaaaccaaa 1440

-continued

```
tgtaccttga aatcctttac cgtggaaaaa ggcatttatc aaacctccaa ttttcgggtg   1500
caacccaccg aatccattgt gcggtttccc aatattacca atttgtgtcc ctttggcgaa   1560
gtgtttaatg ccacccggtt tgcctccgtg tatgcctgga atcggaaacg gatttccaat   1620
tgtgtggccg attattccgt gttgtataat tccgcctcct tttccacctt taaatgttat   1680
ggcgtgtccc ccaccaaatt gaatgatttg tgttttacca atgtgtatgc cgattccttt   1740
gtgattcggg gcgatgaagt gcggcaaatt gcccccggcc aaaccggcaa aattgccgat   1800
tataattata aattgcccga tgattttacc ggctgtgtga ttgcctggaa ttccaataat   1860
ttggattcca aagtgggcgg caattataat tatttgtatc ggttgtttcg gaaatccaat   1920
ttgaaaccct ttgaacggga tatttccacc gaaatttatc aagccggctc caccccctgt   1980
aatggcgtgg aaggctttaa ttgttatttt cccttgcaat cctatggctt tcaacccacc   2040
aatggcgtgg gctatcaacc ctatcgggtg gtggtgttgt cctttgaatt gttgcatgcc   2100
cccgccaccg tgtgtggccc caaaaaatcc accaatttgg tgaaaaataa atgtgtgaat   2160
tttaatttta atggcttgac cggcaccggc gtgttgaccg aatccaataa aaaatttttg   2220
ccctttcaac aatttggccg ggatattgcc gataccaccg atgccgtgcg ggatccccaa   2280
accttggaaa ttttggatat taccccctgt tcctttggcg gcgtgtccgt gattaccccc   2340
ggcaccaata cctccaatca agtggccgtg ttgtatcaag atgtgaattg taccgaagtg   2400
cccgtggcca ttcatgccga tcaattgacc cccacctggc gggtgtattc caccggctcc   2460
aatgtgtttc aaacccgggc cggctgtttg attggcgccg aacatgtgaa taattcctat   2520
gaatgtgata ttcccattgg cgccggcatt tgtgcctcct atcaaaccca aaccaattcc   2580
ccccggcggg cccggtgagg aattaggagg taatatatga gggaagcggt gatcgccgaa   2640
gtatcgactc aactatcaga ggtagttggc gtcatcgagc gccatctcga accgacgttg   2700
ctggccgtac atttgtacgg ctccgcagtg gatggcggcc tgaagccaca cagtgatatt   2760
gatttgctgg ttacggtgac cgtaaggctt gatgaaacaa cgcggcgagc tttgatcaac   2820
gaccttttgg aaacttcggc ttcccctgga gagagcgaga ttctccgcgc tgtagaagtc   2880
accattgttg tgcacgacga catcattccg tggcgttatc cagctaagcg cgaactgcaa   2940
tttggagaat ggcagcgcaa tgacattctt gcaggtatct tcgagccagc cacgatcgac   3000
attgatctgg ctatcttgct gacaaaagca agagaacata gcgttgcctt ggtaggtcca   3060
gcggcggagg aactctttga tccggttcct gaacaggatc tatttgaggc gctaaatgaa   3120
accttaacgc tatggaactc gccgcccgac tgggctggcg atgagcgaaa tgtagtgctt   3180
acgttgtccc gcatttggta cagcgcagta accggcaaaa tcgcgccgaa ggatgtcgct   3240
gccgactggg caatggagcg cctgccggcc cagtatcagc ccgtcatact tgaagctaga   3300
caggcttatc ttggacaaga agaagatcgc ttggcctcgc gcgcagatca gttggaagaa   3360
tttgtccact acgtgaaagg cgagatcacc aaggtagtcg gcaaataatt tttttaaggc   3420
agttattggt gcccttaaac gcctggggat cctctggtta ttttaaaaac caactttact   3480
caggttccat acccgagaaa atccagctta aagctgacat atctaggaaa attttcacat   3540
tctaacggga gataccagaa caatgaaaac ccctttaact gaagccgttt ccaccgctga   3600
ctctcaaggt cgctttctga gcagcaccga attgcaaatt gctttcggtc gtctacgtca   3660
agctaatgct ggtttgcaag ccgctaaagc tctgaccgac aatgcccaga gcttggtaaa   3720
tggtgctgcc caagccgttt ataacaaatt cccctacacc acccaaaccc aaggcaacaa   3780
```

-continued

| | |
|---|---|
| ctttgctgcg gatcaacggg gtaaagacaa gtgtgcccgg gacatcggct actacctccg | 3840 |
| catcgttacc tactgcttag ttgctggtgg taccggtcct ttggatgagt acttgatcgc | 3900 |
| cggtattga | 3909 |